United States Patent
Mach et al.

(10) Patent No.: US 11,542,282 B2
(45) Date of Patent: Jan. 3, 2023

(54) LOW AFFINITY POLY(AD-RIBOSE) POLYMERASE 1 DEPENDENT CYTOTOXIC AGENTS

(71) Applicant: THE TRUSTEES OF THE UNIVERSITY OF PENNSYLVANIA, Philadelphia, PA (US)

(72) Inventors: Robert H. Mach, Wallingford, PA (US); Sean W. Reilly, Philadelphia, PA (US); Mehran Makvandi, Philadelphia, PA (US); Laura Puentes, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 16/976,515

(22) PCT Filed: Feb. 28, 2019

(86) PCT No.: PCT/US2019/020091
§ 371 (c)(1),
(2) Date: Aug. 28, 2020

(87) PCT Pub. No.: WO2019/169156
PCT Pub. Date: Sep. 6, 2019

(65) Prior Publication Data
US 2020/0407374 A1    Dec. 31, 2020

Related U.S. Application Data

(60) Provisional application No. 62/636,376, filed on Feb. 28, 2018.

(51) Int. Cl.
*C07D 491/107* (2006.01)
*C07F 5/02* (2006.01)
(Continued)

(52) U.S. Cl.
CPC ............ *C07F 5/025* (2013.01); *C07B 59/002* (2013.01); *C07D 237/32* (2013.01); *C07D 403/10* (2013.01); *C07D 471/10* (2013.01); *C07D 487/10* (2013.01); *C07D 491/107* (2013.01); *G01N 33/574* (2013.01); *G01N 33/6896* (2013.01); *C07B 2200/05* (2013.01)

(58) Field of Classification Search
CPC .. C07D 403/10; C07D 487/10; C07D 471/10; C07D 491/107; A61K 31/502; A61P 35/00
USPC ............... 544/237; 514/234.5, 238
See application file for complete search history.

(56) References Cited

U.S. PATENT DOCUMENTS 6,924,284 B2    8/2005    Beaton et al.
2008/0214591 A1   9/2008    Bhatti et al.
(Continued)

FOREIGN PATENT DOCUMENTS

CN    103570730 A    2/2014
EP    2604610 A1    6/2013
(Continued)

OTHER PUBLICATIONS

"Handbook of Pharmaceutical Excipients", 5th Edition, Eds.: Rowe, Sheskey, and Owen, APhA Publications (Washington, DC), Dec. 14, 2005.

(Continued)

*Primary Examiner* — Jeffrey H Murray
(74) *Attorney, Agent, or Firm* — BakerHostetler

(57) ABSTRACT

The present disclosure provides compounds of Formula (I) or (II), pharmaceutically acceptable salt, isotopic variant, stereoisomer, or a mixture thereof. Also provided are pharmaceutical compositions comprising a compound, methods of treating a poly(ADP-ribose)polymerase-1-mediated disease or disorder in a subject, methods of detecting a poly(ADP-ribose)polymerase-1-mediated neurodegenerative disease or disorder, or methods of monitoring cancer treatment in a subject. In some embodiments, the poly(ADP-ribose)polymerase-1-mediated disease or disorder is a neurodegenerative disease or cancer.

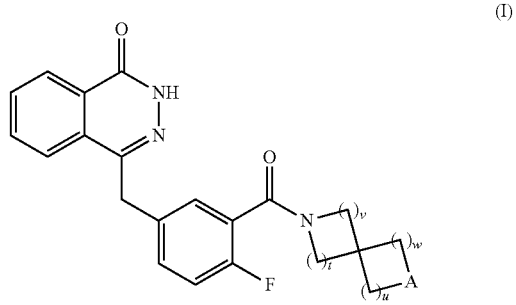

(I)

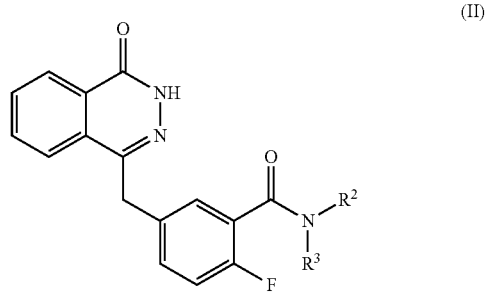

(II)

24 Claims, 6 Drawing Sheets

(51) Int. Cl.
| | |
|---|---|
| C07B 59/00 | (2006.01) |
| C07D 237/32 | (2006.01) |
| C07D 403/10 | (2006.01) |
| C07D 471/10 | (2006.01) |
| C07D 487/10 | (2006.01) |
| G01N 33/574 | (2006.01) |
| G01N 33/68 | (2006.01) |

(56) References Cited

U.S. PATENT DOCUMENTS

| | | |
|---|---|---|
| 2009/0156575 A1 | 6/2009 | Borjesson et al. |
| 2014/0065099 A1 | 3/2014 | Alvarez et al. |
| 2017/0260185 A1 | 9/2017 | Semeraro et al. |
| 2017/0266327 A1 | 9/2017 | Reiner et al. |

FOREIGN PATENT DOCUMENTS

| | | | | |
|---|---|---|---|---|
| GB | WO2004/080976 | * | 9/2004 | ........... C07D 237/32 |
| WO | 2006/021801 A1 | | 3/2006 | |
| WO | 2009/034326 A1 | | 3/2009 | |
| WO | 2009/093032 A1 | | 7/2009 | |
| WO | 2015/037939 A1 | | 3/2015 | |
| WO | 2017/021920 A1 | | 2/2017 | |

OTHER PUBLICATIONS

Deeks, Olaparib: First Global Approval, Drugs, 2015, 75 (2), pp. 231-240.
Fu et al., "Amino alcohols as ligands for nickel-catalyzed suzuki reactions of unactivated alkyl halides, including secondary alkyl chlorides, with arylboronic acids," J. Am. Chem. Soc., vol. 128, (2006), pp. 5360-5361.
Li A. et al., Evaluation of N-Phenyl Homopiperazine Analogs as Potential Dopamine D3 Receptor Selective Ligands, Bioorganic & Medicinal Chemistry 21(11), pp. 1-26 (pp. 2988-2998), 2003; abstract; p. 24, table 2, see compound 11b.
Reilly et al., "Pd-catalyzed arylation of linear and angular spirodiamine salts under aerobic conditions," Tetrahedron Lett., vol. 58, (2017), pp. 466-469.
Reilly, SW et al., "Highly Selective Dopamine D3 Receptor Antagonists with Arylated Diazaspiro Alkane Cores", Journal of Medicinal Chemistry 60 (23), pp. 9905-9910, 2017; abstract only.
Amé et al., The PARP superfamily. BioEssays 2004, 26 (8), 882-893.
Ashworth A Synthetic Lethal Therapeutic Approach: Poly(ADP) Ribose Polymerase Inhibitors for the Treatment of Cancers Deficient in DNA Double-Strand Break Repair. Journal of Clinical Oncology 2008, 26 (22), 3785-3790.
Bryant et al., Specific killing of BRCA2-deficient tumours with inhibitors of poly(ADP-ribose) polymerase. Nature 2005, 434 (7035), 913-917.
Chuang et al., Differential anti-proliferative activities of poly(ADP-ribose) polymerase (PARP) inhibitors in triple-negative breast cancer cells. Breast Cancer Research and Treatment 2012, 134 (2), 649-659.
Curtin et al., Therapeutic applications of PARP inhibitors: Anticancer therapy and beyond. Molecular Aspects of Medicine 2013, 34 (6), 1217-1256.
Deeks et al., An Update on Poly(ADP-ribose)polymerase-1 (PARP-1) Inhibitors: Opportunities and Challenges in Cancer Therapy. J. Med. Chem. 2016, 59 (21), 9575-9598.
Farmer et al., Targeting the DNA repair defect in BRCA mutant cells as a therapeutic strategy. Nature 2005, 434 (7035), 917-921.
Ferraris et al., Evolution of Poly(ADP-ribose) Polymerase-1 (PARP-1) Inhibitors. From Concept to Clinic. J. Med. Chem. 2010, 53 (12), 4561-4584.
Ferrigno, Development of substituted 6-[4-fluoro-3-(piperazin-1-ylcarbonyl)benzyl]-4,5-dimethylpyridazin-3(2H)-ones as potent poly(ADP-ribose) polymerase-1 (PARP-1) inhibitors active in BRCA deficient cells, Bioorganic & Medicinal Chemistry Letters, 20 (2010) 1100-1105.
Fong et al., Inhibition of Poly(ADP-Ribose) Polymerase in Tumors from BRCA Mutation Carriers. New England Journal of Medicine 2009, 361 (2), 123-134.
Helleday, The underlying mechanism for the PARP and BRCA synthetic lethality: Clearing up the misunderstandings. Molecular Oncology 2011, 5 (4), 387-393.
Makvandi et al., A radiotracer strategy to quantify PARP-1 expression in vivo provides a biomarker that can enable patient selection for PARP inhibitor therapy, Cancer Research Aug. 1, 2016, 76(15):4516-4524.
McCabe et al., Deficiency in the Repair of DNA Damage by Homologous Recombination and Sensitivity to Poly(ADP-Ribose) Polymerase Inhibition. Cancer Research 2006, 66 (16), 8109-8115.
Menear et al., 4-[3-(4-Cyclopropanecarbonylpiperazine-1-carbonyl)-4-fluorobenzyl]-2H-phthalazin-1-one: A Novel Bioavailable Inhibitor of Poly(ADP-ribose) Polymerase-1. J. Med. Chem. 2008, 51 (20), 6581-6591.
Murai et al., Stereospecific PARP Trapping by BMN 673 and Comparison with Olaparib and Rucaparib. Molecular Cancer Therapeutics 2014, 13 (2), 433-443.
Murai et al., Trapping of PARP1 and PARP2 by Clinical PARP Inhibitors. Cancer Research 2012, 72 (21), 5588-5599.
Pettitt et al., A Genetic Screen Using the PiggyBac Transposon in Haploid Cells Identifies Parp1 as a Mediator of Olaparib Toxicity. PloS one 2013, 8 (4), e61520.
Reilly et al., Altering Nitrogen Heterocycles of AZD2461 Affords High Affinity Poly(ADP-ribose) Polymerase-1 Inhibitors with Decreased P-Glycoprotein Interactions, ACS Omega, Aug. 31, 2018; 3(8):9997-10001; Epub Aug. 28, 2018.
Reilly et al., Examination of Diazaspiro Cores as Piperazine Bioisosteres in the Olaparib Framework Shows Reduced DNA Damage and Cytotoxicity, J. Med. Chem., Jun. 28, 2018; 61(12):5367-5379. Epub: Jun. 14, 2018.
Reilly et al., Synthesis and evaluation of an AZD2461 [18F]PET probe in non-human primates reveals the PARP-1 inhibitor to be non-blood-brain barrier penetrant, Bioorg. Chem., Mar. 2019; 83:242-249; Epub: Oct. 17, 2018.
Ricks et al., Successes and Challenges of PARP Inhibitors in Cancer Therapy. Frontiers in Oncology 2015, 5 (222).
Steffen et al., Structural Implications for Selective Targeting of PARPs. Frontiers in Oncology 2013, 3 (301).
Vyas et al., New PARP targets for cancer therapy. Nat Rev Cancer 2014, 14 (7), 502-509.
Weaver et al., Beyond DNA Repair: Additional Functions of PARP-1 in Cancer. Frontiers in Oncology 2013, 3 (290).
Zmuda et al., Synthesis and Evaluation of a Radioiodinated Tracer with Specificity for Poly(ADP-ribose) Polymerase-1 (PARP-1) in Vivo. J. Med. Chem. 2015, 58 (21), 8683-8693.
Michel et al., "PET of Poly (ADP-Ribose) Polymerase Activity in Cancer: Preclinical Assessment and First In-Human Studies", Radiology, 2017, 282, 453-463.

* cited by examiner

A

B

LOW AFFINITY POLY(AD-RIBOSE) POLYMERASE 1 DEPENDENT CYTOTOXIC AGENTS

CROSS-REFERENCE TO RELATED APPLICATIONS

This application is the National Stage Application of International Patent Application No. PCT/US2019/020091, filed Feb. 28, 2019, which claims the benefit of U.S. Provisional Application No. 62/636,376, filed Feb. 28, 2018, both of which are incorporated by reference herein.

GOVERNMENT RIGHTS

This invention was made with government support under grant numbers 5T32DA028874-07 and T32GM008076 awarded by the National Institute on Drug Abuse. The government has certain rights in the invention.

TECHNICAL FIELD

This disclosure relates to compounds and methods of imaging and treating poly(ADP-ribose)polymerase-1-mediated diseases or disorders.

BACKGROUND

Poly(ADP-ribose) polymerase-1 (PARP-1) is a nuclear protein involved in various cellular processes including detection and repair of damaged DNA. Among the 17 identified PARP enzymes, PARP-1 is the most widely investigated and pursued therapeutic target for cancer treatment due to the unique role of the protein in base excision repair (BER). Initial therapeutic strategies with PARP inhibitors (PARPi) were driven by reports demonstrating synthetic lethality of cancers deficient in breast and ovarian cancer susceptibility genes (BRCA1/2), that are responsible for encoding proteins that orchestrate homologous recombination (HR) DNA repair. Synthetic lethality refers to the simultaneous absence of two genes resulting in cell death but the presence of either functional gene confers viability.

Currently, there are three FDA-approved PARPi including, olaparib, rucaparib, and niraparib for treatment of ovarian cancer with BRCA mutations or in the maintenance therapy setting. Since then, PARPi development has quickly progressed with additional PARPi currently under clinical evaluation for cancer therapy.

Anticancer mechanisms of PARPi have also been heavily investigated in order to develop a better understanding of cancer cell drug resistance to inhibitors of PARP-1. While the overall mechanism of action is not fully understood, synthetic lethality is the classic proposal to which PARPi exert cancer cell cytotoxicity. This process describes accumulation and conversion of unrepaired DNA single strand breaks (SSBs) into double strand breaks (DSBs) due to inhibition of PARP-1 catalytic activity. These DSBs are primarily repaired through HR DNA repair pathway, thus, leading to cell survival. However, in cancerous HR deficient cells, such as those carrying BRCA1/2 mutations, these DSBs become lethal resulting in cell death. Yet, this mechanism does not fully explain why PARP-1 catalytic inhibition is poorly correlated to the cellular cytotoxicity induced by the inhibitor. While many reports have disclosed potent PARPi with poor cellular activity, examples of anti-proliferative PARP-1 dependent analogues with poor enzyme affinity are exceedingly rare. Compounds with low PARP-1 catalytic inhibition with comparable cytotoxic profiles to those of FDA approved PARPi can be used to investigate and further our understanding of PARPi anticancer mechanisms.

New compounds and methods of imaging and treating poly(ADP-ribose)polymerase-1-mediated diseases or disorders are needed.

SUMMARY

In some embodiments, the disclosure provides compounds of Formula I or II, or pharmaceutically acceptable salts thereof, wherein A, $R^1$, $R^2$, t, u, v, and w are defined herein.

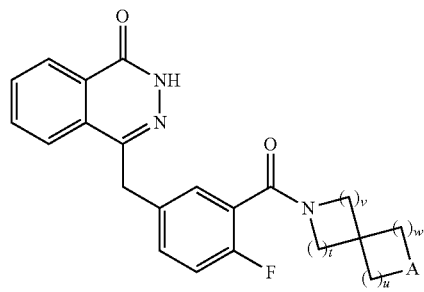

I

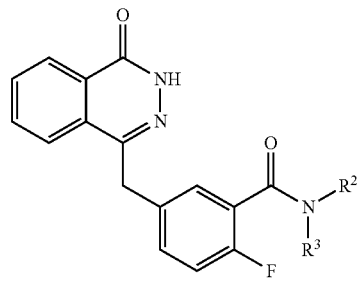

II

In other embodiments, the disclosure provides compounds of formula (IA)-(IH) or pharmaceutically acceptable salts thereof, wherein A and $R^1$ are defined herein.

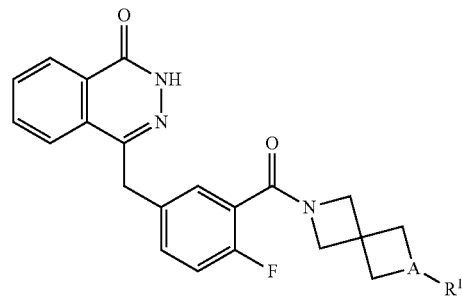

IA

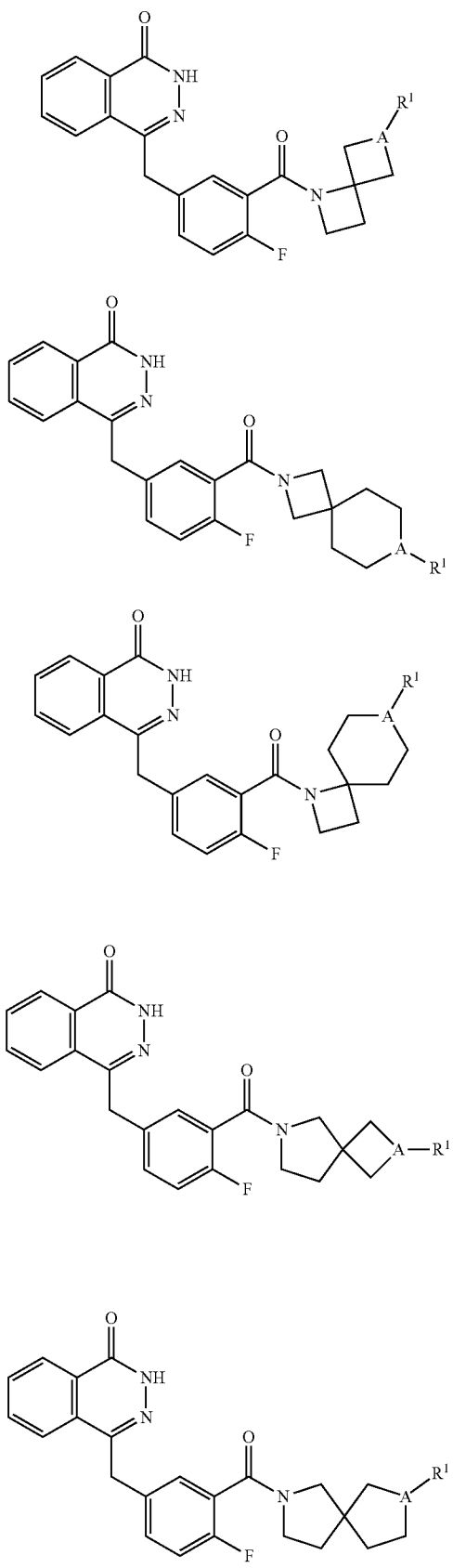
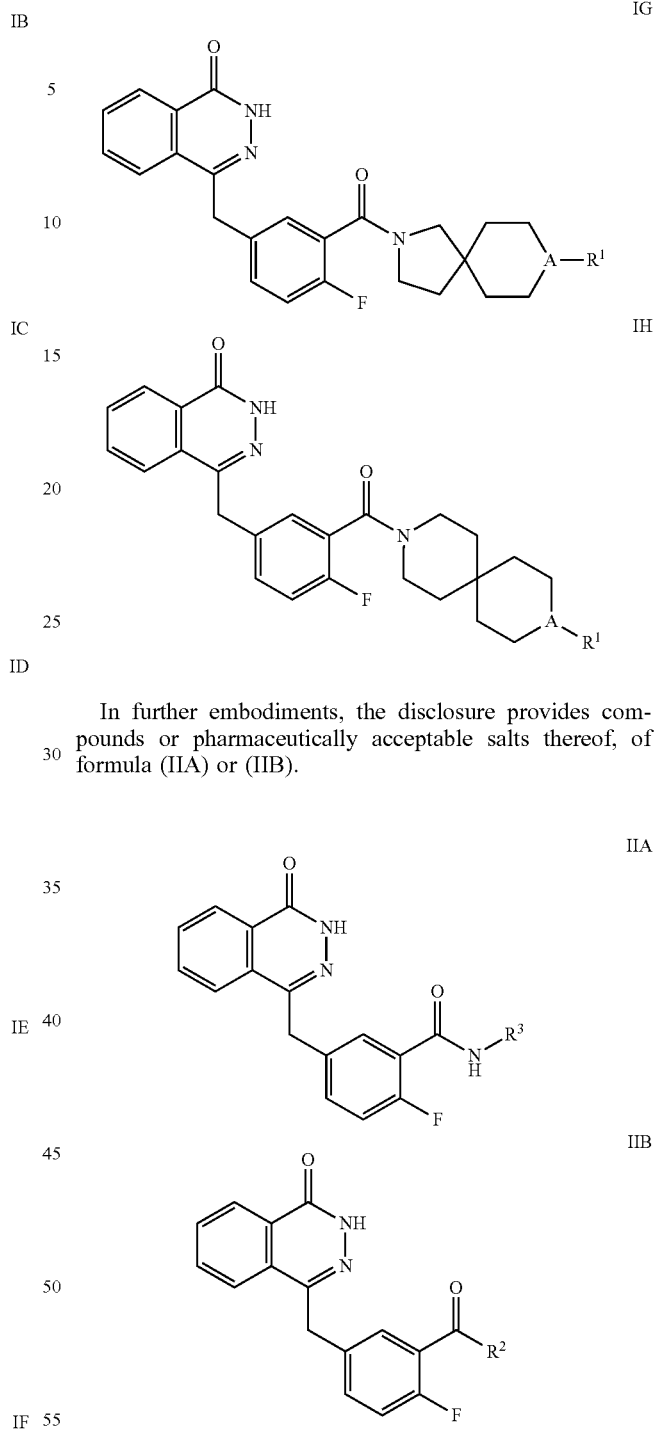

In further embodiments, the disclosure provides compounds or pharmaceutically acceptable salts thereof, of formula (IIA) or (IIB).

In yet other embodiments, the disclosure provides compounds of the above-noted formulae that are isotopic variants.

In still further embodiments, the disclosure provides pharmaceutical compositions comprising one or more compounds or pharmaceutically acceptable salts thereof and a pharmaceutically acceptable excipient.

In other embodiments, the disclosure provides methods of preparing pharmaceutical compositions described herein, comprising combining one or more compounds described herein or a pharmaceutically acceptable salt thereof, with a pharmaceutically acceptable excipient.

In further embodiments, the disclosure provides methods of treating poly(ADP-ribose)polymerase-1-mediated diseases or disorders in a subject, comprising administering to the subject a therapeutically effective amount of a compound described herein or a pharmaceutically acceptable salt thereof. In some aspects, the poly(ADP-ribose)polymerase-1-mediated disease or disorder is a neurodegenerative disease or cancer.

In still other embodiments, the disclosure provides methods of detecting a poly(ADP-ribose)polymerase-1-mediated neurodegenerative disease or disorder, comprising (a) administering an effective amount of an isotopically-labeled compound described herein to a subject; and (b) performing positron emission tomography or single photon emission computed tomography on said subject.

In yet further embodiments, the disclosure provides methods of monitoring cancer treatment in a subject, comprising (a) administering a chemotherapeutic or radiation to said subject; (b) administering an effective amount of an isotopically-labeled compound of formula I described herein to said subject; and (c) performing positron emission tomography or single photon emission computed tomography on said subject.

In other embodiments, the disclosure provides methods of detecting a poly(ADP-ribose)polymerase-1-mediated cancer in a subject, comprising (a) administering an effective amount of a compound of formula I described herein to said subject; and (b) performing positron emission tomography or single photon emission computed tomography on said subject.

Other aspects and embodiments of the invention will be readily apparent from the following detailed description of the invention.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific compositions, methods, devices, and systems disclosed. In addition, the drawings are not necessarily drawn to scale.

DETAILED DESCRIPTION OF ILLUSTRATIVE EMBODIMENTS

Figure 1A:
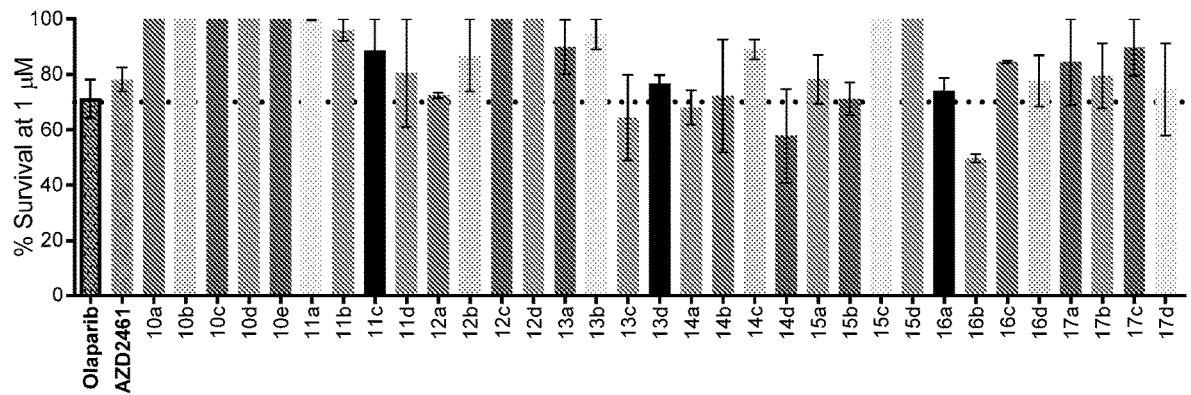
FIGS. 1A-1C depict cytotoxicity screens for compounds carried out in OVCAR8 cells at concentrations of 1 µM, 10 µM, and 100 µM.

In the present disclosure the singular forms "a", "an" and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about" it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

When a list is presented, unless stated otherwise, it is to be understood that each individual element of that list and every combination of that list is to be interpreted as a separate embodiment. For example, a list of embodiments presented as "A, B, or C" is to be interpreted as including the embodiments, "A," "B," "C," "A or B," "A or C," "B or C," or "A, B, or C."

It is to be appreciated that certain features of the invention which are, for clarity, described herein in the context of separate embodiments, may also be provided in combination in a single embodiment. That is, unless obviously incompatible or excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Finally, while an embodiment may be described as part of a series of steps or part of a more general structure, each said step may also be considered an independent embodiment in itself.

The term "alkyl," when used alone or as part of a substituent group, refers to a straight- or branched-chain alkyl group having from 1 to 12 carbon atoms ("$C_{1-12}$"), preferably 1 to 6 carbons atoms ("$C_{1-6}$"), in the chain. Examples of alkyl groups include methyl (Me, $C_1$alkyl) ethyl (Et, $C_2$alkyl), n-propyl ($C_3$alkyl), isopropyl ($C_3$alkyl), butyl ($C_4$alkyl), isobutyl ($C_4$alkyl), sec-butyl ($C_4$alkyl), tert-butyl ($C_4$alkyl), pentyl ($C_5$alkyl), isopentyl ($C_5$alkyl), tert-pentyl ($C_5$alkyl), hexyl ($C_6$alkyl), isohexyl ($C_6$alkyl), and groups that in light of the ordinary skill in the art and the teachings provided herein would be considered equivalent to any one of the foregoing examples. An alkyl moiety is optionally substituted with one, two, or three substituents selected from halo (F, Cl, Br, or I, preferably F), —OH, —O$C_{1-6}$alkyl, —CN, —NH$_2$, —NH($C_{1-6}$alkyl), —NH($C_{1-6}$alkyl)$_2$, $C_{3-8}$cycloalkyl, heterocyclyl, aryl, or heteroaryl.

The term "haloalkyl," when used alone or as part of a substituent group, refers to an alkyl group as described above having one, two, or three halogen atoms attached to a single carbon atom. Preferably, the halogen is F. In some embodiments, haloalkyl includes perfluoroalkyl groups whereby the alkyl group is terminated with a $CF_3$, $CH_2F$, or $CHF_2$. Examples of alkyl groups include $CF_3$, $CHF_2$, $CH_2F$, $CH_2CF_3$, $CHFCF_3$, $CF_2CF_3$, $CH_2CHF_2$, $CH_2CH_2F$, $CHFCH_3$, $CF_2CH_3$, $CHFCHF_2$, $CF_2CHF_2$, among others, and groups that in light of the ordinary skill in the art and the teachings provided herein would be considered equivalent to any one of the foregoing examples. A haloalkyl moiety is optionally substituted with one, two, or three substituents selected from —OH, —$OC_{1-6}$alkyl, —CN, —$NH_2$, —NH($C_{1-6}$alkyl), —NH($C_{1-6}$alkyl)$_2$, $C_{3-8}$cycloalkyl, heterocyclyl, aryl, or heteroaryl.

The term "alkoxy," when used alone or as part of a substituent group, refers to a straight- or branched-chain alkoxy group, i.e., O-alkyl, having from 1 to 12 carbon atoms ("$C_{1-12}$"), preferably 1 to 6 carbons atoms ("$C_{1-6}$"), in the chain. Examples of alkoxy groups include methoxy (OMe, $C_1$alkoxy) ethoxy (OEt, $C_2$alkoxy), n-propoxy (O$^n$Pr, $C_3$alkoxy), isopropoxy (O$^i$Pr, $C_3$alkoxy), butoxy (OBu, $C_4$alkoxy), isobutoxy (O Bu, $C_4$alkoxy), sec-butoxy (OBu, $C_4$alkoxy), tert-butoxy (O$^t$Bu, $C_4$alkoxy), pentoxy ($C_5$alkoxy), isopentoxy ($C_5$alkoxy), tert-pentoxy ($C_5$alkoxy), hexoxy ($C_6$alkoxy), isohexoxy ($C_6$alkoxy), and groups that in light of the ordinary skill in the art and the teachings provided herein would be considered equivalent to any one of the foregoing examples. An alkoxy moiety is optionally substituted with one, two, or three substituents selected from halo (F, Cl, Br, or I, preferably F), —OH, —CN, —$NH_2$, —NH($C_{1-6}$alkyl), —NH($C_{1-6}$alkyl)$_2$, $C_3$-cycloalkyl, heterocyclyl, aryl, or heteroaryl.

"Heterocyclyl" refers to a stable 3- to 18-membered non-aromatic ring radical that comprises two to twelve carbon atoms and from one to six heteroatoms selected from nitrogen, oxygen and sulfur. Whenever it appears herein, a numerical range such as "3 to 18" refers to each integer in the given range, e.g., "3 to 18 ring atoms" means that the heterocyclyl group may consist of 3 ring atoms, 4 ring atoms, etc., up to and including 18 ring atoms. Unless stated otherwise specifically in the specification, the heterocyclyl radical is a monocyclic, bicyclic, tricyclic or tetracyclic ring system, which may include fused or bridged ring systems. The heteroatoms in the heterocyclyl radical may be optionally oxidized. One or more nitrogen atoms, if present, are optionally quaternized. The heterocyclyl radical is partially or fully saturated. The heterocyclyl may be attached to the rest of the molecule through any atom of the ring(s). Examples of heterocyclyl radicals include, but are not limited to, azepanyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. "Heterocyclyl" also includes bicyclic ring systems wherein one non-aromatic ring, usually with 3 to 7 ring atoms, contains at least 2 carbon atoms in addition to 1-3 heteroatoms independently selected from oxygen, sulfur, and nitrogen, as well as combinations comprising at least one of the foregoing heteroatoms; and the other ring, usually with 3 to 7 ring atoms, optionally contains 1-3 heteroatoms independently selected from oxygen, sulfur, and nitrogen and is not aromatic. A heterocyclyl moiety is optionally substituted with one, two, or three substituents selected from halo (F, $C_1$, Br, or I, preferably F), —OH, —$OC_{1-6}$alkyl, —CN, —$NH_2$, —NH($C_{1-6}$alkyl), —NH($C_{1-6}$alkyl)$_2$, $C_{3-8}$cycloalkyl, heterocyclyl, aryl, or heteroaryl.

The term "cycloalkyl" refers to monocyclic, non-aromatic hydrocarbon groups having from 3 to 10 carbon atoms ("$C_{3-10}$"), preferably from 3 to 6 carbon atoms ("$C_{3-6}$"). Examples of cycloalkyl groups include, for example, cyclopropyl ($C_3$), cyclobutyl ($C_4$), cyclopentyl ($C_5$), cyclohexyl ($C_6$), 1-methylcyclopropyl ($C_4$), 2-methylcyclopentyl ($C_4$), adamantanyl ($C_{10}$), and the like. A cycloalkyl is optionally substituted with one, two, or three substituents selected from halo (F, $C_1$, Br, or I, preferably F), —OH, —$OC_{1-6}$alkyl, —CN, —$NH_2$, —NH($C_{1-6}$alkyl), —NH($C_{1-6}$alkyl)$_2$, $C_3$-cycloalkyl, heterocyclyl, aryl, or heteroaryl.

The term "aryl" refers to carbocyclic aromatic groups having from 6 to 10 carbon atoms ('$C_{6-10}$") such as phenyl, naphthyl, and the like. An aryl is optionally substituted with one, two, or three substituents selected from halo (F, $C_1$, Br, or I, preferably F), —OH, —$OC_{1-6}$alkyl, —CN, —$NH_2$, —NH($C_{1-6}$alkyl), —NH($C_{1-6}$alkyl)$_2$, $C_3$-cycloalkyl, heterocyclyl, aryl, or heteroaryl. In some embodiments, the aryl is substituted with one halo. In other embodiments, the aryl is substituted with one F. In further embodiments, the aryl is substituted with one $^{18}$F. In still other embodiments, the aryl is phenyl and is optionally substituted with one halo. In yet further embodiments, the aryl is phenyl and is optionally substituted with one F. In other embodiments, the aryl is phenyl and is optionally substituted with one $^{18}$F.

"Heteroaryl" refers to a 5- to 18-membered aromatic radical, e.g., $C_{5-18}$heteroaryl, that includes one or more ring heteroatoms selected from nitrogen, oxygen and sulfur, and which may be a monocyclic, bicyclic, tricyclic or tetracyclic ring system. Whenever it appears herein, a numerical range such as "5 to 18" refers to each integer in the given range, e.g., "5 to 18 ring atoms" means that the heteroaryl group may contain 5 ring atoms, 6 ring atoms, etc., up to and including 18 ring atoms. An N-containing heteroaryl moiety refers to an aromatic group in which at least one of the skeletal atoms of the ring is a nitrogen atom. The polycyclic heteroaryl group may be fused or non-fused. The heteroatom(s) in the heteroaryl radical are optionally oxidized. One or more nitrogen atoms, if present, are optionally quaternized. The heteroaryl may be attached to the rest of the molecule through any atom of the ring(s). Examples of heteroaryls include, but are not limited to, azepinyl, acridinyl, benzimidazolyl, benzindolyl, 1,3-benzodioxolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzodioxolyl, benzodioxinyl, benzoxazolyl, benzopyranyl, benzopyranonyl, benzofuranyl, benzofuranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pyridinyl, and thiophenyl (i.e. thienyl). A heteroaryl is optionally substituted with one, two, or three substituents selected from halo (F, Cl, Br, or I, preferably F), —OH, —OC$_{1-6}$alkyl, —CN, —NH$_2$, —NH(C$_{1-6}$alkyl), —NH(C$_{1-6}$alkyl)$_2$, C$_3$-cycloalkyl, heterocyclyl, aryl, or heteroaryl.

When a range of carbon atoms is used herein, for example, C$_{1-6}$, all ranges, as well as individual numbers of carbon atoms are encompassed. For example, "C$_{1-3}$" includes C$_{1-3}$, C$_{1-2}$, C$_{2-3}$, C$_1$, C$_2$, and C$_3$.

The terms "halogen" and "halo" represent chlorine, fluorine, bromine, or iodine. The term "halo" represents chloro, fluoro, bromo, or iodo. When present in the compounds described herein, one or more halogen atom may be radiolabeled. In some embodiments, any $^{19}$F atom may be substituted with a $^{18}$F atom. In other embodiments, any $^{127}$I may be substituted with $^{123}$I. In further embodiments, any $^{127}$I may be substituted with $^{124}$I. In yet further embodiments, any $^{127}$ may be substituted with $^{125}$. In still other embodiments, any $^{127}$I may be substituted with $^{131}$I. In other embodiments, any $^8$Br may be substituted with $^{76}$Br). In further embodiments, any $^{80}$Br may be substituted with $^{77}$Br.

As used herein, the term "compound(s) of formula (I)" includes those compounds of "formula (I)," as well as compounds of any of the formula (I) subgenera. The term "compound(s) of formula (II)" includes those compounds of "formula (II)," as well as compounds of any of the formula (II) subgenera.

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

The terms "patient" or "subject" as used herein refer to a mammalian animal and are used interchangeably. In some embodiments, the patient or subject is a human. In other embodiments, the patient or subject is a veterinary or farm animal, a domestic animal or pet, or animal normally used for clinical research.

"Treating" any disease or disorder refers, in some embodiments, to ameliorating the disease or disorder (i.e., arresting or reducing the development of the disease or at least one of the clinical symptoms thereof). In some embodiments, "treating" or "treatment" refers to ameliorating at least one physical parameter, which may not be discernible by the subject. In other embodiments, "treating" or "treatment" refers to modulating the disease or disorder, either physically, (e.g., stabilization of a discernible symptom), physiologically, (e.g., stabilization of a physical parameter), or both. In further embodiments, "treating" or "treatment" refers to delaying the onset of the disease or disorder.

"Compounds of the present disclosure," and equivalent expressions, are meant to embrace compounds of the Formulae (I) and (II) as described herein, which expression includes the pharmaceutically acceptable salts, where the context so permits. Similarly, reference to intermediates, whether or not they themselves are claimed, is meant to embrace their salts, and solvates, where the context so permits.

As used herein, the term "isotopic variant" refers to a compound that contains unnatural proportions of isotopes at one or more of the atoms that constitute such compound. In some embodiments, an "isotopic variant" of a compound can be radiolabeled, that is, contain one or more non-radioactive isotopes and/or one or more radioactive isotopes. It will be understood that, in a compound where such isotopic substitution is made, the following atoms, where present, may vary, so that for example, any hydrogen may be 2H/D, any carbon may be $^{13}$C, or any nitrogen may be $^{15}$N, and that the presence and placement of such atoms may be determined within the skill of the art. In other embodiments, the compounds are radiolabeled with a non-radioactive isotope such as for example, deuterium ($^2$H or D), carbon-13 ($^{13}$C), nitrogen-15 ($^{15}$N), or the like. In other embodiments, the compounds are, additionally or alternatively, labeled with radioactive isotopes. In some embodiments, the radioactive isotopes emit electrons, alpha (a), gamma (γ) or beta (β$^-$ or ) particles. Radioactive labels include, without limitation, tritium (3H), carbon-11 ($^{11}$C), carbon-14 ($^{14}$C), fluorine-18 ($^{18}$F), iodine-123 ($^{123}$I), iodine-124 ($^{124}$I), iodine-125 ($^{125}$I), iodine-131 ($^{131}$I) bromine-76 ($^{76}$Br), bromine-77 ($^{77}$Br), oxygen-15($^{15}$O), nitrogen-13 ($^{13}$N), or astatine-211 ($^{211}$At) or combinations thereof. Thus, radiolabeled compounds of the disclosure can be used in diagnostic methods such imaging. Imaging methods include, without limitation, single-photon emission computed tomography (SPECT) or Positron Emission Topography (PET) studies. In some embodiments, the radiolabel is $^3$H or $^{14}$C. In further embodiments, the compound is radiolabeled with $^3$H, $^{14}$C, and/or $^{123}$I and may be used in SPECT. In other embodiments, the compound is radiolabeled with a β$^+$ emitting isotopes, such as $^{11}$C, $^{18}$F, $^{15}$O $^{13}$N, $^{124}$, or $^{76}$Br and may be useful in PET. In further embodiments, the compounds may be radiolabeled with electron emitting isotopes, such as $^{123}$I, or $^{77}$Br. In yet other embodiments, the compounds are radiolabeled with alpha particle emitting radiolabels such as $^{211}$At. In still further embodiments, the compounds are radiolabeled with β$^-$ emitting isotopes such as $^{131}$I.

All isotopic variants of the compounds of the disclosure, radioactive or not, are intended to be encompassed within the scope of the disclosure.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers," for example, diastereomers, enantiomers, and atropisomers. The compounds of this disclosure may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. Within the present disclosure, any open valency appearing on a carbon, oxygen, or nitrogen atom in any structure described herein indicates the presence of a hydrogen atom. Where a chiral center exists in a structure, but no specific stereochemistry is shown for that center, both enantiomers, separately or as a mixture, are encompassed by that structure. The methods for the determination of stereochemistry and the separation of stereoisomers are well-known in the art.

This invention describes the synthesis and use of novel compounds. Thus, the present disclosure provides compound of Formula I or II, or a pharmaceutically acceptable salt, stereoisomer, or isotopic variant thereof. In some embodiments, the disclosure provides a pharmaceutically acceptable salt of the compound of Formula I or II. In other embodiments, the disclosure provides stereoisomers of the compound of Formula I or II. In still further embodiments, the disclosure provides isotopic variants of the compound of Formula I or II.

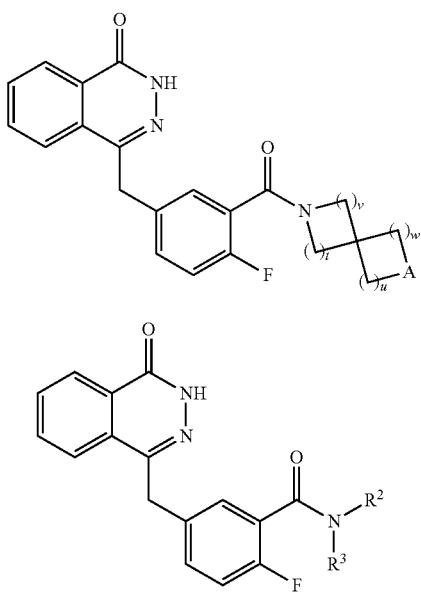

In some embodiments, the compound is of formula I.

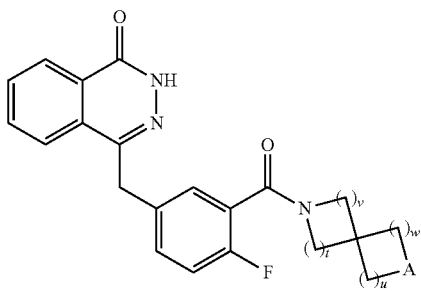

In the con pounds of formula I, A is $NR^1$, CR, or O. In some embodiments, A is $NR^1$. In other embodiments, A is $CHR^1$. In further embodiments, A is O.

When A is $NR^1$ or $CHR^1$, $R^1$ is H, alkoxy, aryl, —C(O)(aryl), —C(O)(cycloalkyl), or —C(O)(alkoxy). In some embodiments, $R^1$ is H. In other embodiments, $R^1$ is alkoxy. In further embodiments, $R^1$ is fluorinated methoxy, fluorinated ethoxy, fluorinated propoxy, fluorinated butoxy, fluorinated pentoxy, or fluorinated hexoxy.

In yet further embodiments, $R^1$ is —C(O)(aryl). In still other embodiments, $R^1$ is —C(O)(substituted phenyl). In yet other embodiments, $R^1$ is —C(O)(phenyl) substituted with 1 or 2 substituents that are, independently, halo or heterocyclyl, such as $^{18}F$, $^{19}F$, $^{123}I$, $^{124}I$, $^{125}I$, $^{131}I$, $^{76}Br$, $^{77}Br$, or $^{211}At$ or boronic acid pinocol ester.

In yet other embodiments, $R^1$ is —C(O)(cycloalkyl). In still further embodiments, $R^1$ is C(O)(cyclopropyl), —C(O)(cyclobutyl), —C(O)(cyclopentyl), or —C(O)(cyclohexyl). In other embodiments, $R^1$ is —C(O)(cyclopropyl). In still further embodiments, $R^1$ is —C(O)(alkoxy). In further embodiments, $R^1$ is C(O)methoxy, C(O)ethoxy, C(O)propoxy, C(O)butoxy, or C(O)pentoxy. In still other embodiments, $R^1$ is C(O)butoxy.

In further embodiments, $R^1$ is aryl. In yet other embodiments, $R^1$ is substituted phenyl. In still further embodiments, $R^1$ is phenyl substituted with 1 or 2 substituents that are, independently, halo or heterocyclyl, such as $^{18}F$, $^{19}F$, $^{123}I$, $^{124}I$, $^{125}I$, $^{131}I$, $^{76}Br$, $^{77}Br$, $^{211}At$ or a boronic acid pinocol ester.

The rings bound to the carbonyl moiety of the compounds of formula I may vary in size. In some embodiments, t is 1, 2, or 3. In other embodiments, t is 1. In further embodiments, t is 2. In yet other embodiments, t is 3. In some embodiments, u is 1 or 2. In other embodiments, u is 1. In further embodiments, u is 2. In some embodiments, v is 0, 1, 2, or 3. In other embodiments, v is 0. In further embodiments, v is 1. In yet other embodiments, v is 2. In still further embodiments, v is 3. In some embodiments, w is 1 or 2. In other embodiments, w is 1. In further embodiments, w is 2. In yet other embodiments, t, u, v, and w are 1. In still further embodiments, t is 2, v is 0, and u and w are 1. In other embodiments, t, u, and w is 1 and v is 2. In further embodiments, t and v are 1, u and w are 2. In still other embodiments, t, u, and w are 2 and v is 0. In yet other embodiments, t is 2, v is 1, u is 1 and w is 1. In other embodiments, t is 2, v is 1, u is 2, and w is 1. In further embodiments, t is 2, v is 1, u is 2, and w is 2. In yet other embodiments, t and u are 1, and v and w are 2. In still further embodiments, t is 1 and v, u, and are 2. In other embodiments, t, v, u, and w are 2.

In some embodiments, the compounds are of formula IA, IB, IC, ID, IE, IF, or IG:

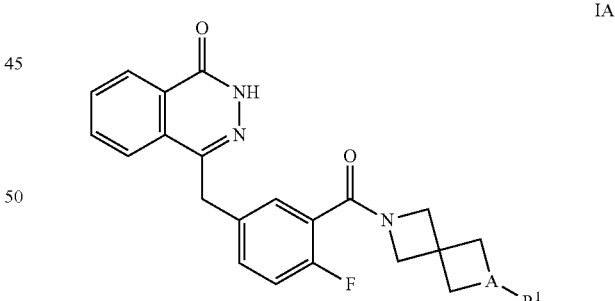

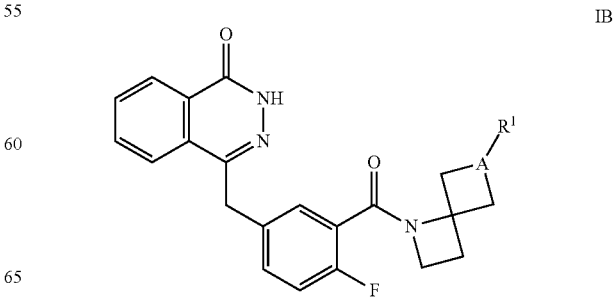

IC
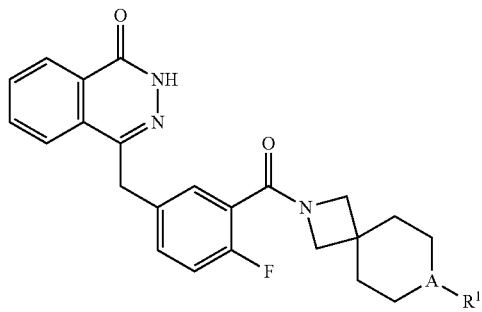

ID
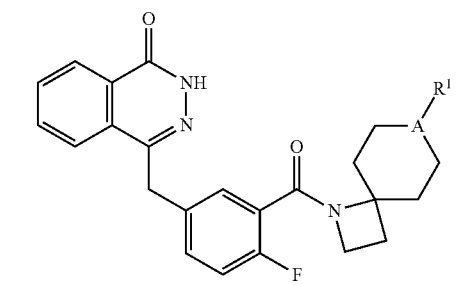

IE
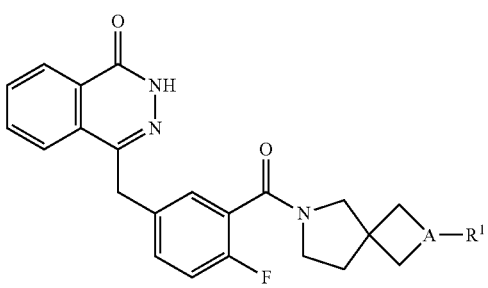

IF
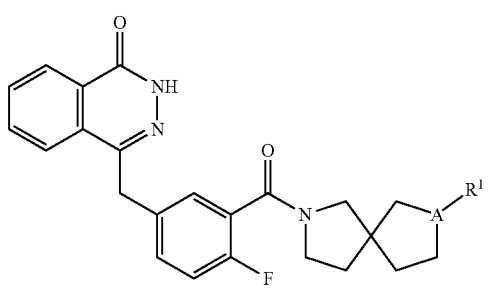

IG
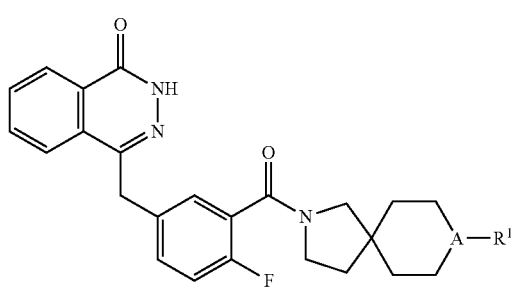

IH
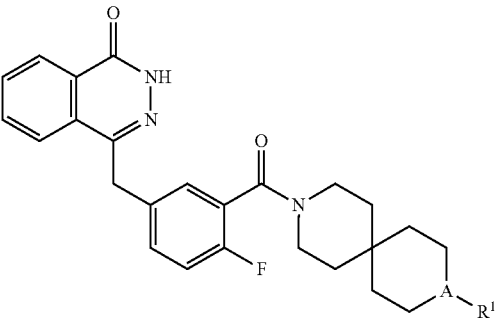

In other embodiments, the compound is of formula II.

II
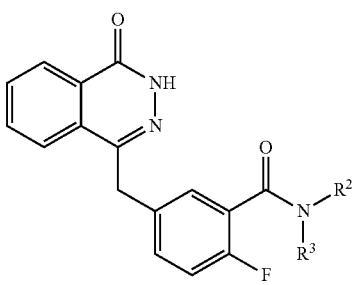

In compounds of formula II, $R^2$ is H and $R^3$ is cycloalkyl. In some embodiments, $R^3$ is cyclobutyl, cyclopentyl, or cyclohexyl. In other embodiments, $R^3$ is a cycloalkyl substituted by 1 or 2 substituents that are, independently, $C_{1-6}$alkoxy or $C_{1-6}$haloalkoxy.

Alternatively, $R^2$ and $R^3$ combine to form a heterocycle. In further embodiments, $R^2$ and $R^3$ combine to form a heterocyclyl containing 1 or 2 nitrogen atoms. In other embodiments, $R^2$ and $R^3$ combine to form azetidinyl, pyrrolidinyl, piperidinyl, piperazinyl, or azepanyl. In other embodiments, $R^2$ and $R^3$ combine to form a heterocyclyl that is substituted by one or two substituents that are independently $C_{1-6}$alkoxy. In further embodiments, $R^2$ and $R^3$ combine to form a heterocyclyl that is substituted by one or two methoxy, ethoxy, propoxy, butoxy, pentoxy, or hexoxy. In further embodiments, $R^2$ and $R^3$ combine to form a heterocyclyl that is substituted by one or two substituents that are independently $C_{1-6}$haloalkoxy. In still other embodiments, $R^2$ and $R^3$ combine to form a heterocyclyl that is substituted by one or two fluorinated methoxy, fluorinated ethoxy, fluorinated propoxy, fluorinated butoxy, fluorinated pentoxy, or fluorinated hexoxy. In yet other embodiments, $R^2$ and $R^3$ combine to form a heterocyclyl that is substituted by one or two substituents that are independently substituted phenyl. In still further embodiments, $R^2$ and $R^3$ combine to form a heterocyclyl that is substituted with a phenyl that is substituted with halo or heterocyclyl, such as $^{18}F$, $^{19}F$, $^{123}I$, $^{124}I$, $^{125}I$, $^{131}I$, $^{76}Br$, $^{77}Br$, or $^{211}At$ or boronic acid pinocol ester.

In further embodiments, the compound of formula II is of formula IIA or IIB.

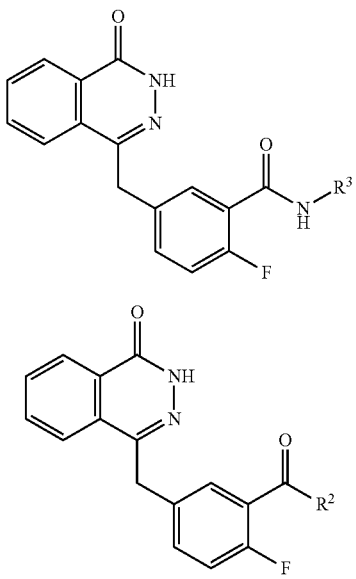

The compounds discussed above may encompass tautomeric forms of the structures provided herein characterized by the bioactivity of the drawn structures. Further, the compounds may also be used in the form of salts derived from pharmaceutically or physiologically acceptable acids, bases, alkali metals and alkaline earth metals.

In some embodiments, pharmaceutically acceptable salts can be formed from organic and inorganic acids including, e.g., acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, camphorsulfonic, and similarly known acceptable acids.

In other embodiments, pharmaceutically acceptable salts may also be formed from inorganic bases, desirably alkali metal salts including, e.g., sodium, lithium, or potassium, such as alkali metal hydroxides. Examples of inorganic bases include, without limitation, sodium hydroxide, potassium hydroxide, calcium hydroxide, and magnesium hydroxide. Pharmaceutically acceptable salts may also be formed from organic bases, such as ammonium salts, mono-, di-, and trimethylammonium, mono-, di- and triethylammonium, mono-, di- and tripropylammonium, ethyldimethylammonium, benzyldimethylammonium, cyclohexylammonium, benzyl-ammonium, dibenzylammonium, piperidinium, morpholinium, pyrrolidinium, piperazinium, 1-methylpiperidinium,4-ethylmorpholinium,1-isopropylpyrrolidinium,1,4-dimethylpiperazinium, 1 n-butyl piperidinium, 2-methylpiperidinium, 1-ethyl-2-methylpiperidinium, mono-, di- and triethanolammonium, ethyl diethanolammonium, n-butylmonoethanolammonium, tris(hydroxymethyl)methylammonium, phenylmono-ethanolammonium, diethanolamine, ethylenediamine, and the like. In one example, the base is selected from among sodium hydroxide, lithium hydroxide, potassium hydroxide, and mixtures thereof.

The disclosure also provides pharmaceutical compositions that contain a compound discussed herein in a pharmaceutically acceptable excipient. The term "pharmaceutically acceptable excipient" as used herein refers to an excipient that is stable and compatible with a patient. In some embodiments, a compound described above is combined with one or more pharmaceutically acceptable excipients and/or other therapeutic agents as described below.

The pharmaceutical compositions include a compound described herein formulated neat or with one or more pharmaceutically acceptable excipients for administration, the proportion of which is determined by the solubility and chemical nature of the compound, chosen route of administration and standard pharmacological practice. The pharmaceutically acceptable excipient may be solid or liquid.

The compound may be administered to a subject by any desirable route, taking into consideration the specific condition for which it has been selected. The compound may, therefore, be delivered orally, by injection, i.e., transdermally, intravenously, subcutaneously, intramuscularly, intravenous, intra-arterial, intraperitoneal, intracavitary, or epiduraly, among others.

Although the compound may be administered alone, it may also be administered in the presence of one or more pharmaceutically acceptable excipient that are physiologically compatible. In some embodiments, the pharmaceutically acceptable excipient is a carrier.

The carrier may be in dry or liquid form and must be pharmaceutically acceptable. Liquid pharmaceutical compositions are typically sterile solutions or suspensions. When liquid carriers are utilized, they are desirably sterile liquids. Liquid carriers are typically utilized in preparing solutions, suspensions, emulsions, syrups and elixirs. In one embodiment, the compound is dissolved a liquid carrier. In some embodiments, the compound is suspended in a liquid carrier. One of skill in the art of formulations would be able to select a suitable liquid carrier, depending on the route of administration. In one embodiment, the liquid carrier includes, without limitation, water, organic solvents, oils, fats, or mixtures thereof. In other embodiments, the liquid carrier is water containing cellulose derivatives such as sodium carboxymethyl cellulose. In further embodiments, the liquid carrier is water and/or dimethylsulfoxide. Examples of organic solvents include, without limitation, alcohols such as monohydric alcohols and polyhydric alcohols, e.g., glycols and their derivatives, among others. Examples of oils include, without limitation, fractionated coconut oil, arachis oil, corn oil, peanut oil, and sesame oil and oily esters such as ethyl oleate and isopropyl myristate.

Alternatively, the compound may be formulated in a solid carrier. In some embodiments, the composition may be compacted into a unit dose form, i.e., tablet or caplet. In other embodiments, the composition may be added to unit dose form, i.e., a capsule. In further embodiments, the composition may be formulated for administration as a powder. The solid carrier may perform a variety of functions, i.e., may perform the functions of two or more of the pharmaceutically acceptable excipients described below. For example, the solid carrier may also act as a flavoring agent, lubricant, solubilizer, suspending agent, filler, glidant, compression aid, binder, disintegrant, or encapsulating material. Suitable solid carriers include, without limitation, calcium phosphate, dicalcium phosphate, magnesium stearate, talc, starch, sugars (including, e.g., lactose and sucrose), cellulose (including, e.g., microcrystalline cellulose, methyl cellulose, sodium carboxymethyl cellulose), polyvinylpyrrolidine, low melting waxes, ion exchange resins, and kaolin. The solid carrier can contain other suitable pharmaceutically acceptable excipients, including those described below.

Examples of pharmaceutically acceptable excipients which may be combined with the compound include, without limitation, adjuvants, antioxidants, binders, buffers, coatings, coloring agents, compression aids, diluents, disintegrants, emulsifiers, emollients, encapsulating materials, fillers, flavoring agents, glidants, granulating agents, lubricants, metal chelators, osmo-regulators, pH adjustors, preservatives, solubilizers, sorbents, stabilizers, sweeteners, surfactants, suspending agents, syrups, thickening agents, or viscosity regulators. See, the excipients described in the "Handbook of Pharmaceutical Excipients", 5$^{th}$ Edition, Eds.: Rowe, Sheskey, and Owen, APhA Publications (Washington, D.C.), Dec. 14, 2005, which is incorporated herein by reference.

The pharmaceutical composition described herein may be prepared by those skilled in the art. In some embodiments, the pharmaceutical compositions are prepared by combining a compound described herein with a pharmaceutically acceptable excipient.

As noted above, the compounds herein target the poly (ADP-ribose)polymerase-1 (PARP-1) enzyme. Thus, these compounds have use in treating poly(ADP-ribose)polymerase-1-mediated diseases or disorders in a subject.

These compounds are useful in treating neurodegenerative diseases. In some embodiments, the compounds are useful in treating neurodegenerative diseases including, but not limited to, Alzheimer's disease, Parkinson's disease, and Huntington's disease. In other embodiments, the compounds are useful in treating Alzheimer's disease. In further embodiments, the compounds are useful in treating Parkinson's disease. In yet other embodiments, the compounds are useful in treating Huntington's disease.

The compounds are also useful for treating cancer. The term "cancer" as used herein, refers to neoplastic cells in a patient which have abnormal cell group and invade or have the potential to invade one or more body parts of the patient. In some embodiments, the cancer is breast cancer, uterine cancer, lung cancer, ovarian cancer, and skin cancer, or non-Hodgkin's lymphoma. In other embodiments, the cancer is breast cancer. In further embodiments, the cancer is uterine cancer. In other embodiments, the cancer is lung cancer. In yet other embodiments, the cancer is ovarian cancer. In still further embodiments, the cancer is skin cancer. In other embodiments, the cancer is non-Hodgkin's lymphoma.

The compounds may also be used in detecting a poly (ADP-ribose)polymerase-1-mediated disease or disorder. Thus, these methods include administering an effective amount of the compound to a subject and detecting the disease or disorder. The disease or disorder may be detected by performing imaging such as positron emission tomography or single photon emission computed tomography. In some embodiments, the detection methods described herein may be performed using an isotopically-labeled compound described herein. In other embodiments, the compounds are useful in detecting a neurodegenerative disease or disorder.

The compounds also have properties that permit brain penetration while retaining high affinity to the PARP-1 enzyme. Thus, these compounds are also useful in imaging PARP-1 and the therapeutic targeting of PARP-1 to inhibit PARylation and prevent PARP-1 mediated neurodegeneration. In some embodiments, the compounds are high affinity, non-cytotoxic, brain penetrant PARP inhibitors.

In some embodiments, the compounds are PET diagnostic agents that can determine PARP-1 expression in a patient's tumor and directly measure the drug target engagement of PARP inhibitors offering a pharmacodynamic measure of therapy. Thus, these compounds improve PARP inhibitor therapy over conventional screening methods currently used in the clinic which rely on secondary biomarkers that are imperfect. In further compounds, the compounds permit the delivery of cytotoxic radionuclides directly to cancer chromatin greatly improving the therapeutic effects of high linear energy transfer radiation like alpha particles and Auger electrons that can treat micrometastatic disease where conventional PARP inhibitors will be ineffective. In still other embodiments, the compounds are useful for treating bulky diseases that require the use of beta emitting radionuclides that are more effective at treating bulky disease. In further embodiments, the compounds are high affinity, cytotoxic, brain penetrant or non-penetrant compounds. In other embodiments, the compounds with high affinity can be functionalized with therapeutic radionuclides and fall within this scope.

The compounds are also useful in sensitizing a cancer to treatment with a chemotherapeutic. In doing so, the compounds weaken some or all of the cancer cells to apoptosis by another chemotherapeutic agent or radiation. Alternatively, the compounds kill some of the cancer cells and a second chemotherapeutic or radiation may be utilized to kill the remaining cancer cells.

Also provided herein are methods of monitoring cancer treatment in a subject by administering a chemotherapeutic or radiation to the subject, administering an effective amount of an isotopically-labeled compound to said subject, and performing positron emission tomography or single photon emission computed tomography on the subject.

In some embodiments, an effective amount of a pharmaceutical agent according to the disclosure is administered to a subject suffering from or diagnosed as having such a disease, disorder, or condition. An "effective amount" means an amount or dose sufficient to generally bring about the desired therapeutic benefit in patients in need of such treatment for the designated disease, disorder, or condition. Effective amounts or doses of the compounds of the present disclosure may be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician. An example of a dose is in the range of from about 0.001 to about 200 mg of compound per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 0.2 to about 2.5 g/day.

In other embodiments, a therapeutically or prophylactically effective amount of a radiolabeled compound is that amount of a compound which provides a sufficient amount of radiation. The sufficient amount of radiation may vary depending upon the formulation and route of delivery. In some embodiments, the amount (i.e., per unit) of the compound is that which does not exceed normal organ dose limits and delivers a tumoricidal dose to cancer cells. In other embodiments, the dose of the compound is dependent on the specific organ and cancer being treated. In further embodiments, the dose of the compound is the maximum dose tolerated by the patient. In yet other embodiments, the compound delivers about 0.01 to about 100 mCi of radiation. In still further embodiments, the compound delivers about 0.05 to about 75 mCi of radiation. In other embodiments, the compound delivers about 0.1 to about 30 mCi of radiation. However, the effective amount to be used is subjectively determined by the attending physician and variables such as the size, age and response pattern of the patient.

These effective amounts may be provided on regular schedule, i.e., daily, weekly, monthly, or yearly basis or on an irregular schedule with varying administration days, weeks, months, etc. Alternatively, the effective amount to be administered may vary. In some embodiments, the effective amount for the first dose is higher than the effective amount for one or more of the subsequent doses. In other embodiments, the effective amount for the first dose is lower than the effective amount for one or more of the subsequent doses.

The methods described herein may be performed by administering a compound described herein via a combination therapy in prior to, concurrently with, or subsequent to another medication such as a chemotherapeutic. Such combination treatment may occur by administering compositions containing multiple active ingredients, as described above. However, also encompassed are methods of administering chemotherapeutics in conjunction with a composition containing a compound described herein. In some embodiments, the compound and chemotherapeutic are administered to the patient by one or more selected routes of administration sequentially. In other embodiments, a chemotherapeutic agent is administered before treatment with a compound described herein. In further embodiments, a chemotherapeutic agent is administered after treatment with a compound described herein. In still other embodiments, a chemotherapeutic agent is administered during treatment with a compound described herein.

In yet further embodiments, methods of administering radiotherapy to a patient in need thereof is provided and includes administering a compound or composition to the patient.

In some aspects, methods of treating a poly(ADP-ribose)polymerase-1-mediated disease or disorder in a subject are provided and comprise administering to the subject a therapeutically effective amount of a compound described herein or a pharmaceutically acceptable salt thereof.

In other aspects, methods of detecting a poly(ADP-ribose)polymerase-1-mediated neurodegenerative disease or disorder in a subject are provided and comprise (a) administering an effective amount of an isotopically-labeled compound described herein to a subject; and (b) performing positron emission tomography or single photon emission computed tomography on said subject.

In further aspects, methods of monitoring cancer treatment in a subject are provided and comprise (a) administering a chemotherapeutic or radiation to said subject, (b) administering an effective amount of an isotopically-labeled compound described herein to said subject, and (c) performing positron emission tomography or single photon emission computed tomography on said subject.

In yet other aspect, methods of detecting a poly(ADP-ribose)polymerase-1-mediated cancer in a subject are provided and comprise (a) administering an effective amount of a compound of described herein to the subject and (b) performing positron emission tomography or single photon emission computed tomography on the subject.

Also provided herein are kits or packages containing a compound or composition described herein. The kits may be organized to indicate a single formulation or combination of formulations to be taken at each desired time. The composition may also be sub-divided to contain appropriate quantities of the compound. For example, the unit dosage can be packaged compositions, e.g., packeted powders, vials, ampoules, prefilled syringes or sachets containing liquids.

Suitably, the kit contains packaging or a container with the compound formulated for the desired delivery route. Suitably, the kit contains instructions on dosing and an insert regarding the compound. Optionally, the kit may further contain instructions for monitoring circulating levels of product and materials for performing such assays including, e.g., reagents, well plates, containers, markers or labels, and the like. Such kits are readily packaged in a manner suitable for treatment of a desired indication. For example, the kit may also contain instructions for use of the delivery device. Other suitable components to include in such kits will be readily apparent to one of skill in the art, taking into consideration the desired indication and the delivery route. The doses are repeated daily, weekly, or monthly, for a predetermined length of time or as prescribed.

The compound or composition described herein can be a single dose or for continuous or periodic discontinuous administration. For continuous administration, a package or kit can include the compound in each dosage unit (e.g., solution, lotion, tablet, pill, or other unit described above or utilized in drug delivery). When the compound is to be delivered with periodic discontinuation, a package or kit can include placebos during periods when the compound is not delivered. When varying concentrations of a composition, of the components of the composition, or of relative ratios of the compound or other agents within a composition over time is desired, a package or kit may contain a sequence of dosage units, so varying.

A number of packages or kits are known in the art for the use in dispensing pharmaceutical agents for oral use. In one embodiment, the package has indicators for each period. In another embodiment, the package is a labeled blister package, dial dispenser package, or bottle.

The packaging means of a kit may itself be geared for administration, such as an inhalant, syringe, pipette, eye dropper, or other such like apparatus, from which the formulation may be applied to an infected area of the body, such as the lungs, injected into a subject, or even applied to and mixed with the other components of the kit.

The compound or composition of these kits also may be provided in dried or lyophilized forms. When reagents or components are provided as a dried form, reconstitution generally is by the addition of a suitable solvent. It is envisioned that the solvent also may be provided in another packaging means.

The kits may include a means for containing the vials in close confinement for commercial sale such as, e.g., injection or blow-molded plastic containers into which the desired vials are retained.

Irrespective of the number or type of packages, the kits also may include, or be packaged with a separate instrument for assisting with the injection/administration or placement of the ultimate complex composition within the body of an animal. Such an instrument may be an inhalant, syringe, pipette, forceps, measuring spoon, eye dropper or any such medically approved delivery means. Other instrumentation includes devices that permit the reading or monitoring of reactions in vitro.

In one embodiment, a pharmaceutical kit is provided and contains a compound as described herein. The compound may be in the presence or absence of one or more of the pharmaceutically acceptable excipients described above. The kit may optionally contain a chemotherapeutic and/or instructions for administering the chemotherapeutic and the compound to a subject having cancer.

In a further embodiment, a pharmaceutical kit is provided and contains a chemotherapeutic in a first dosage unit, one or more of a compound selected from those described herein in a second dosage unit, and one or more of the pharmaceutically acceptable excipients described above in a third dosage unit. The kit may optionally contain instructions for administering the chemotherapeutic and/or compound to a subject having cancer.

The following Examples are provided to illustrate some of the concepts described within this disclosure. While each Example is considered to provide specific individual embodiments of composition, methods of preparation and use, none of the Examples should be considered to limit the more general embodiments described herein.

In the following examples, efforts have been made to ensure accuracy with respect to numbers used (e.g. amounts, temperature, etc.) but some experimental error and deviation should be accounted for. Unless indicated otherwise, temperature is in degrees C., pressure is at or near atmospheric.

Aspects

Aspect 1: A compound of Formula I or II, or a pharmaceutically acceptable salt thereof:

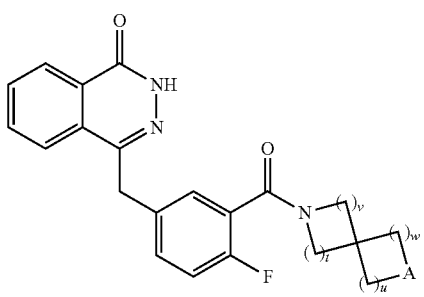

I

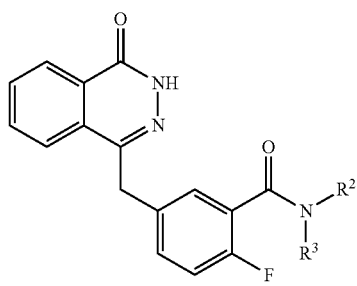

II wherein:
A is $NR^1$, $CHR^1$, or O;
$R^1$ is H, alkoxy, aryl, —C(O)(aryl), —C(O)(cycloalkyl), or —C(O)(alkoxy);
$R^2$ is H and $R^3$ is cycloalkyl; or $R^2$ and $R^3$ combine to form a heterocycle;
t is 1, 2, or 3;
u is 1 or 2;
v is 0, 1, 2, or 3; and
w is 1 or 2;
or an isotopic variant thereof;
or a stereoisomer thereof, or a mixture thereof.

Aspect 2: The compound of aspect 1, which is a compound of Formula I.

Aspect 3: The compound of aspect 1 or 2, wherein A is $NR^1$.

Aspect 4: The compound of aspect 1 or 2, wherein A is $CHR^1$.

Aspect 5: The compound of aspect 1 or 2, wherein A is O.

Aspect 6: The compound of any one of aspects 1-4, wherein $R^1$ is H.

Aspect 7: The compound of any one of aspects 1-4, wherein $R^1$ is —C(O)(alkoxy) such as C(O)methoxy, C(O)ethoxy, C(O)propoxy, C(O)butoxy, or C(O)pentoxy, preferably C(O)butoxy.

Aspect 8: The compound of any one of aspects 1-4, wherein $R^1$ is —C(O)(cycloalkyl) such as C(O)(cyclopropyl), —C(O)(cyclobutyl), —C(O)(cyclopentyl), or —C(O)(cyclohexyl), preferably —C(O)(cyclopropyl).

Aspect 9: The compound of any one of aspects 1-4, wherein $R^1$ is aryl such as substituted phenyl.

Aspect 10: The compound of aspect 9, wherein $R^1$ is phenyl substituted with 1 or 2 substituents that are, independently, halo or heterocyclyl, such as $^{18}F$, $^{19}F$, $^{123}I$, $^{124}I$, $^{125}I$, $^{131}I$, $^{76}Br$, $^{77}Br$, $^{211}At$ or a boronic acid pinocol ester.

Aspect 11: The compound of any one of aspects 1-4, wherein $R^1$ is —C(O)(aryl) such as —C(O)(substituted phenyl).

Aspect 12: The compound of aspect 11, wherein $R^1$ is —C(O)(phenyl) substituted with 1 or 2 substituents that are, independently, halo or heterocyclyl, such as $^{18}F$, $^{19}F$, $^{123}I$, $^{124}I$, $^{125}I$, $^{131}I$, $^{76}Br$, $^{77}Br$, or $^{211}At$ or boronic acid pinocol ester.

Aspect 13: The compound of any one of aspects 1-4, wherein $R^1$ is alkoxy such as fluorinated methoxy, fluorinated ethoxy, fluorinated propoxy, fluorinated butoxy, fluorinated pentoxy, or fluorinated hexoxy.

Aspect 14: The compound of aspect 1, which is a compound of Formula II.

Aspect 15: The compound of aspect 1 or 14, wherein $R^2$ is H and $R^3$ is a cycloalkyl such as cyclobutyl, cyclopentyl, or cyclohexyl.

Aspect 16: The compound of aspect 1 or 15, wherein $R^3$ is a cycloalkyl substituted by 1 or 2 substituents that are, independently, $C_{1-6}$alkoxy or $C_{1-6}$haloalkoxy.

Aspect 17: The compound of aspect 1 or 14, wherein $R^2$ and $R^3$ combine to form a heterocyclyl, preferably a heterocyclyl containing 1 or 2 nitrogen atoms, such as azetidinyl, pyrrolidinyl, piperidinyl, piperazinyl, or azepanyl.

Aspect 18: The compound of aspect 1 or 17, wherein the heterocyclyl is substituted by one or two substituents that are independently $C_{1-6}$alkoxy such as methoxy, ethoxy, propoxy, butoxy, pentoxy, or hexoxy.

Aspect 19: The compound of claim 1 or 17, wherein the heterocyclyl is substituted by one or two substituents that are independently $C_{1-6}$haloalkoxy such as fluorinated methoxy, fluorinated ethoxy, fluorinated propoxy, fluorinated butoxy, fluorinated pentoxy, or fluorinated hexoxy.

Aspect 20: The compound of aspect 1 or 17, wherein the heterocyclyl is substituted by one or two substituents that are independently substituted phenyl.

Aspect 21: The compound of aspect 20, wherein the phenyl is substituted with halo or heterocyclyl, such as $^{18}F$, $^{19}F$, $^{123}I$, $^{124}I$, $^{125}I$, $^{131}I$, $^{76}Br$, $^{77}Br$, or $^{211}At$ or boronic acid pinocol ester.

Aspect 22: The compound of any one of the preceding aspects, wherein t, u, v, and w are 1.

Aspect 23: The compound of any one of aspects 1 to 21, wherein t is 2, v is 0, and u and w are 1.

Aspect 24: The compound of any one of aspects 1 to 21, wherein t, u, and w is 1 and v is 2.

Aspect 25: The compound of any one of aspects 1 to 21, wherein t and v are 1, u and w are 2.

Aspect 26: The compound of any one of aspects 1 to 21, wherein t, u, and w are 2 and v is 0.

Aspect 27: The compound of any one of aspects 1 to 21, wherein t is 2, v is 1, u is 1 and w is 1.

Aspect 28: The compound of any one of aspects 1 to 21, wherein t is 2, v is 1, u is 2, and w is 1.

Aspect 29: The compound of any one of aspects 1 to 21, wherein t is 2, v is 1, u is 2, and w is 2.

Aspect 30: The compound of any one of aspects 1 to 21, wherein t and u are 1, and v and w are 2.

Aspect 31: The compound of any one of aspects 1 to 21, wherein t is 1 and v, u, and are 2.

Aspect 32: The compound of any one of aspects 1 to 21, wherein t, v, u, and w are 2.

Aspect 33: The compound of aspect 1, or a pharmaceutically acceptable salt thereof, of the formula:

(IA)
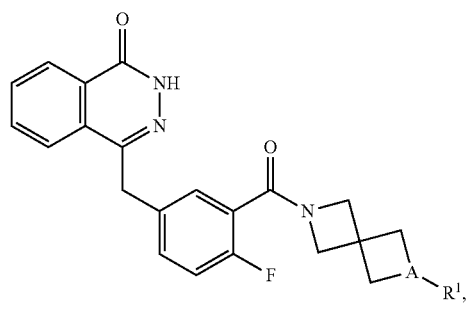

(IB)
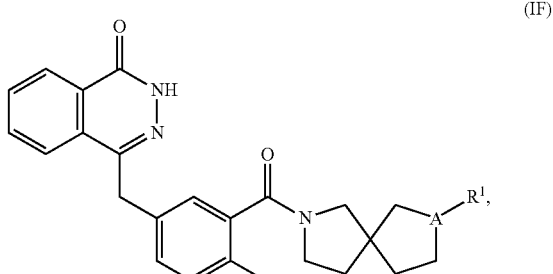

(IC)
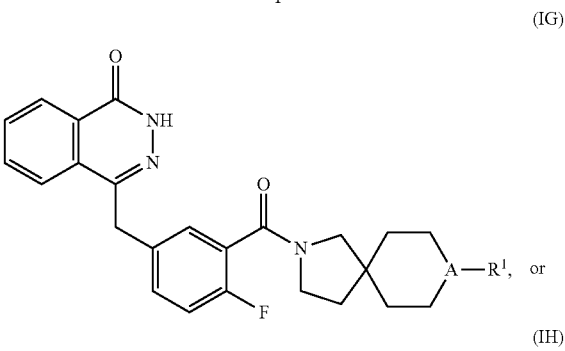

(ID)

(IE)
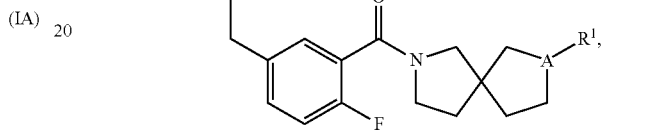

(IF)

(IG)
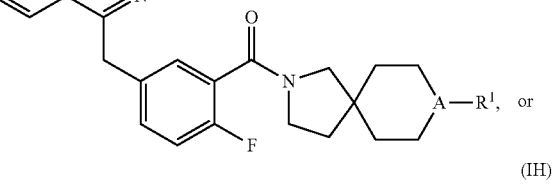, or (IH)
.

Aspect 34: The compound of aspect 1, or a pharmaceutically acceptable salt thereof, of the formula:

(IIA)
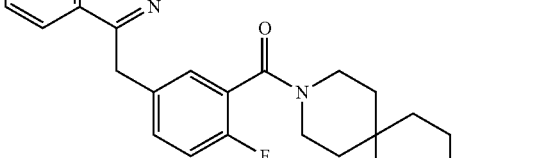 or

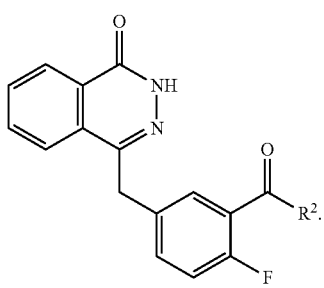
(IIB)
Aspect 35: The compound of aspect 1, or a pharmaceutically acceptable salt thereof, that is:
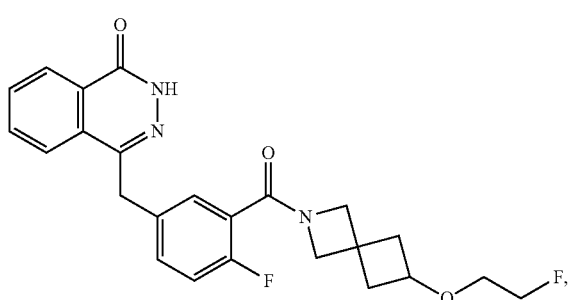
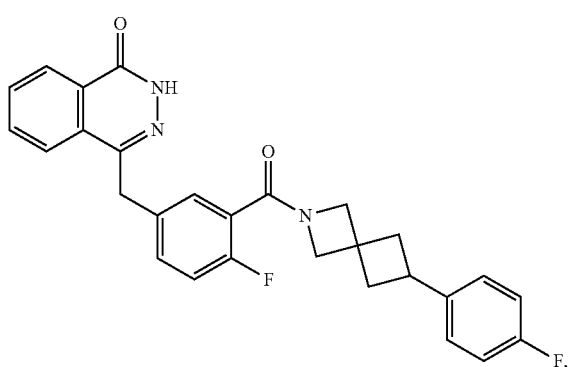
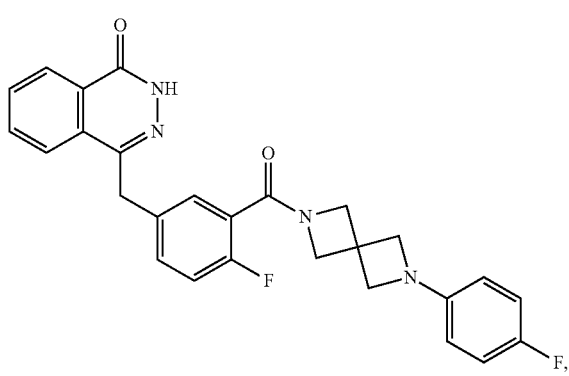
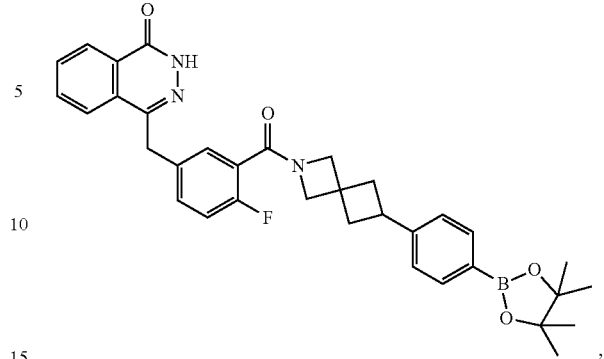
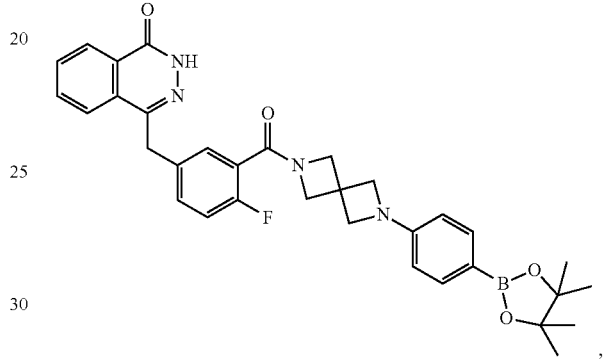
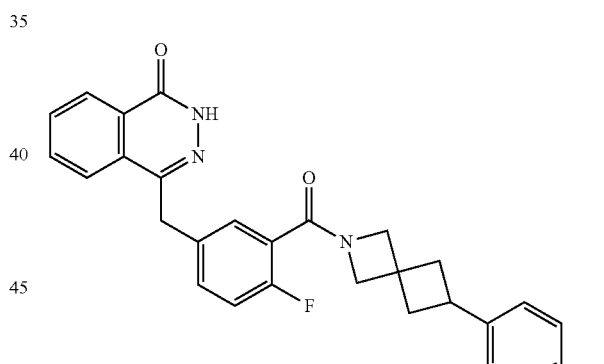
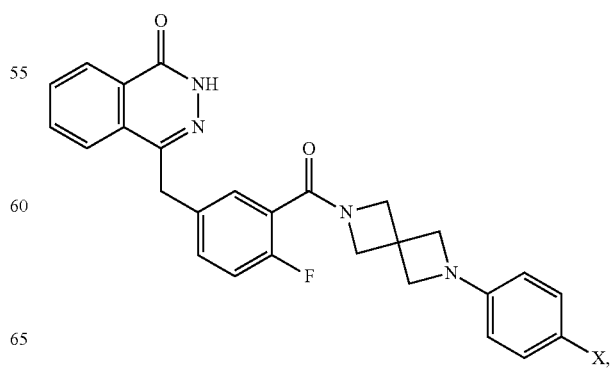

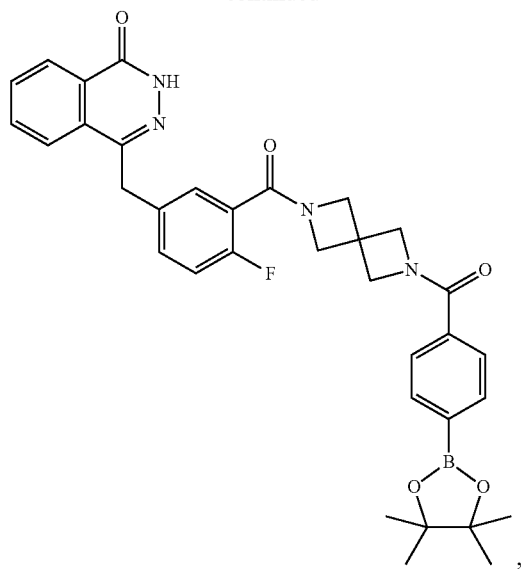
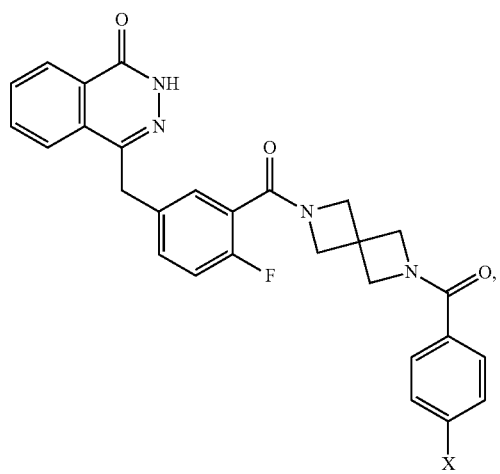
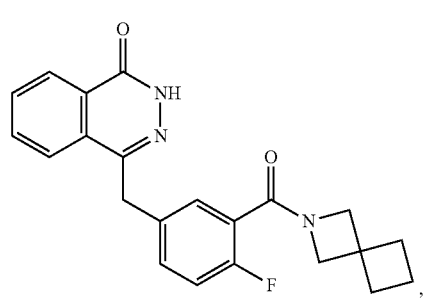
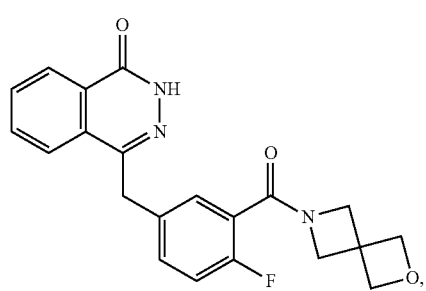
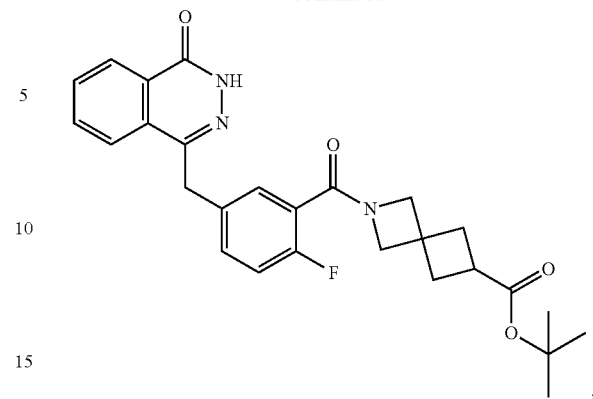
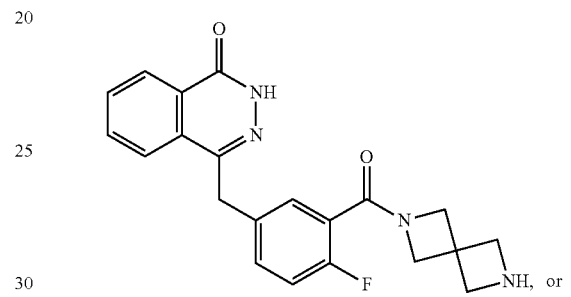
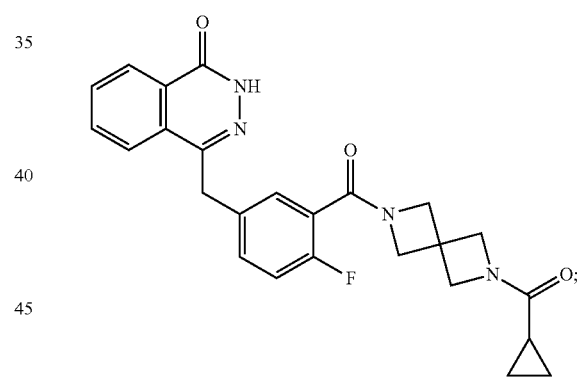
wherein, X is $^{18}F$, $^{19}F$, $^{123}I$, $^{124}I$, $^{125}I$, $^{131}I$, $^{76}Br$, $^{77}Br$, or $^{211}At$.
Aspect 36: The compound of aspect 1, or a pharmaceutically acceptable salt thereof, that is:
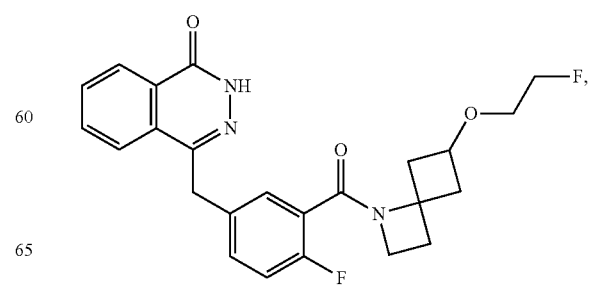

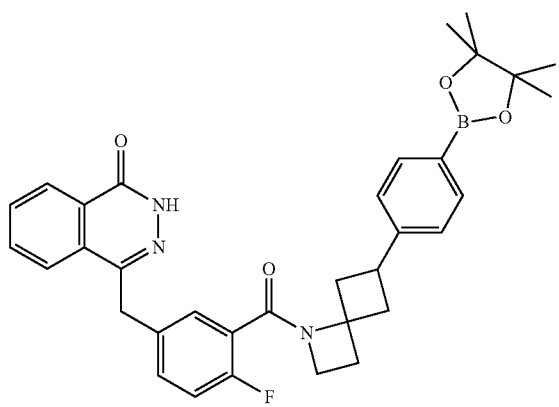
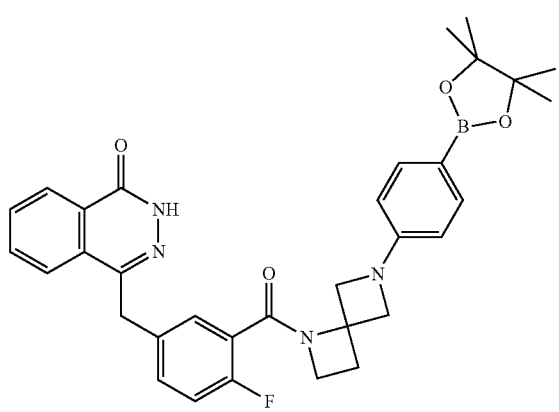
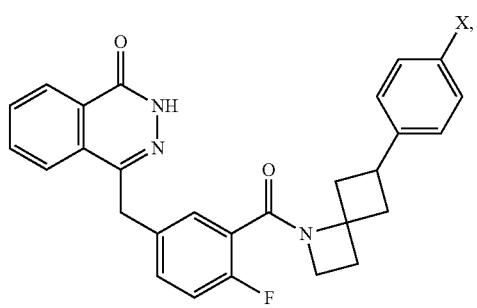
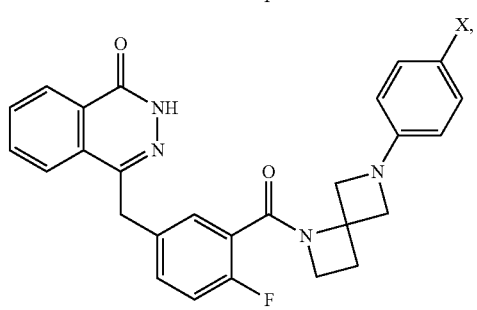
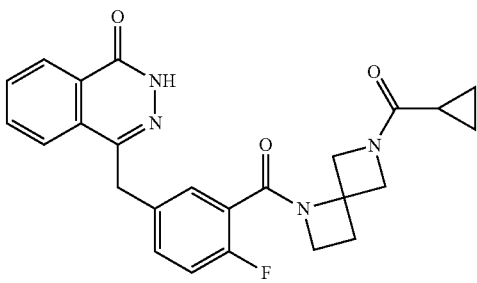
wherein, X is $^{18}$F, $^{19}$F, $^{123}$I, $^{124}$I, $^{125}$I, $^{131}$I, $^{76}$Br, $^{77}$Br, or $^{211}$At.
Aspect 37: The compound of aspect 1, or a pharmaceutically acceptable salt thereof, that is:
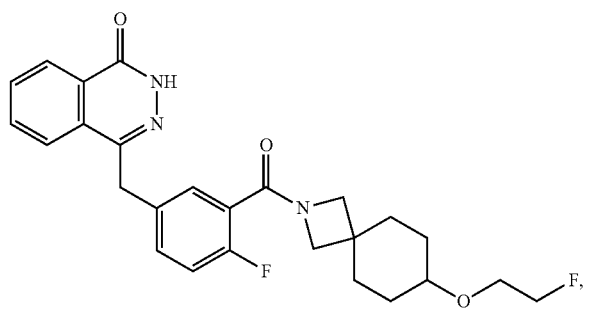
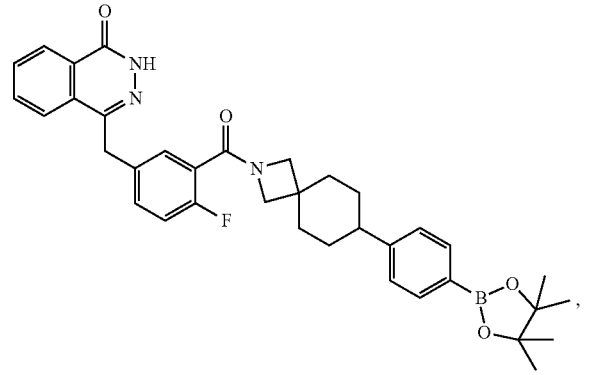
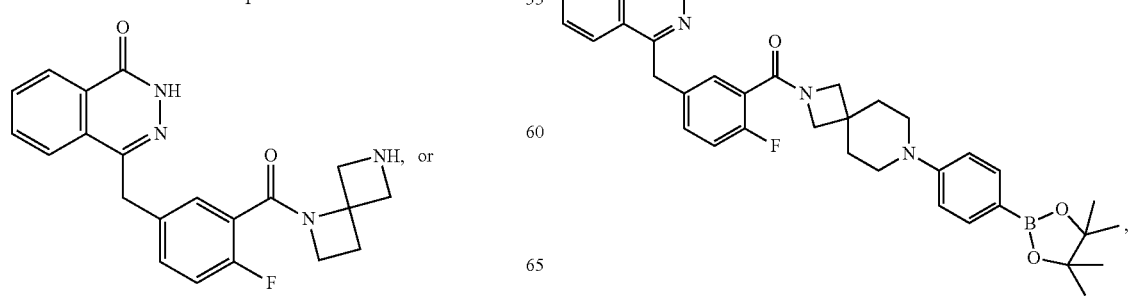

-continued
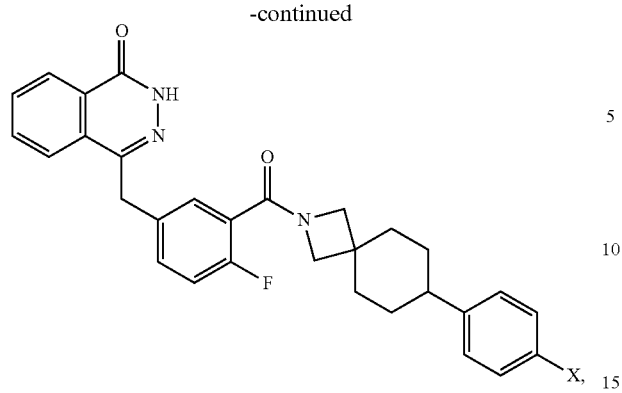
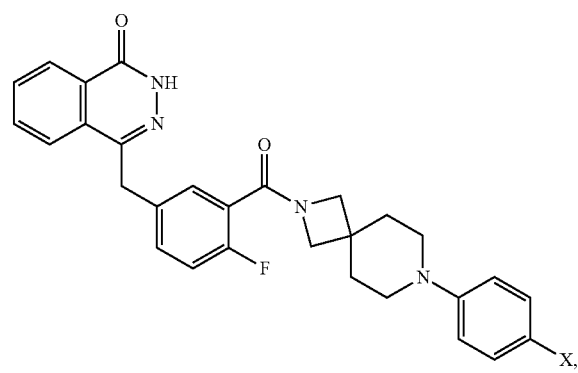
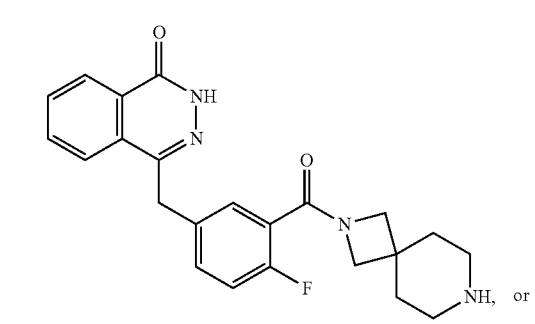
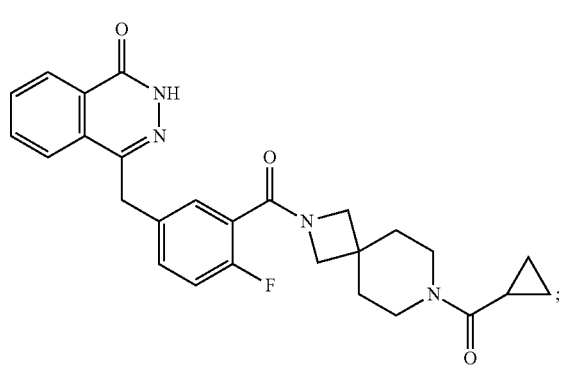
wherein, X is $^{18}$F, $^{19}$F, $^{123}$I, $^{124}$I, $^{125}$I, $^{131}$I, $^{76}$Br, $^{77}$Br, or $^{211}$At.
Aspect 38: The compound of aspect 1, or a pharmaceutically acceptable salt thereof, that is:
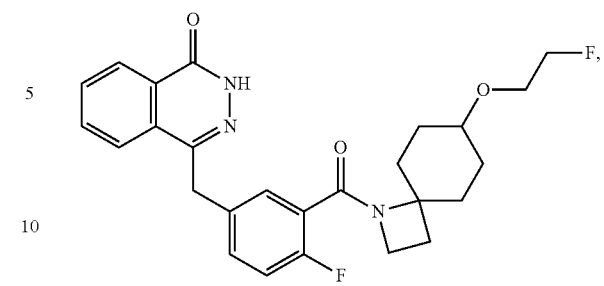
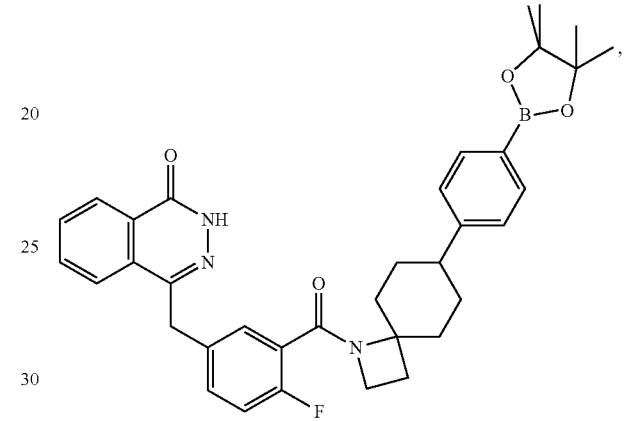
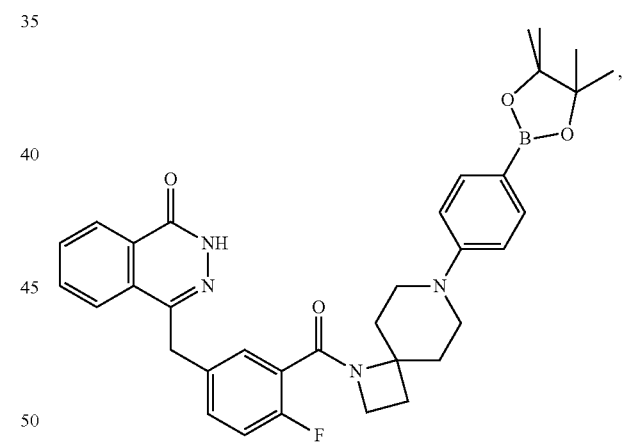
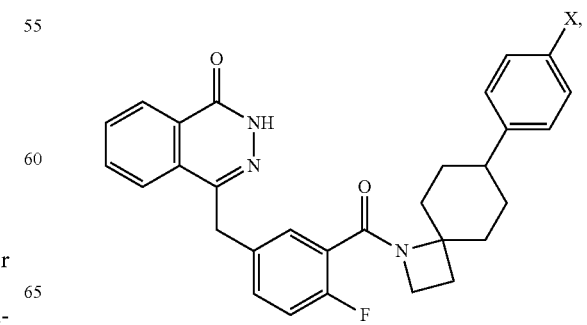
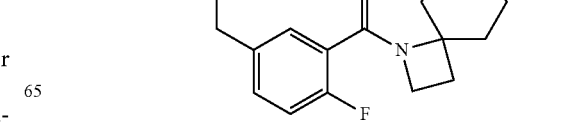

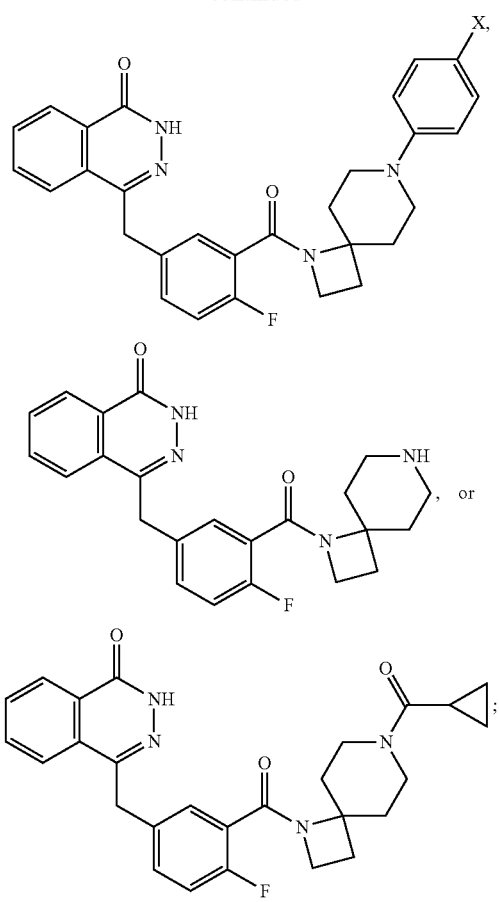
wherein, X is $^{18}F$, $^{19}F$, $^{123}I$, $^{124}I$, $^{125}I$, $^{131}I$, $^{76}Br$, $^{77}Br$, or $^{211}At$.
Aspect 39: The compound of aspect 1, or a pharmaceutically acceptable salt thereof, that is:
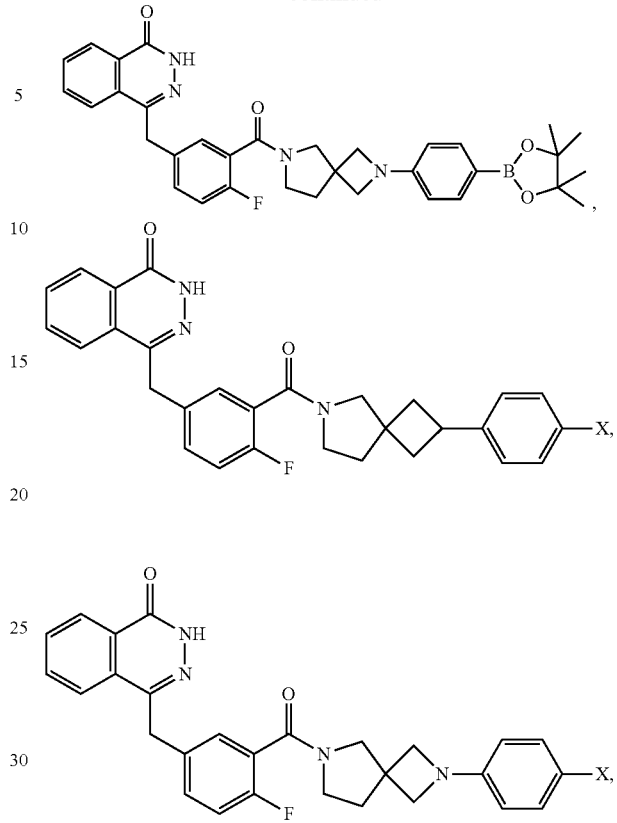
wherein, X is $^{18}F$, $^{19}F$, $^{123}I$, $^{124}I$, $^{125}I$, $^{131}I$, $^{76}Br$, $^{77}Br$, or $^{211}At$.
Aspect 40: The compound of aspect 1, or a pharmaceutically acceptable salt thereof, that is:

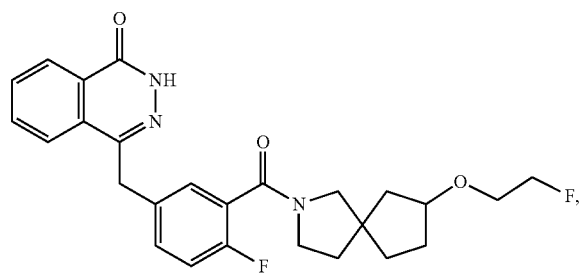
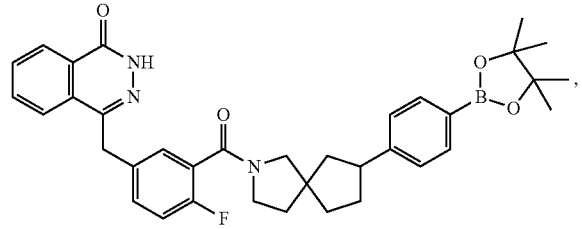
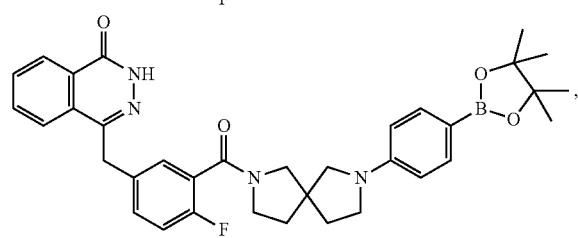
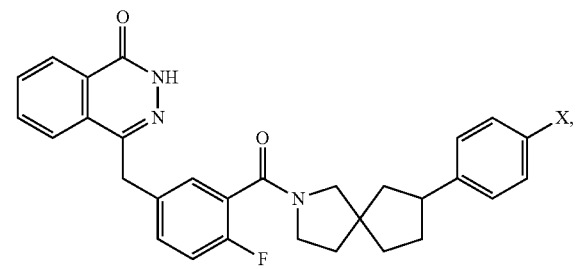
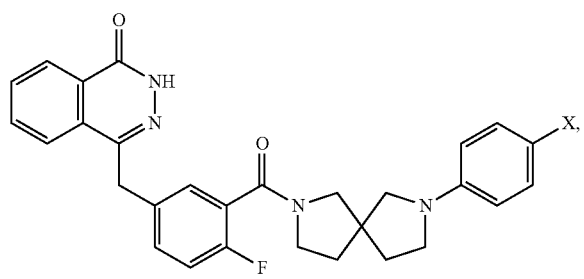
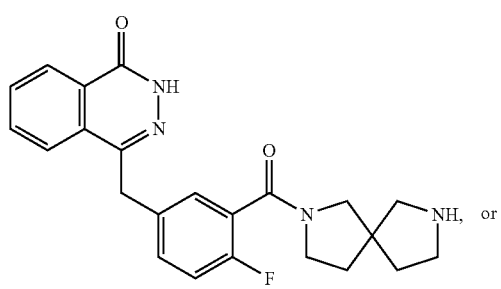
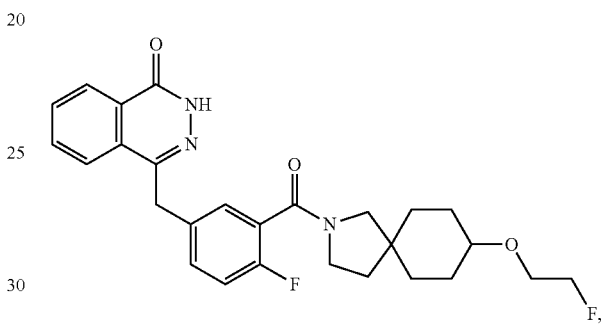
wherein, X is $^{18}F$, $^{19}F$, $^{123}I$, $^{124}I$, $^{125}I$, $^{131}I$, $^{76}Br$, $^{77}Br$, or $^{211}At$.
Aspect 41: The compound of aspect 1, or a pharmaceutically acceptable salt thereof, that is:
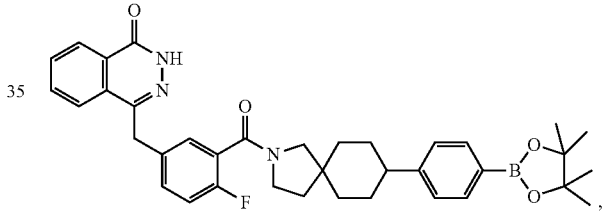
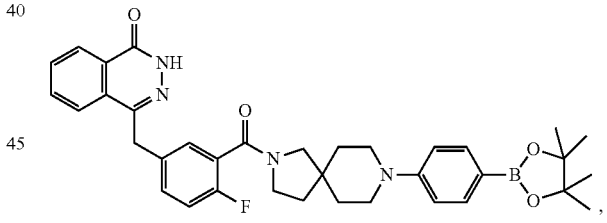
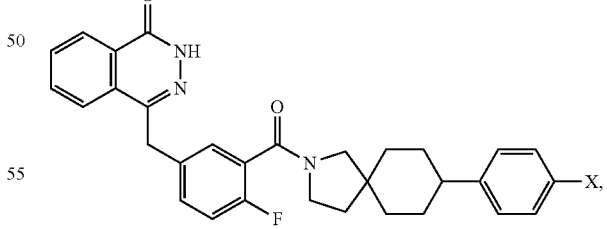
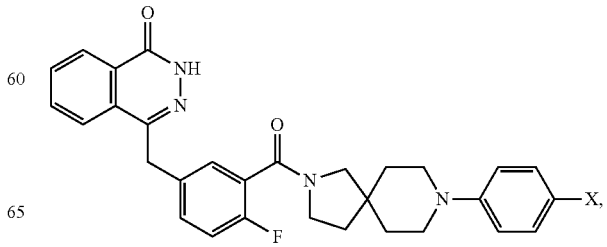

wherein, X is $^{18}F$, $^{19}F$, $^{123}I$, $^{124}I$, $^{125}I$, $^{131}I$, $^{76}Br$, $^{77}Br$, or $^{211}At$.

Aspect 42: The compound of aspect 1, or a pharmaceutically acceptable salt thereof, that is:

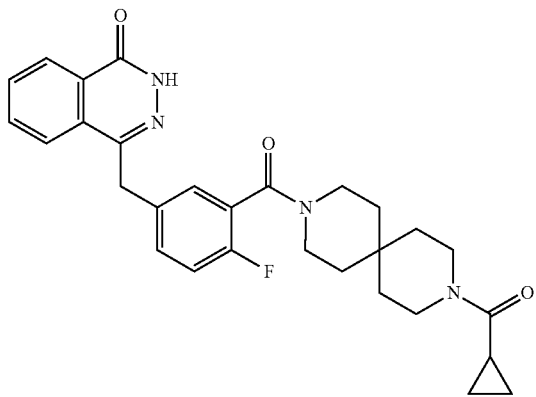
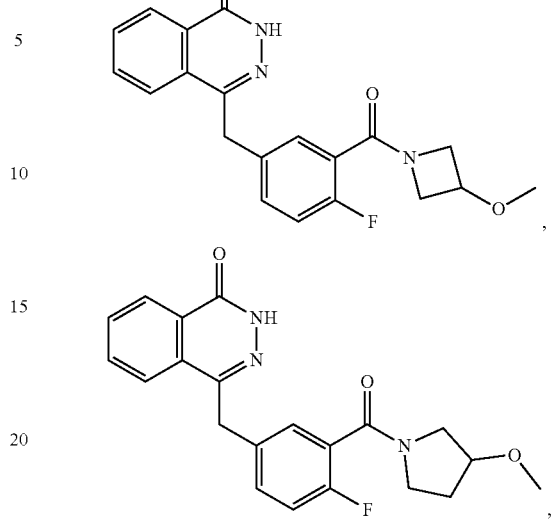
wherein, X is $^{18}$F, $^{19}$F, $^{123}$I, $^{124}$I, $^{125}$I, $^{131}$I, $^{76}$Br, $^{77}$Br, or $^{211}$At.
Aspect 43: The compound of aspect 1, or a pharmaceutically acceptable salt thereof, that is:
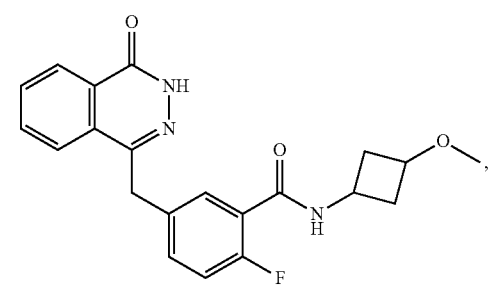
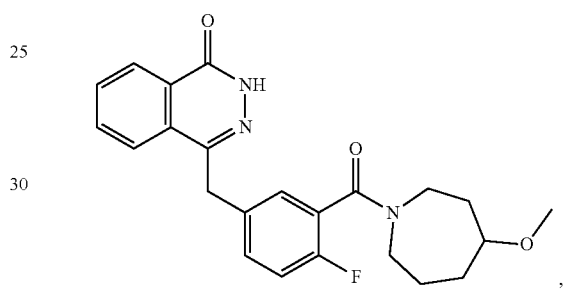
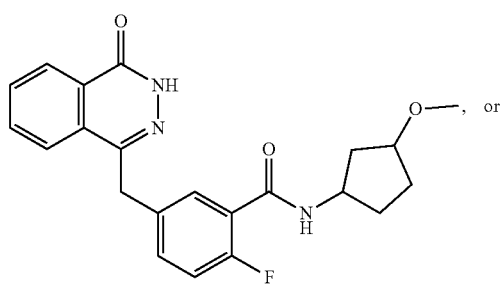, or
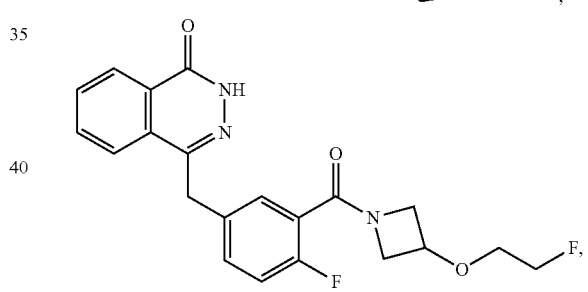
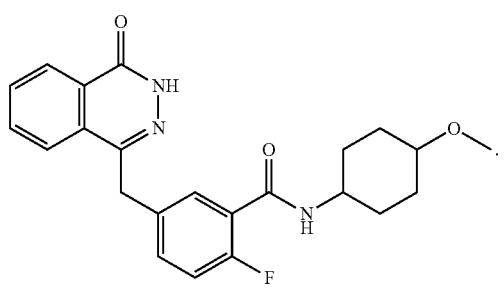.
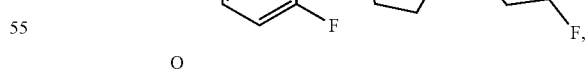
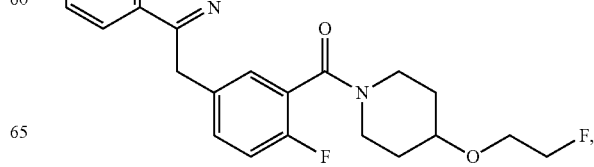
Aspect 44: The compound of aspect 1, or a pharmaceutically acceptable salt thereof, that is:

-continued

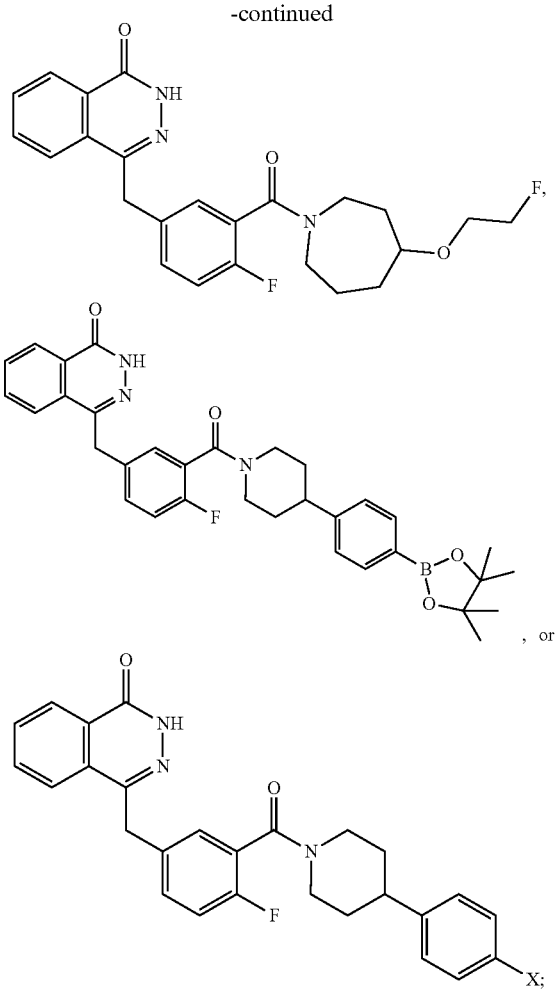

, or wherein, X is $^{18}F$, $^{19}F$, $^{123}I$, $^{124}I$, $^{125}I$, $^{131}I$, $^{76}Br$, $^{77}Br$, or $^{211}At$.

Aspect 45: A compound that is an isotopic variant of any one of the preceding aspects.

Aspect 46: A pharmaceutical composition comprising a compound of any one of the preceding aspects, or a pharmaceutically acceptable salt thereof, and a pharmaceutically acceptable excipient.

Aspect 47: A method of preparing a pharmaceutical composition of aspect 46, comprising combining a compound of any one of aspects 1 to 45, or a pharmaceutically acceptable salt thereof, with a pharmaceutically acceptable excipient.

Aspect 48: A method of treating a poly(ADP-ribose) polymerase-1-mediated disease or disorder in a subject, comprising administering to the subject a therapeutically effective amount of a compound of any one of aspects 1 to 45, or a pharmaceutically acceptable salt thereof.

Aspect 49: The method of aspect 48, wherein the poly (ADP-ribose)polymerase-1-mediated disease or disorder is a neurodegenerative disease or cancer.

Aspect 50: The method of aspect 49, wherein the neurodegenerative disease is Alzheimer's disease, Parkinson's disease, or Huntington's disease.

Aspect 51: The method of aspect 49, wherein the cancer is breast cancer, uterine cancer, lung cancer, ovarian cancer, and skin cancer, or non-Hodgkin's lymphoma.

Aspect 52: A method of detecting a poly(ADP-ribose) polymerase-1-mediated neurodegenerative disease or disorder, comprising:
(a) administering an effective amount of an isotopically-labeled compound of aspect 45 to a subject; and
(b) performing positron emission tomography or single photon emission computed tomography on said subject.

Aspect 53: A method of monitoring cancer treatment in a subject, comprising:
(a) administering a chemotherapeutic or radiation to said subject;
(b) administering an effective amount of an isotopically-labeled compound of formula I of aspect 45 to said subject; and
(c) performing positron emission tomography or single photon emission computed tomography on said subject.

Aspect 54: A method of detecting a poly(ADP-ribose) polymerase-1-mediated cancer in a subject, comprising:
(a) administering an effective amount of a compound of formula I of aspect 45 said subject; and
(b) performing positron emission tomography or single photon emission computed tomography on said subject.

EXAMPLES

Example 1

A. Abbreviations

ACN, acetonitrile; AMP, adenosine monophosphate; CNS, central nervous system; DCM, dichloromethane; D2R, dopamine D2 receptor; D3R, dopamine D3 receptor; HEK cells, human embryonic kidney 293 cells; [$^{125}I$]IABN, [$^{125}I$]-N-benzyl-5-iodo-2,3-dimethoxy[3.3.1]azabicyclo-nonan-3-O-ylbenzamide; Pd, palladium; TFA, trifluoroacetic acid.

B. General

Chemical compounds 1-8 were purchased and used without further purification. Compound 9 was prepared as described in Zmuda, Synthesis and Evaluation of a Radioiodinated Tracer with Specificity for Poly(ADP-ribose) Polymerase-1 (PARP-1) in Vivo. J. Med. Chem. 2015, 58 (21), 8683-8693 and Menear, 4-[3-(4-Cyclopropanecarbonylpiperazine-1-carbonyl)-4-fluorobenzyl]-2H-phthalazin-1-one: A Novel Bioavailable Inhibitor of Poly(ADP-ribose) Polymerase-1. J. Med. Chem. 2008, 51 (20), 6581-6591. NMR spectra were taken on a Bruker DMX 500 MHz. Mass spectroscopy data and compound purity analysis were acquired using ESI technique on 2695 Alliance LCMS. All other commercial reagents were purchased and used without further purification. Purification of organic compounds were carried out on a Biotage Isolera One with a dual-wavelength UV-VIS detector. Chemical shifts (δ) in the NMR spectra (H and $^{13}C$) were referenced by assigning the residual solvent peaks.

C. Cell Culture

Cells were cultured using standard techniques at 37° C. with 5% $CO_2$ and 15% 02. In this work OVCAR8 ovarian cancer cell lines were used for radioligand binding to characterize: PARP-1 affinity and to assess in vitro cytotoxicity of compounds synthesized in this work. Genetically engineered PARP-1 and PARP-2 double knockout mouse embryonic fibroblast (MEF) were used for cell viability studies with wildtype control. All cells were cultured in RPMI 1640 with 10% FBS and 1% penicillin/streptomycin.

D. PARP-1 Radioligand Binding in Live OVCAR8 Cells

The affinity of each compound for the PARP-1 enzyme was evaluated using a radioligand binding method described in Makvandi, A radiotracer strategy to quantify PARP-1 expression in vivo provides a biomarker that can enable patient selection for PARP inhibitor therapy. *Cancer Research* 2016. Briefly, OVCAR8 ovarian cancer cells were seeded in 96-well Stripwell plates at a density of 40,000 cells/well 24 hrs prior to the study. On the day of study, compounds were diluted in RPMI to concentrations of 100 μM-0.064 nM. Next, [$^{125}$I]KX1, a known PARP-1 specific radioligand, was added to the plate followed by each compound dilution. Reactions were allowed to equilibrate for 1 hr and were then washed with 200 μL of PBS. Wells were separated and counted on an automatic Wizard gamma counter (Perkin Elmer, Waltham Mass.). Dose response curves were produced to calculate 50% maximum inhibition values ($IC_{50}$) using non-linear fit sigmoidal dose response curves in GraphPad 7.0 (Prism, La Jolla Calif.). Experiments were repeated three times with adjusting dose concentrations to increase accuracy of $IC_{50}$ values.

E. Cell Viability Assays

Cell viability assays were carried out using four cell lines including OVCAR8, MEF wt, MEF PARP-1 (−/−) KO, and MEF PARP-2 (−/−) KO as described in Makvandi cited above. Briefly, cells were seeded in black well clear bottom 96-well plates at concentrations of 1,000 cells/well. After 24 h, cells were then treated with concentrations from 100-0.016 μM. Cells were incubated with compounds for 4-7 days and then assayed for cell viability using the luminescent based assay, CellTiter Glo (Promega, Waltham Mass.). Plates were read on an Enspire multimode plate reader (Perkin Elmer). Data was normalized to percent survival at each concentration evaluated by diving the luminescent signal in treated wells vs. the average of vehicle controls. Experiments were repeated three times and all compounds were assayed during each experiment.

F. Pgp-Glo™ Assay

P-gp activity of each compound was measured using Promega Pgp-Go™ Assay Systems. 25 μg of diluted recombinant human P-gp membranes were added to untreated white opaque multiwell plates along with Pgp-Glo™ Assay Buffer, a non-limiting concentration of ATP (5 mM) and 20 μL of each test compound (20 μM) for 1 hr at 37° C. Untreated and $Na_3VO_4$-treated control samples were also tested in addition to Verapamil-treated samples (positive control). After incubation, 50 μL of ATP Detection Reagent was added to all wells to stop the P-gp reaction. Samples were mixed briefly on a plate shaker then incubated plate at room temperature for 20 minutes to allow luminescent signal to develop. Luminescence was read on a plate-reading luminometer. This luciferase-based detection reaction provides a linear response to ATP concentration in each sample. Thus any changes in signal directly reflect changes in ATP concentration.

G. Radiochemistry

The radiosynthesis of [$^{18}$F]31 was accomplished on a Synthera synthesis module with full automation. Briefly, [$^{18}$F]fluoride (800 mCi) was produced by proton irradiation of enriched $H_2^{18}O$ via the reaction of $^{18}O$ (p, n)$^{18}F$ by the Cyclone cyclotron (IBA). The [$^{18}$F]fluoride in a $H_2^{18}O$ solution is delivered to the hotcell, trapped on a preactivated Sep-Pak Light QMA Carb cartridge (Waters), and eluted to the reaction vial with 1 mL of eluent containing 2 mg of potassium carbonate and 7 mg of Kryptofix in a mixture of 0.85 mL of acetonitrile and 0.15 mL of water. The residual water was evaporated azotropically with 1 mL of acetonitrile at 100° C. under a stream of nitrogen gas and vacuum. A solution of 4 mg of tosylate precursor BB in 0.7 mL of methyl sulfide (DMSO) was added to the reaction vial for a 20 min reaction. The crude product was diluted with 3 mL of the mobile phase and passed through an Alumina N Light cartridge (Waters) and a 0.45 m nylon filter to the HPLC loop for high-performance chromatography (HPLC). A Phenomenex Luna 5 μm C18 100 Å LC Column 250×10 mm semipreparative column with a mobile phase of acetonitrile and water (40:60 by volume) was used for HPLC purification. At a flow rate of 4 mL/min, the product was eluted at 11 min and diluted with water to a volume of 50 mL. The diluted product solution was passed through a Sep-Pak Plus C18 cartridge (Waters). The trapped product was rinsed with water to waste and then eluted with ethanol (0.6 mL, with 0.1% ascorbic acid) followed by 8 mL of normal saline to the final production vial through a 0.2 m nylon filter. After being shaken well, the final product was ready for quality control (QC) and animal studies. The yield ranged from 8 to 11% (decay corrected to the start of synthesis) in an average time of 65 min from receipt of [$^{18}$F]fluoride in a $H_2^{18}O$ solution from the cyclotron.

H. In Vitro Autoradiography

The normal Balb/c mouse (male, 10-12 weeks-old) frozen brain sections (10-μm thickness) were prepared using a cryostat microtome (CM1900, Leica, Germany) one day before and kept in −80° C. freezer. The sections were first thawed at room temperature for 20 min and rehydrated with ice-cold PBS buffer (pH 7.4) for 5 min. Then all sections were incubated with 4 nM [$^{18}$F]31 with, or without, 10 M olaparib at room temperature for 1 h to define the control and nonspecific binding groups. After the radioligand incubation, all of them were washed three times with ice-cold PBS for 3 min, dried up with a fan, and exposed to a BAS-SR 2040 imaging plate (20×40 cm, Fujifilm, Japan) for 2 hr. In the end the plate were scanned with a Typhoon 7000 phosphorimager (GE Healthcare) in a condition of 500 V and a resolution of 25 m.

I. MicroPET Imaging

All animal studies were performed under protocols approved by the University of Pennsylvania Institutional Animal Care and Use Committee. Male rhesus macaques (13-21 year old) were sedated with ketamine/dexdomidor and anesthesia maintained for imaging with 1% isoflurane. Temperature was maintained with a recirculating water warm pad and vital signs such as blood pressure, pulse oximetry, and EKG were monitored continuously. Three rhesus macaques were scanned on the G-PET, a high sensitivity, high resolution PET scanner using gadolinium orthosilicate crystals incorporated into an Anger-logic detector developed for brain imaging. Data was acquired for up to 50 min (6×10 sec, 3×60 sec, 3×120 sec, 3×180 sec, 4×300 sec, and 1 ×600 sec) in list mode after an intravenous injection of 101.6 MBq [$^{18}$F]FTT to one of the rhesus macaques, and 91.4-128.8 MBq [$^{18}$F]31 to two of the rhesus macaques. A venous blood sample was drawn into a heparinized syringe at 37 min post [$^{18}$F]9 injection for metabolite analysis. The acquired data were sorted into sinograms and reconstructed using the fully 3D LOR-RAMLA iterative reconstruction algorithm. Six volumes of interest (VOIs) including striatum, thalamus, frontal cortex, occipital cortex, whole brain, and cerebellum were manually delineated with PMOD image analysis software (version 3.7, PMOD Technologies LLC). Time activity curves were extracted from all the VOIs and performed as percentage injection dose per cc. (% ID/c.c.) and standard uptake value (SUV).

J. Metabolite Analysis

The blood samples were centrifuged at 3000 G for 10 min to separate plasma and red blood cells. 2 mL acetonitrile was added to the sample of plasma (1 mL). The plasma solution was vortexed, followed by centrifugation at 3000 G for 10 min. After the supernatant had been separated from the pellet, each portion was counted with a gamma counter (PerkinElmer Wizard 2480) to determine the extraction efficiency. Each supernatant was diluted with water and passed through a 0.45 um nylon filter for HPLC injection. With Agilent 1200 series, 200 L solution was injected onto Agilent SB-C18 column (250×10 mm) for analysis. The mobile phase was 34% acetonitrile in water (volume) and the flow rate was 1 mL/min. The HPLC eluent was collected 1 tube/min and 16 tubes were collected for each injection. The collected HPLC fractions were measured by Gamma Counter for further data analysis. Meanwhile the cold reference was also injected and monitored at 254 nm UV wavelength.

Example 2: General Method for Preparing Diazaspiro Analogues 10-17

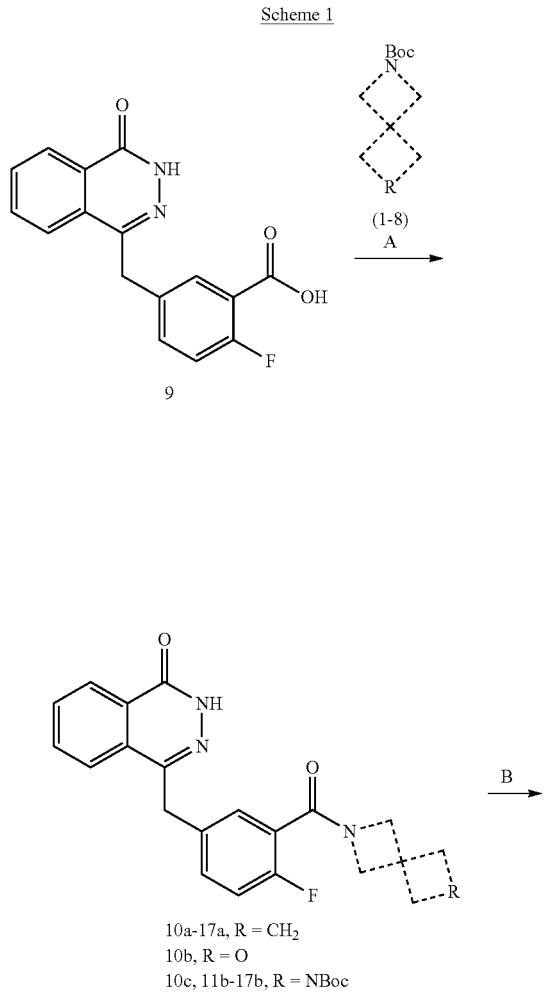

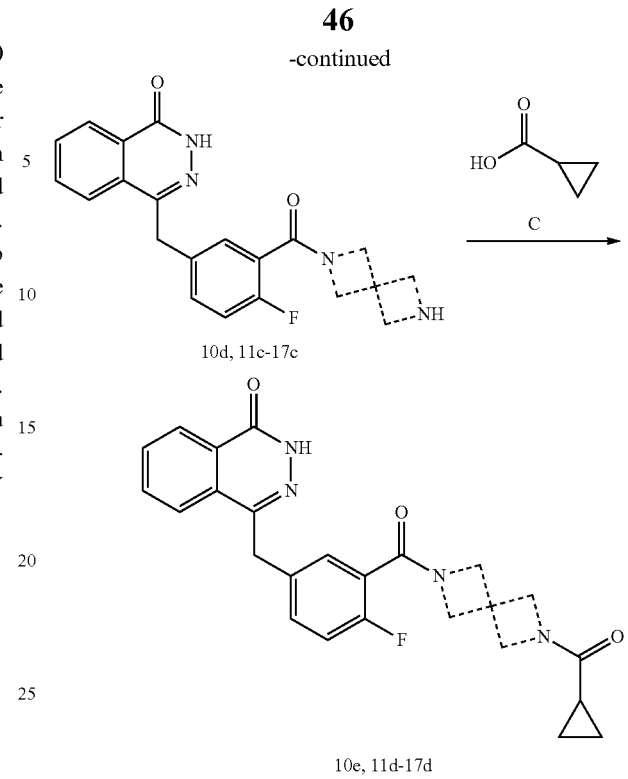

Reagents and conditions: (A) spiro compound (1-8), HOBt hydrate, EDC HCl, TEA, THF, 60° C., 12 h; (b) TFA, CH$_2$Cl$_2$, rt; (c) Free-amine compound (10d, 11c-17c), cyclopropane carboxylic acid, HOBt hydrate, EDC HCl, TEA, THF, 60° C., 12 h.

As described in general Scheme 1, amide coupling of 9 with commercially available spiro analogues 1-8 afforded 10a-17a and 10b-17b in good to moderate yields. Compounds 10c-17c were obtained following removal of the boc-protecting groups, followed by basification to afford the free-amine analogues. More specifically, a one-pot mixture of the respective azaspirocycle (1.0 mmol), 9 (1.0 mmol), HOBt hydrate (1.0 mmol), EDC hydrochloride (1.0 mmol), and Et$_3$N (2.0 mmol) was stirred in 5 mL of THF at 60° C. for 12 h. A saturated NaHCO$_3$ $_{(aq)}$ solution (15 mL) was then added to the crude reaction mixture and stirred at room temp for 1 h. The reaction mixture was extracted with CH$_2$Cl$_2$ (3×20 mL) to afford the crude product. The residue was loaded onto a Biotage SNAP flash purification cartridge, eluding with 10% 7N NH$_3$ in MeOH solution/CH$_2$Cl$_2$ to give compounds 10a-17a and 10b-17b.

The appropriate boc-protected compound (10b-17b) was then dissolved in CH$_2$Cl$_2$ (2 mL), followed by dropwise addition of CF$_3$COOH (2 mL), and stirred at room temperature for 3 h. Volatiles were then removed under reduced pressure and the crude product was neutralized with a saturated NaHCo$_3$ (aq) solution (10 mL). The reaction mixture was extracted with CH$_2$Cl$_2$ (3×20 mL), and the organic layers were combined, dried, and concentrated to afford the free-amine intermediates (10c-17c) as white foams in near quantitative yield. Compounds were analyzed for purity using LCMS, $^1$H and $^{13}$C NMR spectroscopy, and, if necessary, purified using a Biotage SNAP flash purification cartridge, eluding with 10% 7N NH$_3$ in MeOH solution/EtOAc.

TABLE 1

| Compound | R |
|----------|---|
| 10a | CH₂ |
| 10b | O |
| 10c | NBoc |
| 10d | NH |
| 10e | N-C(O)-cyclopropyl |
| 12a | CH₂ |
| 12b | NBoc |
| 12c | NH |
| 12d | N-C(O)-cyclopropyl |
| 13a | CH₂ |
| 13b | NBoc |
| 13c | NH |
| 13d | N-C(O)-cyclopropyl |
| 14a | CH₂ |
| 14b | NBoc |
| 14c | NH |
| 14d | N-C(O)-cyclopropyl |
| 15a | CH₂ |
| 15b | NBoc |
| 15c | NH |
| 15d | N-C(O)-cyclopropyl |

TABLE 1-continued

| Compound | R |
|---|---|
| 16a | CH₂ |
| 16b | NBoc |
| 16c | NH |
| 16d | N-C(=O)-cyclopropyl |

| Compound | R |
|---|---|
| 17a | CH₂ |
| 17b | NBoc |
| 17c | NH |
| 17d | N-C(=O)-cyclopropyl |

Example 3: General Method for Preparing Analogues 18-103

Compounds 18-25 can be prepared following Scheme 2. Compounds 45-46 can also be prepared following the coupling reaction outlined in Scheme 2 as well.

Reagents and conditions: (i) 9, commercially available methoxy-amine (a), HOBt hydrate, EDC HCl, TEA, THF, 60° C., 12 h.

Compounds 26, 28-29, 31, 33, 37, 47, 55, 63, 71, 79, 87, and 95 can be synthesized following the procedure in Scheme 3.

Scheme 2

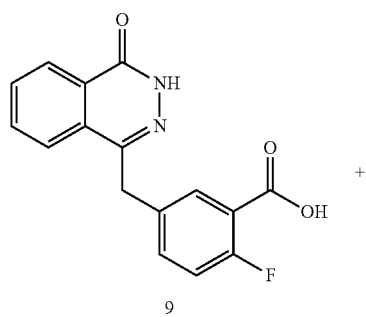

Scheme 3

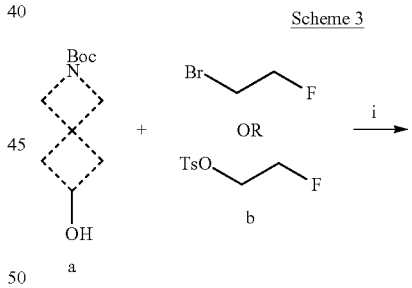

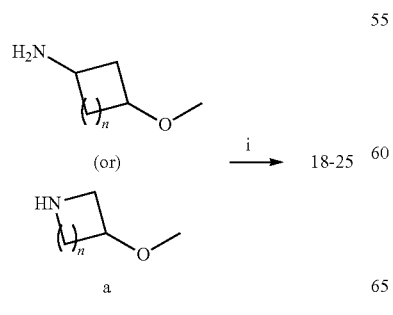

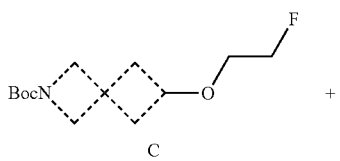

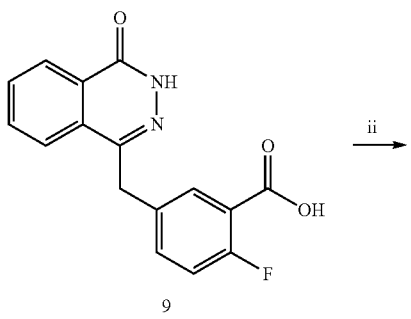

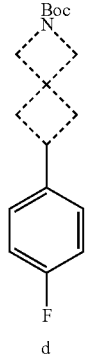

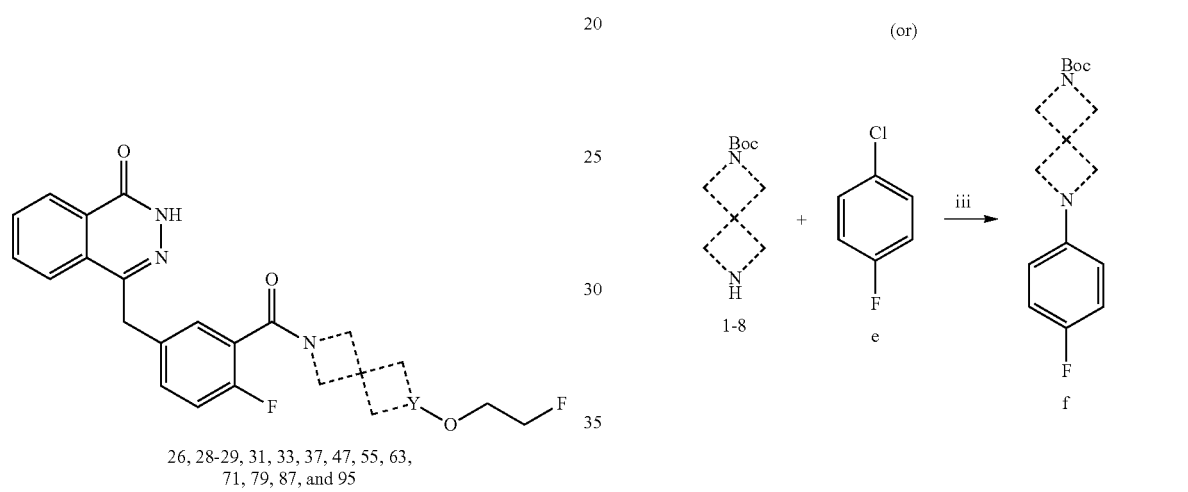

Reagents and conditions: (i) commercially available amine alcohol (a), NaH, DMF, rt, 3 h; (ii) c, 9, HOBt hydrate, EDC HCl, TEA, THF, 60° C., 12 h.

Compounds 39-40, 49-50, 57-58, 65-66, 73-74, 81-82, 89-90, and 97-98 can be synthesized following the procedure in Scheme 4. Synthetic route ii was adapted from Fu, J. Am. Chem. Soc. 2006, 128, 5360, while route iii was reported by Mach, Tetrahedron Lett. 2017, 58, 466.

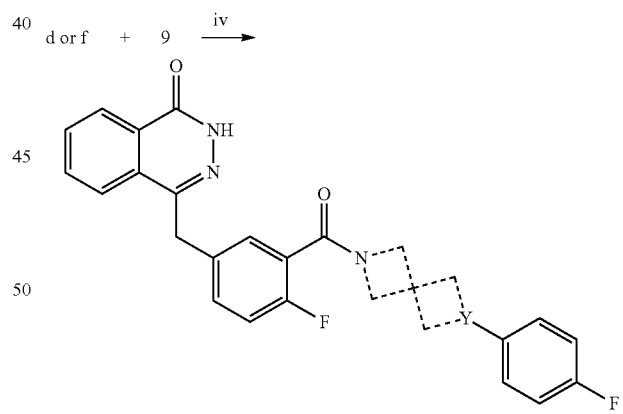

Y = CH or N
39-40, 49-50, 57-58, 65-66, 73-74, 81-82, 89-90, and 97-98

Reagents and conditions: (i) commercially available a, CBr$_4$, Ph$_3$P, CH$_2$Cl$_2$, 0-23° C., 4 h; (ii) as described in Fu, J. Am. Chem. Soc. 2006, 128, 5360; (iii) as described in Mach, Tetrahedron Lett. 2017, 58, 466; (iv) d or f, 9, HOBt hydrate, EDC HCl, TEA, THF, 60° C., 12 h.

Boronic ester compounds 35, 41-42, 51-52, 59-60, 67-68, 75-76, 83-84, 91-92, and 99-100 can be developed from the following procedure outlined in Scheme 5.

Scheme 4

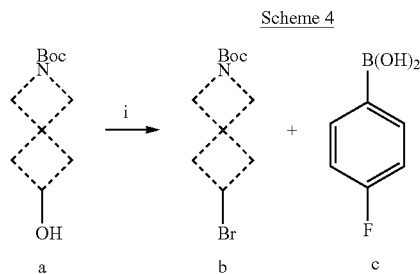

Scheme 5

Step 1

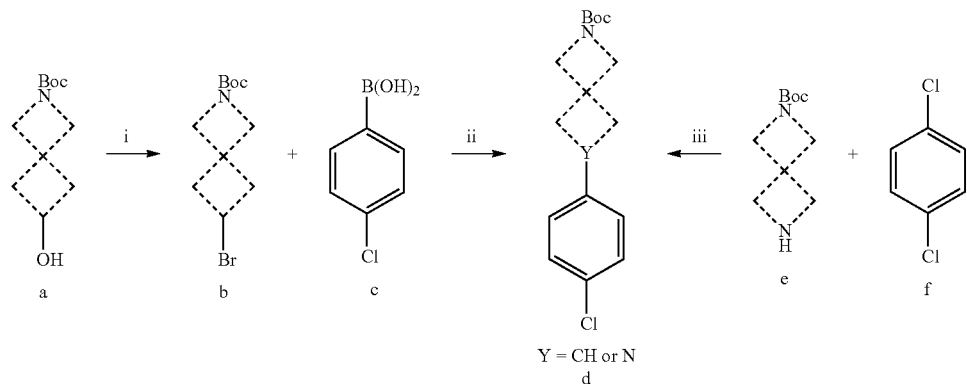

Y = CH or N
d

Step 2

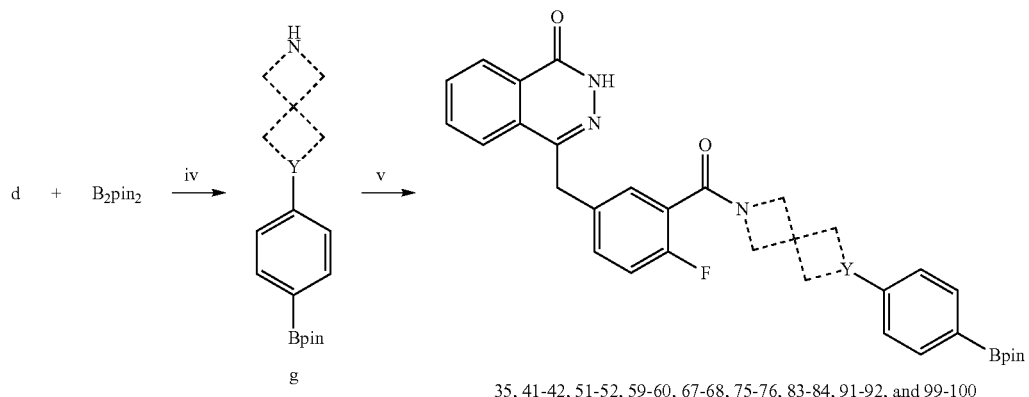

35, 41-42, 51-52, 59-60, 67-68, 75-76, 83-84, 91-92, and 99-100

Reagents and conditions: (i) a, CBr₄, Ph₃P, CH₂Cl₂, 0-23° C., 4 h; (ii) as described in Fu, J. Am. Chem. Soc. 2006, 128, 5360; (iii) as described in Mach, Tetrahedron Lett. 2017, 58, 466; (iv) 1: d, bis(pinacolato)diboron (B₂pin₂), Pd₂(dba)₃ (2 mol %), RuPhos (4 mol %), KOAc (3.0 equiv), dioxane, 110° C., 1 h; 2: CF₃COOH, CH₂Cl₂, rt, 2 h; (v) g, 9, HOBt hydrate, EDC HCl, TEA, THF, 60° C., 12 h.

Radiolabeled compounds can be accessed following the described methods in Scheme 6.

Scheme 6

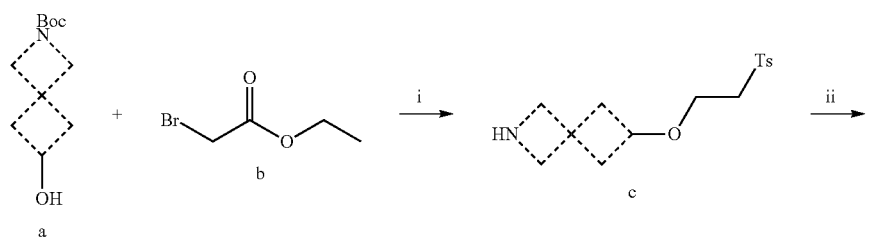

-continued
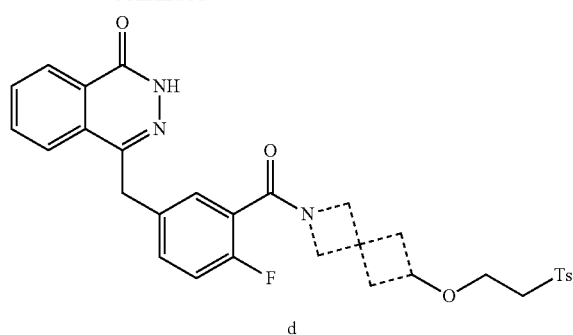
d
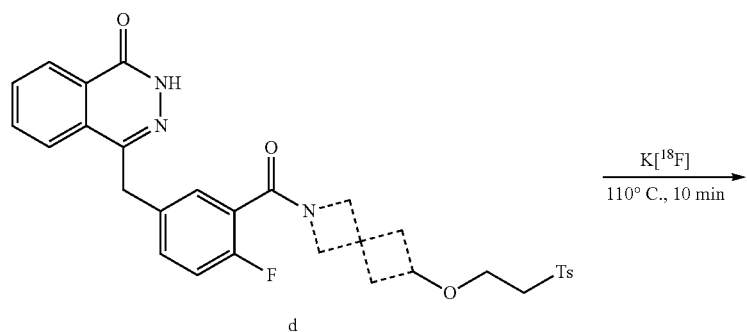
d
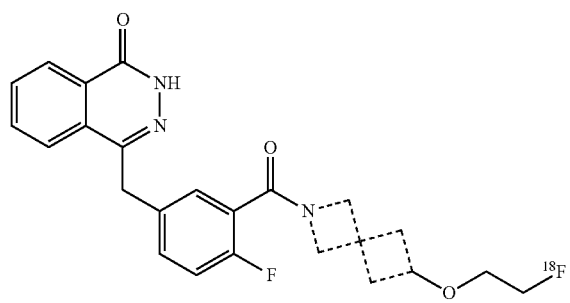
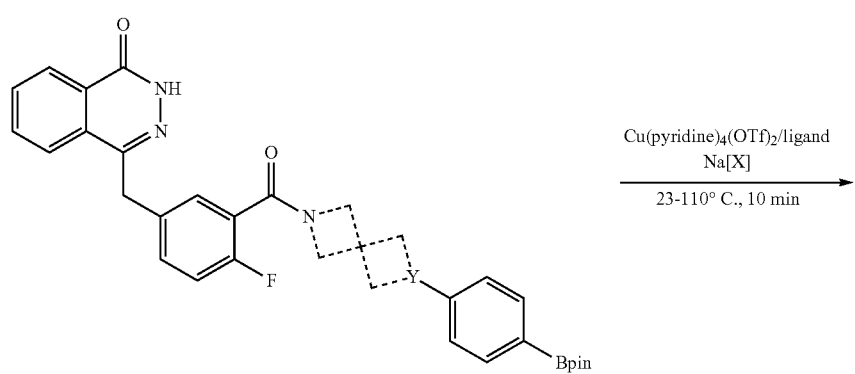
35, 41-42, 51-52, 59-60, 67-68, 75-76, 83-84, 91-92, or 99-100

-continued
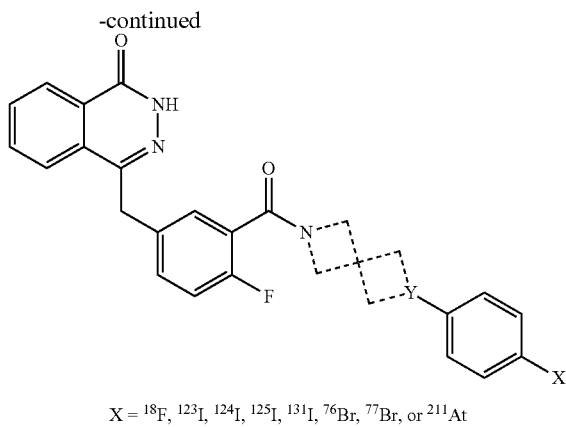
X = $^{18}$F, $^{123}$I, $^{124}$I, $^{125}$I, $^{131}$I, $^{76}$Br, $^{77}$Br, or $^{211}$At
Reagents and conditions: (i) 1) a, b, NaH, DMF, 23° C., 4 h; 2) 2 M LiBH$_4$ borohydride in THF; 3) 1 M Li(C$_2$H$_5$)$_3$BH in THF, 23° C., 12 h; 4) TsCl, Et$_3$N, CH$_2$Cl$_2$, 23° C., 12 h; 5) CF$_3$COOH, CH$_2$Cl$_2$, rt, 2 h; (ii) c, 9, HOBt hydrate, EDC HCl, TEA, THF, 60° C., 12 h.
TABLE 2
| | Compound | R |
|---|---|---|
| | 18 | 3-methoxycyclobutyl |
| | 19 (cis) 20 (trans) | 3-methoxycyclobutyl |
| | 21 | 3-methoxycyclopentyl |
| | 22 | 4-methoxycyclohexyl |

TABLE 2-continued

| Compound | R |
|---|---|
| 23 | 3-methoxyazetidin-1-yl |
| 24 | 3-methoxypyrrolidin-1-yl |
| 25 | 4-methoxyazepan-1-yl |
| 26 | 3-(2-fluoroethoxy)azetidin-1-yl |
| 27 | 3-(2-[$^{18}$F]fluoroethoxy)azetidin-1-yl |
| 28 (R) / 29 (S) | 3-(2-fluoroethoxy)pyrrolidin-1-yl |
| 30 | 3-(2-[$^{18}$F]fluoroethoxy)pyrrolidin-1-yl |
| 31 | 4-(2-fluoroethoxy)piperidin-1-yl |
| 32 | 4-(2-[$^{18}$F]fluoroethoxy)piperidin-1-yl |

TABLE 2-continued

| Compound | R |
|---|---|
| 33 | *azepane with 4-O-CH$_2$CH$_2$-F* |
| 34 | *azepane with 4-O-CH$_2$CH$_2$-$^{18}$F* |
| 35 | *piperazine-Y-phenyl-Bpin (pinacol boronate)*; Y = CH or N |
| 36 | *piperidine-4-(4-X-phenyl)*; X = $^{18}$F, $^{123}$I, $^{124}$I, $^{125}$I, $^{131}$I, $^{76}$Br, $^{77}$Br, $^{211}$At |
| 36B | *piperidine-4-(3-X-phenyl)*; X = $^{18}$F, $^{123}$I, $^{124}$I, $^{125}$I, $^{131}$I, $^{76}$Br, $^{77}$Br, $^{211}$At |

TABLE 2-continued
| Compound | R |
|---|---|
| 36C | 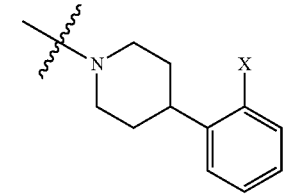<br>X = $^{18}$F, $^{123}$I, $^{124}$I, $^{125}$I, $^{131}$I, $^{76}$Br, $^{77}$Br, $^{211}$At |
| 36D | 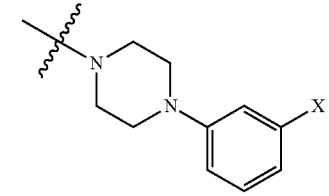<br>X = $^{18}$F, $^{123}$I, $^{124}$I, $^{125}$I, $^{131}$I, $^{76}$Br, $^{77}$Br, $^{211}$At |
| 36E | 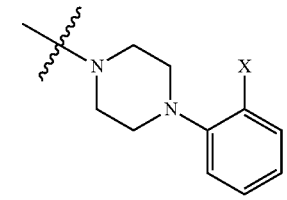<br>X = $^{18}$F, $^{123}$I, $^{124}$I, $^{125}$I, $^{131}$I, $^{76}$Br, $^{77}$Br, $^{211}$At |
| 37A | CHOCH$_2$CH$_2$CH$_2$F |
| 37B | CHOCH$_2$CH$_2$F |
| 38 | CHOCH$_2$CH$_2$CH$_2$$^{18}$F |
| 39 | 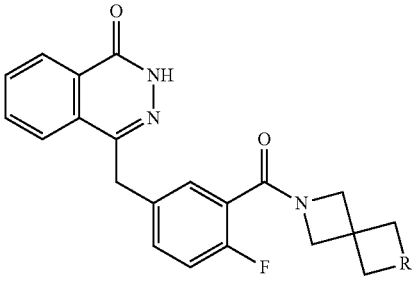 |
| 40 | 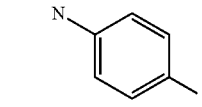 |
| 41 | 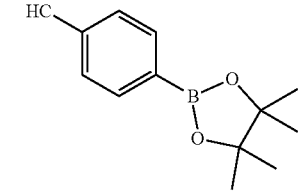 |
| 42 | 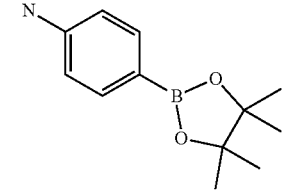 |

TABLE 2-continued
| Compound | R |
|---|---|
| 43 | 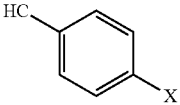<br>X = $^{18}$F, $^{123}$I, $^{124}$I, $^{125}$I, $^{131}$I, $^{76}$Br, $^{77}$Br, $^{211}$At |
| 43A | 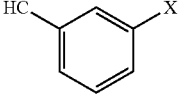<br>X = $^{18}$F, $^{123}$I, $^{124}$I, $^{125}$I, $^{131}$I, $^{76}$Br, $^{77}$Br, $^{211}$At |
| 43B | 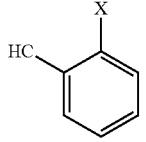<br>X = $^{18}$F, $^{123}$I, $^{124}$I, $^{125}$I, $^{131}$I, $^{76}$Br, $^{77}$Br, $^{211}$At |
| 44 | 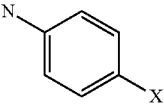<br>X = $^{18}$F, $^{123}$I, $^{124}$I, $^{125}$I, $^{131}$I, $^{76}$Br, $^{77}$Br, $^{211}$At |
| 44A | 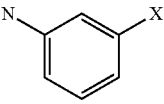<br>X = $^{18}$F, $^{123}$I, $^{124}$I, $^{125}$I, $^{131}$I, $^{76}$Br, $^{77}$Br, $^{211}$At |
| 44B | 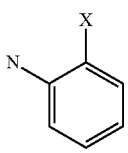<br>X = $^{18}$F, $^{123}$I, $^{124}$I, $^{125}$I, $^{131}$I, $^{76}$Br, $^{77}$Br, $^{211}$At |

TABLE 2-continued

| Compound | R |
|---|---|
| 45 | 4-(4,4,5,5-tetramethyl-1,3,2-dioxaborolan-2-yl)benzoyl (N-attached) |
| 46 | 4-X-benzoyl (N-attached) |
| 47 | CHOCH$_2$CH$_2$CH$_2$F |
| 47A | CHOCH$_2$CH$_2$F |
| 48 | CHOCH$_2$CH$_2$CH$_2^{18}$F |
| 48A | CHOCH$_2$CH$_2^{18}$F |
| 49 | 4-fluorobenzyl |
| 50 | 4-fluorophenyl (N-attached) |
| 51 | 4-(4,4,5,5-tetramethyl-1,3,2-dioxaborolan-2-yl)benzyl |
| 52 | 4-(4,4,5,5-tetramethyl-1,3,2-dioxaborolan-2-yl)phenyl (N-attached) |
| 53 | 4-X-benzyl |

X = $^{18}$F, $^{123}$I, $^{124}$I, $^{125}$I, $^{131}$I, $^{76}$Br, $^{77}$Br, $^{211}$At

TABLE 2-continued
| Compound | R |
|---|---|
| 54 | 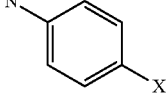 X = $^{18}$F, $^{123}$I, $^{124}$I, $^{125}$I, $^{131}$I, $^{76}$Br, $^{77}$Br, $^{211}$At |
| 55 | CHOCH$_2$CH$_2$CH$_2$F |
| 55A | CHOCH$_2$CH$_2$F |
| 56 | CHOCH$_2$CH$_2$CH$_2$$^{18}$F |
| 56A | CHOCH$_2$CH$_2$$^{18}$F |
| 57 | 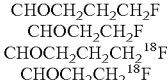 |
| 58 | 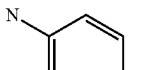 |
| 59 | 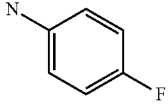 |
| 60 | 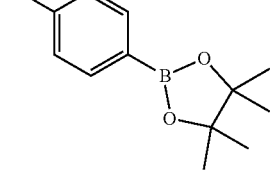 |
| 61 | 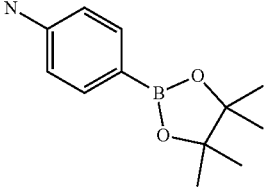 X = $^{18}$F, $^{123}$I, $^{124}$I, $^{125}$I, $^{131}$I, $^{76}$Br, $^{77}$Br, $^{211}$At |
| 62 | 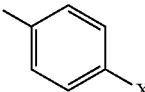 X = $^{18}$F, $^{123}$I, $^{124}$I, $^{125}$I, $^{131}$I, $^{76}$Br, $^{77}$Br, $^{211}$At |
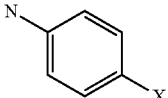

TABLE 2-continued

| Compound | R |
|---|---|
| 63 | CHOCH$_2$CH$_2$CH$_2$F |
| 63A | CHOCH$_2$CH$_2$F |
| 64 | CHOCH$_2$CH$_2$$^{18}$F |
| 64A | CHOCH$_2$CH$_2$$^{18}$F |
| 65 | HC—C$_6$H$_4$—F (4-fluorobenzyl) |
| 66 | N—C$_6$H$_4$—F (4-fluoroanilino) |
| 67 | HC—C$_6$H$_4$—Bpin (4-(pinacolboronate)benzyl) |
| 68 | N—C$_6$H$_4$—Bpin (4-(pinacolboronate)anilino) |
| 69 | HC—C$_6$H$_4$—X; X = $^{18}$F, $^{123}$I, $^{124}$I, $^{125}$I, $^{131}$I, $^{76}$Br, $^{77}$Br, $^{211}$At |
| 70 | N—C$_6$H$_4$—X; X = $^{18}$F, $^{123}$I, $^{124}$I, $^{125}$I, $^{131}$I, $^{76}$Br, $^{77}$Br, $^{211}$At |
| 71 | CHOCH$_2$CH$_2$CH$_2$F |
| 71A | CHOCH$_2$CH$_2$CH$_2$$^{18}$F |
| 72 | CHOCH$_2$CH$_2$CH$_2$$^{18}$F |
| 72A | CHOCH$_2$CH$_2$$^{18}$F |
| 73 | HC—C$_6$H$_4$—F (4-fluorobenzyl) |

TABLE 2-continued
| Compound | R |
|---|---|
| 74 | 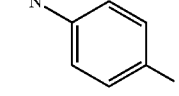 N-C6H4-F (para) |
| 75 | 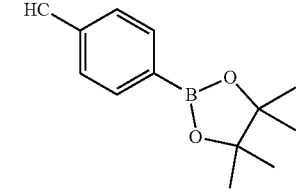 HC-C6H4-Bpin |
| 76 | 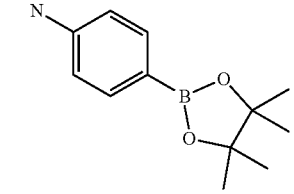 N-C6H4-Bpin |
| 77 | 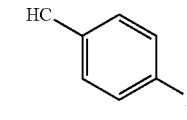 HC-C6H4-X<br>X = $^{18}$F, $^{123}$I, $^{124}$I, $^{125}$I, $^{131}$I, $^{76}$Br, $^{77}$Br, $^{211}$At |
| 78 | 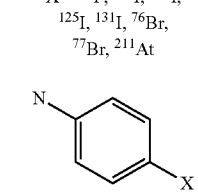 N-C6H4-X<br>X = $^{18}$F, $^{123}$I, $^{124}$I, $^{125}$I, $^{131}$I, $^{76}$Br, $^{77}$Br, $^{211}$At |
| 79 | CHOCH$_2$CH$_2$CH$_2$F |
| 79A | CHOCH$_2$CH$_2$F |
| 80 | CHOCH$_2$CH$_2$CH$_2$$^{18}$F |
| 80A | CHOCH$_2$CH$_2$$^{18}$F |
| 81 | 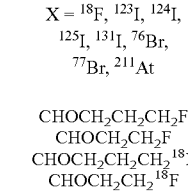 HC-C6H4-F |
| 82 | 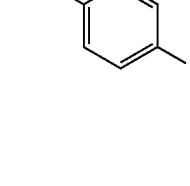 N-C6H4-F |
| 83 | 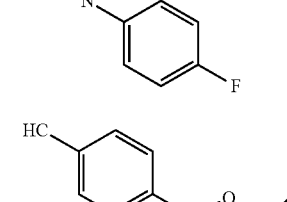 HC-C6H4-Bpin |

TABLE 2-continued
| Compound | R |
|---|---|
| 84 | 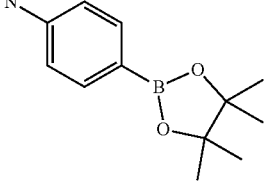 |
| 85 | 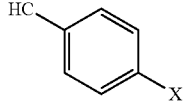<br>X = $^{18}$F, $^{123}$I, $^{124}$I, $^{125}$I, $^{131}$I, $^{76}$Br, $^{77}$Br, $^{211}$At |
| 86 | 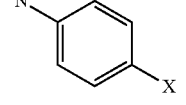<br>X = $^{18}$F, $^{123}$I, $^{124}$I, $^{125}$I, $^{131}$I, $^{76}$Br, $^{77}$Br, $^{211}$At |
| 87 | CHOCH$_2$CH$_2$CH$_2$F |
| 87A | CHOCH$_2$CH$_2$F |
| 88 | CHOCH$_2$CH$_2$CH$_2$$^{18}$F |
| 88A | CHOCH$_2$CH$_2$$^{18}$F |
| 89 | 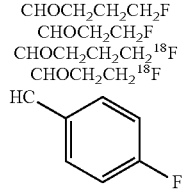 |
| 90 | 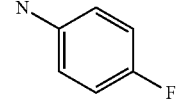 |
| 91 | 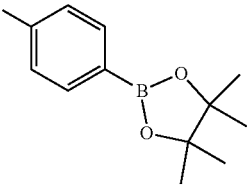 |
| 92 | 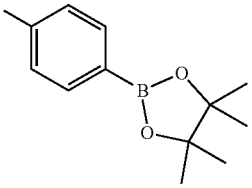 |

TABLE 2-continued
| Compound | R |
|---|---|
| 93 | 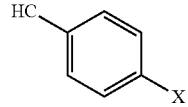<br>X = $^{18}$F, $^{123}$I, $^{124}$I, $^{125}$I, $^{131}$I, $^{76}$Br, $^{77}$Br, $^{211}$At |
| 94 | 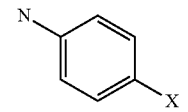 |
| 95<br>95A<br>96<br>96A | CHOCH$_2$CH$_2$F<br>CHOCH$_2$CH$_2$CH$_2$F<br>CHOCH$_2$CH$_2$$^{18}$F<br>CHOCH$_2$CH$_2$CH$_2$$^{18}$F |
| 97 | 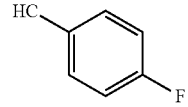 |
| 98 | 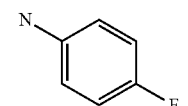 |
| 99 | 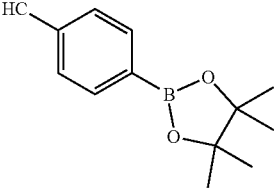 |
| 100 | 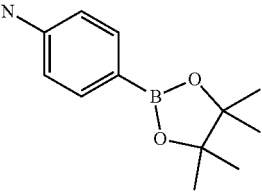 |
| 102 | 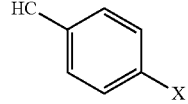<br>X = $^{18}$F, $^{123}$I, $^{124}$I, $^{125}$I, $^{131}$I, $^{76}$Br, $^{77}$Br, $^{211}$At |
| 103 | 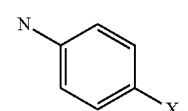<br>X = $^{18}$F, $^{123}$I, $^{124}$I, $^{125}$I, $^{131}$I, $^{76}$Br, $^{77}$Br, $^{211}$At |

Example 4: Characterization of Compounds 4-(4-Fluoro-3-(2-azaspiro[3.3]heptane-2-carbonyl)benzyl)phthalazin-1(2H)-one (10a). Following the general procedure, 10c was purified by flash chromatography to afford the desired product as a white foam (0.108 g, 30%). $^1$H NMR (500 MHz, CDCl$_3$) δ 11.38 (s, 1H), 8.48-8.46 (m, 1H), 7.77-7.70 (m, 3H), 7.49-7.47 (dd, J=2.0, 6.2 Hz, 1H), 7.30-7.27 (m, 1H), 6.98 (t, J=9.1 Hz, 1H), 4.28 (s, 2H), 4.10 (m, 2H), 3.95 (s, 2H), 2.21-2.15 (, 2H), 2.14-2.08 (m, 2H), 1.85-1.80 (m, 1H), 1.79-1.76 (m, 1H); $^{13}$C NMR (125 MHz, CDCl$_3$) δ 166.1, 161.0, 156.9 (d, $J_{C-F}$=249.6 Hz), 145.8, 134.1 (d, $J_{C-C-C-C-F}$=3.4 Hz), 133.7, 132.1 (d, $J_{C-C-C-F}$=8.3 Hz), 131.6, 130.2 (d, $J_{C-C-C-F}$=3.7 Hz), 129.7, 128.4, 127.2, 125.3, 122.7 (d, $J_{C-C-F}$=17.1 Hz), 116.3 (d, $J_{C-C-F}$=22.7 Hz), 63.4 (2×CH), 60.8, 38.1, 37.9, 33.1; LC-MS (ESI) m/z: (m/z): 378.15 [M+H].

4-(4-Fluoro-3-(2-oxa-6-azaspiro[3.3]heptane-6-carbonyl)benzyl)phthalazin-1(2H)-one (10b). Following the general procedure, 10b was purified by flash chromatography to afford the desired product as a white foam (0.2662 g, 70%). $^1$H NMR (500 MHz, CDCl$_3$) δ 11.54 (s, 1H), 8.47-8.45 (m, 1H), 7.77-7.69 (m, 3H), 7.49-7.47 (m, 1H), 7.34-7.31 (m, 1H), 7.01 (t, J=8.8 Hz, 1H), 4.81-4.79 (m, 2H), 4.74-4.72 (m, 2H), 4.30 (s, 2H), 4.27 (s, 2H), 4.20 (s, 2H); $^{13}$C NMR (125 MHz, CDCl$_3$) δ 166.2, 161.0, 157.0 (d, $J_{C-F}$=249.6 Hz), 145.6, 134.3 (d, $J_{C-C-C-C-F}$=3.5 Hz), 133.7, 132.6 (d, $J_{C-C-C-F}$=8.4 Hz), 131.6, 130.2 (d, $J_{C-C-C-F}$=3.3 Hz), 129.7, 128.4, 127.2, 125.1, 122.0 (d, $J_{C-C-F}$=16.6 Hz), 116.6 (d, $J_{C-C-F}$=25.5 Hz), 77.4, 77.2, 76.9, 60.6 (2×CH), 58.0, 38.1, 37.7; LC-MS (ESI) m/z: (m/z): 380.15 [M+H].

Tert-butyl 6-(2-fluoro-5-((4-oxo-3,4-dihydrophthalazin-1-yl)methyl)benzoyl)-2,6-diazaspiro[3.3]heptane-2-carboxylate (10c). Following the general procedure, 10b was purified by flash chromatography to afford the desired product as a white foam (0.324 g, 69%). $^1$H NMR (500 MHz, CDCl$_3$) δ 12.00 (s, 1H), 8.41 (m, 1H), 7.65 (m, 3H), 7.46 (dd, J=2.2, 4.1 Hz, 1H), 7.29 (m, 1H), 6.94 (t, J=9.2 Hz, 1H), 4.23 (d, J=7.2 Hz, 4H), 4.10 (s, 2H), 4.02 (d, J=9.5 Hz, 2H), 3.97 (d, J=9.4 Hz, 2H), 1.36 (s, 9H); $^{13}$C NMR (125 MHz, CDCl$_3$) δ 166.1, 161.1, 156.8 (d, $J_{C-F}$=250.1 Hz), 155.8, 145.4, 134.3 (d, $J_{C-C-C-C-F}$=3.6 Hz), 133.5, 132.5 (d, $J_{C-C-C-F}$=8.2 Hz), 131.4, 130.1 (d, $J_{C-C-C-F}$=3.5 Hz), 129.5, 128.2, 127.0, 125.0, 121.8 (d, $J_{C-C-F}$=16.3 Hz), 116.4 (d, $J_{C-C-F}$=21.8 Hz), 79.8, 61.0, 59.5, 58.6, 37.7, 32.5, 28.2; LC-MS (ESI) m/z: 479.09 [M+H], 379.08 [M-BOC+H].

4-(4-Fluoro-3-(2,6-diazaspiro[3.3]heptane-2-carbonyl)benzyl)phthalazin-1(2H)-one (10d). $^1$H NMR (500 MHz, CDCl$_3$) δ 8.45-8.44 (m, 1H), 7.75-7.72 (m, 2H), 7.71-7.68 (m, 1H), 7.47 (dd, J=2.2, 6.3 Hz, 1H), 7.48-7.28 (m, 1H), 6.98 (t, J=9.0 Hz, 1H), 4.26 (s, 2H), 4.23 (s, 2H), 4.14 (s, 2H), 3.84 (d, J=8.0 Hz, 2H), 3.75 (d, J=8.0 Hz, 2H), 3.34-3.23 (m, 1H); $^{13}$C NMR (125 MHz, CDCl$_3$) δ 166.1, 160.8, 158.9 (d, $J_{C-F}$=250.0 Hz), 145.6, 134.2 (d, $J_{C-C-C-C-F}$=3.6 Hz), 133.7, 132.5 (d, $J_{C-C-C-F}$=8.4 Hz), 131.6, 130.1 (d, $J_{C-C-C-F}$=3.6 Hz), 129.7, 128.4, 127.2, 125.1, 122.3 (d, $J_{C-C-F}$=17.0 Hz), 116.4 (d, $J_{C-C-F}$=22.9 Hz), 61.8, 61.7, 59.0, 57.4, 37.7; LC-MS (ESI) m/z: 479.09 [M+H], 379.21 [M+H].

4-(3-(6-(Cyclopropanecarbonyl)-2,6-diazaspiro[3.3]heptane-2-carbonyl)-4-fluorobenzyl)phthalazin-1(2H)-one (10e). Following the general procedure, 10e was purified by flash chromatography to afford the desired product as a white foam (0.257 g, 82%). $^1$H NMR (500 MHz, CDCl$_3$) δ 12.01 (s, 1H), 8.40-8.38 (m, 1H), 7.69-7.65 (m, 3H), 7.46-7.45 (m, 1H), 7.31-7.28 (m, 1H), 6.95 (t, J=8.9 Hz, 1H), 4.38 (d, J=8.9 Hz, 1H), 4.31 (d, J=8.6 Hz, 1H), 4.26 (s, 2H), 4.23 (s, 2H), 4.16, (s, 2H), 4.12 (d, J=10.5 Hz, 1H), 4.05 (d, J=10.3 Hz, 1H), 1.30-1.28 (m, 1H), 0.88 (d, J=3.0 Hz, 2H), 0.67 (d, J=5.7 Hz, 2H); $^{13}$C NMR (125 MHz, CDCl$_3$) δ 173.9, 166.0, 161.0, 156.9 (d, $J_{C-F}$=250.7 Hz), 145.4, 134.3 (d, $J_{C-C-C-C-F}$=3.4 Hz), 133.6, 132.7 (d, $J_{C-C-C-F}$=8.3 Hz), 131.5, 130.2 (d, $J_{C-C-C-F}$=3.6 Hz), 129.5, 128.3, 127.0, 125.0, 121.7 (d, $J_{C-C-F}$=16.6 Hz), 116.6 (d, $J_{C-C-F}$=23.0 Hz), 61.1, 60.0, 58.6, 58.1, 37.6, 32.6, 10.1, 7.5; LC-MS (ESI) m/z: (m/z): 447.04 [M+H].

4-(4-Fluoro-3-(I-azaspiro[3.3]heptane-1-carbonyl)benzyl)phthalazin-1(2H)-one (11a). Following the general procedure, 11a was purified by flash chromatography to afford the desired product as a white foam (0.189 g, 51%). (major rotamer reported)$^1$H NMR (500 MHz, CDCl$_3$) δ 12.00 (s, 1H), 8.41 (d, J=7.40 Hz, 1H), 7.71-7.66 (m, 3H), 7.38 (dd, J=1.7, 4.4 Hz, 1H), 7.30-7.28 (m, 1H), 6.95 (t, J=8.9 Hz, 1H), 5.15 (d, J=8.4 Hz, 1H), 4.79 (d, J=9.9 Hz, 1H), 4.23 (s, 2H), 4.22-4.21 (m, 1H), 4.05 (d, J=9.9 Hz, 1H), 3.89-3.84 (m, 2H), 2.48-2.45 (m, 2H), 1.38-1.35 (m, 1H), 0.90 (s, 2H), 0.67 (dd, J=2.7, 2.6 Hz, 2H); $^{13}$C NMR (125 MHz, CDCl$_3$) δ 173.7, 165.9, 161.1, 156.6 (d, $J_{C-F}$=248.5 Hz), 145.6, 134.3 (d, $J_{C-C-C-C-F}$=3.50 Hz), 133.6, 132.3 (d, $J_{C-C-C-F}$=8.1 Hz), 131.5, 129.7, 129.6 (d, $J_{C-C-C-F}$=3.7 Hz), 128.3, 127.0, 125.1, 122.7 (d, $J_{C-C-F}$=17.2 Hz), 116.3 (d, $J_{C-C-F}$=22.2 Hz), 63.3, 59.8, 58.6, 47.5, 37.7, 28.7, 10.5, 7.4; LC-MS (ESI) m/z: 447.17 [M+H].

Tert-butyl 1-(2-fluoro-5-((4-oxo-3,4-dihydrophthalazin-1-yl)methyl)benzoyl)-1,6-diazaspiro[3.3]heptane-6-carboxylate (11b). Following the general procedure, 11b was purified by flash chromatography to afford the desired product as a white foam (0.219 g, 98%). (major rotamer reported) $^1$H NMR (500 MHz, CDCl$_3$) δ 12.00 (s, 1H), 8.42-8.40 (m, 1H), 7.70-7.65 (m, 3H), 7.38 (dd, J=2.2, 4.0 Hz, 1H), 7.29-7.26 (m, 1H), 6.94 (t, J=8.9 Hz, 1H), 4.79 (d, J=9.1 Hz, 2H), 4.24 (s, 2H), 3.92 (d, J=9.3 Hz, 2H), 3.83 (t, J=7.4 Hz, 2H), 2.42 (t, J=7.3 Hz, 2H), 1.38 (s, 9H); $^{13}$C NMR (125 MHz, CDCl$_3$) δ 165.8, 161.2, 156.6 (d, $J_{C-F}$=249.2 Hz), 156.3, 145.7, 134.3 (d, $J_{C-C-C-C-F}$=2.9 Hz), 133.7, 132.2 (d, $J_{C-C-C-F}$=8.1 Hz), 131.5, 129.7, 129.6 (d, $J_{C-C-C-F}$=2.4 Hz), 128.3, 127.1, 125.1, 123.0 (d, $J_{C-C-F}$=17.6 Hz), 116.5 (d, $J_{C-C-F}$=22.4 Hz), 79.6, 63.5, 59.6, 47.4, 37.7, 28.5, 28.4; LC-MS (ESI) m/z: 501.12 [M+Na], 379.21 [M-BOC+H].

4-(4-Fluoro-3-(1,6-diazaspiro[3.3]heptane-1-carbonyl)benzyl)phthalazin-1(2H)-one (11c). (major rotamer reported)$^1$H NMR (500 MHz, CDCl$_3$) δ 11.76 (s, 1H), 8.46-8.44 (m, 1H), 7.71-7.68 (m, 3H), 7.39-7.38 (m, 1H), 7.26-7.24 (m, 1H), 6.97-6.93 (m, 2H), 4.26 (s, 2H), 3.79 (t, J=7.8 Hz, 2H), 3.17-3.11 (m, 2H), 2.31-2.28 (m, 2H), 2.07-2.03 (m, 2H), 1.86-1.82 (m, 1H), 1.70-1.63 (m, 1H); $^{13}$C NMR (125 MHz, CDCl$_3$) δ 165.7, 161.1, 156.5 (d, $J_{C-F}$=248.6 Hz), 145.8, 134.0 (d, $J_{C-C-C-C-F}$=3.5 Hz), 133.6, 131.5, 131.4 (d, $J_{C-C-C-F}$=7.6 Hz), 129.6, 129.5 (d, $J_{C-C-C-F}$=3.8 Hz), 128.3, 127.1, 125.2, 124.1 (d, $J_{C-C-F}$=18.2 Hz), 116.4 (d, $J_{C-C-F}$=22.6 Hz), 68.6, 46.6, 44.2, 37.9, 36.0, 33.7, 30.9, 13.2; LC-MS (ESI) m/z: 501.12 [M+Na], 378.28 [M+H].

4-(3-(6-(Cyclopropanecarbonyl)-1,6-diazaspiro[3.3]heptane-1-carbonyl)-4-fluorobenzyl)phthalazin-1(2H)-one (11d). Following the general procedure, 11d was purified by flash chromatography to afford the desired product as a white foam (0.180 g, 54%). (major rotamer reported)$^1$H NMR (500 MHz, CDCl$_3$) δ 12.00 (s, 1H), 8.41 (d, J=7.40 Hz, 1H), 7.71-7.66 (m, 3H), 7.38 (dd, J=1.7, 4.4 Hz, 1H), 7.30-7.28 (m, 1H), 6.95 (t, J=8.9 Hz, 1H), 5.15 (d, J=8.4 Hz, 1H), 4.79 (d, J=9.9 Hz, 1H), 4.23 (s, 2H), 4.22-4.21 (m, 1H), 4.05 (d, J=9.9 Hz, 1H), 3.89-3.84 (m, 2H), 2.48-2.45 (m, 2H), 1.38-1.35 (m, 1H), 0.90 (s, 2H), 0.67 (dd, J=2.7, 2.6 Hz, 2H); $^{13}$C NMR (125 MHz, CDCl$_3$) δ 173.7, 165.9, 161.1, 156.6 (d, $J_{C-F}$=248.5 Hz), 145.6, 134.3 (d, $J_{C-C-C-C-F}$=3.50 Hz), 133.6, 132.3 (d, $J_{C-C-C-F}$=8.1 Hz), 131.5, 129.7, 129.6 (d, $J_{C-C-C-F}$=3.7 Hz), 128.3, 127.0, 125.1, 122.7 (d, $J_{C-C-F}$=17.2 Hz), 116.3 (d, $J_{C-C-F}$=22.2 Hz), 63.3, 59.8, 58.6, 47.5, 37.7, 28.7, 10.5, 7.4; LC-MS (ESI) m/z: 447.17 [M+H].

4-(4-Fluoro-3-(2-azaspiro[3.5]nonane-2-carbonyl)benzyl)phthalazin-1(2H)-one (12a). Following the general procedure, 12a was purified by flash chromatography to afford the desired product as a white foam (0.185 g, 46%). $^1$H NMR (500 MHz, CDCl$_3$) δ 11.84 (s, 1H), 8.46-8.45 (m, 1H), 7.72-7.69 (m, 3H), 7.49-7.47 (m, 1H), 7.29-7.25 (m, 1H), 6.96 (t, J=8.7 Hz, 1H), 4.27 (s, 2H), 3.77 (s, 2H), 3.61 (s, 2H), 1.59 (bs, 4H), 1.41 (bs, 2H), 1.33 (bs, 4H); $^{13}$C NMR (125 MHz, CDCl$_3$) δ 166.5, 161.1, 156.9 (d, $J_{C-F}$=249.3 Hz), 145.7, 134.1 (d, $J_{C-C-C-C-F}$=3.4 Hz), 133.6, 132.0 (d, $J_{C-C-C-F}$=8.1 Hz), 131.5, 130.0 (d, $J_{C-C-C-F}$=3.6 Hz), 128.3, 127.1, 125.2, 122.7 (d, $J_{C-C-F}$=16.8 Hz), 116.4 (d, $J_{C-C-F}$=22.2 Hz), 61.5, 59.0, 37.8, 36.0, 35.7, 25.2, 23.0; LC-MS (ESI) m/z: 475.08 [M+H].

Tert-butyl 2-(2-fluoro-5-((4-oxo-3,4-dihydrophthalazin-1-yl)methyl)benzoyl)-2,7-diazaspiro[3.5]nonane-7-carboxylate (12b). Following the general procedure, 12b was purified by flash chromatography to afford the desired product as a white foam (0.350 g, 69%). $^1$H NMR (500 MHz, CDCl$_3$) δ 12.07 (s, 1H), 8.41-8.39 (m, 1H), 7.66-7.65 (m, 3H), 7.46 (d, J=5.5 Hz, 1H), 7.28-7.25 (m, 1H), 6.94 (t, J=9.3 Hz), 4.23 (s, 2H), 3.82 (s, 2H), 3.68 (s, 2H), 3.29-3.25 (m, 4H), 1.67-1.62 (m, 4H), 1.07 (s, 9H); $^{13}$C NMR (125 MHz, CDCl$_3$) δ 166.4, 161.0, 156.7 (d, $J_{C-F}$=249.5 Hz), 154.6, 145.5, 134.1 (d, $J_{C-C-C-C-F}$=3.3 Hz), 133.5, 132.1 (d, $J_{C-C-C-F}$=8.4 Hz), 131.3, 129.9 (d, $J_{C-C-C-F}$=3.9 Hz), 129.5, 128.2, 126.9, 125.0, 122.2 (d, $J_{C-C-F}$=17.1 Hz), 116.3 (d, $J_{C-C-F}$=22.7 Hz), 79.6, 60.5, 57.9, 40.6, 37.6, 34.9, 34.0, 28.3; LC-MS (ESI) m/z: 407.12 [M-BOC+H].

4-(4-Fluoro-3-(2,7-diazaspiro[3.5]nonane-2-carbonyl)benzyl)phthalazin-1(2H)-one (12c). $^1$H NMR (500 MHz, CDCl$_3$) δ 8.44 (d, J=6.5 Hz, 1H), 7.27-7.70 (m, 3H), 7.47-7.46 (m, 1H), 7.29-7.26 (m, 1H), 6.98 (t, J=9.1 Hz, 1H), 4.26 (s, 2H), 3.84 (s, 2H), 3.69 (s, 2H), 2.80 (bs, 2H), 2.76 (bs, 2H), 1.73 (bs, 4H); $^{13}$C NMR (125 MHz, CDCl$_3$) δ 166.5, 160.9, 156.8 (d, $J_{C-F}$=249.9 Hz), 145.7, 134.2 (d, $J_{C-C-C-C-F}$=3.6 Hz), 133.7, 132.3 (d, $J_{C-C-C-F}$=8.1 Hz), 131.6, 130.0 (d, $J_{C-C-C-F}$=3.9 Hz), 129.7, 128.4, 127.2, 125.2, 122.5 (d, $J_{C-C-F}$=17.2 Hz), 116.5 (d, $J_{C-C-F}$=22.6 Hz), 61.2, 58.7, 43.2, 37.8, 35.9, 34.3; LC-MS (ESI) m/z: 407.25 [M+H].

4-(3-(7-(Cyclopropanecarbonyl)-2,7-diazaspiro[3.5]nonane-2-carbonyl)-4-fluorobenzyl)phthalazin-1(2H)-one (12d). Following the general procedure, 12d was purified by flash chromatography to afford the desired product as a white foam (0.145 g, 68%). $^1$H NMR (500 MHz, CDCl$_3$) δ 12.1 (s, 1H), 7.67-7.62 (m, 3H), 7.44 (dd, J=1.9, 4.7 Hz, 1H), 7.27-7.24 (m, 1H), 6.94 (t, J=9.3 Hz, 1H), 4.22 (s, 2H), 3.83 (s, 2H), 3.69 (s, 2H), 3.47 (bs, 4H), 1.68-1.63 (m, 5H), 0.87-0.85 (m, 2H), 0.65-0.64 (m, 2H); $^{13}$C NMR (125 MHz, CDCl$_3$) δ 171.9, 166.4, 161.0, 156.7 (d, $J_{C-F}$=249.6 Hz), 145.4, 134.2 (d, $J_{C-C-C-C-F}$=3.6 Hz), 133.5, 132.3 (d, $J_{C-C-C-F}$=7.7 Hz), 131.4, 129.9 (d, $J_{C-C-C-F}$=3.6 Hz), 128.2, 129.5, 126.9, 125.0, 122.1 (d, $J_{C-C-F}$=17.3 Hz), 116.4 (d, $J_{C-C-F}$=22.1 Hz), 60.4, 58.0, 42.5, 39.3, 37.6, 35.8, 34.3, 10.9, 7.3; LC-MS (ESI) m/z: 475.08 [M+H].

4-(4-Fluoro-3-(1-azaspiro[3.5]nonane-1-carbonyl)benzyl)phthalazin-(2H)-one (13a). Following the general procedure, 13a was purified by flash chromatography to afford the desired product as a white foam (0.128 g, 32%). (major rotamer reported)$^1$H NMR (500 MHz, CDCl$_3$) δ 11.52 (s, 1H), 8.47-8.45 (m, 1H), 7.74-7.70 (m, 3H), 7.37-7.36 (m, 1H), 7.25-7.22 (m, 1H), 6.97-6.94 (m, 1H), 4.26 (s, 2H), 3.80 (t, J=8.0 Hz, 2H), 2.41-2.38 (m, 2H), 2.00 (t, J=7.2 Hz, 2H), 1.89 (s, 1H), 1.87 (s, 1H), 1.74-1.71 (m, 2H), 1.33-1.30 (m, 1H), 1.23-1.21 (m, 2H), 1.08-1.00 (m, 1H); $^{13}$C NMR (125 MHz, CDCl$_3$) δ 165.2, 160.0, 156.5 (d, $J_{C-F}$=247.9 Hz), 145.9, 134.0 (d, $J_{C-C-C-C-F}$=3.6 Hz), 133.7, 131.6, 131.3 (d, $J_{C-C-C-F}$=8.2 Hz), 129.7, 129.3 (d, $J_{C-C-C-F}$=3.7 Hz), 128.4, 127.2, 125.3, 124.4 (d, $J_{C-C-F}$=19.3 Hz), 116.4 (d, $J_{C-C-F}$=22.4 Hz), 71.2, 45.5 (2×CH), 43.2, 37.9, 36.7, 34.7, 27.8, 24.9, 22.7; LC-MS (ESI) m/z: 406.18 [M+H].

Tert-butyl 1-(2-fluoro-5-((4-oxo-3,4-dihydrophthalazin-1-yl)methyl)benzoyl)-1,7-diazaspiro[3.5]nonane-7-carboxylate (13b). Following the general procedure, 13b was purified by flash chromatography to afford the desired product as a white foam (0.409 g, 81%). (major rotamer reported)$^1$H NMR (500 MHz, CDCl$_3$) δ 12.09 (s, 1H), 8.38-8.36 (m, 1H), 7.64-7.61 (m, 3H), 7.30 (dd, J=2.2, 4.1 Hz, 1H), 7.22-7.19 (m, 1H), 6.89 (t, J=8.9 Hz, 1H), 4.20 (s, 2H), 4.06 (bs, 2H), 3.97 (t, J=7.3, 1H), 3.79 (t, J=7.46 Hz, 2H), 2.65 (bs, 2H), 2.52 (dt, J=4.2, 8.8 Hz, 2H), 2.01 (t, J=7.9 Hz, 2H), 1.75 (d, J=12.05 Hz, 2H), 1.37 (s, 9H); $^{13}$C NMR (125 MHz, CDCl$_3$) δ 165.7, 161.0, 156.2 (d, $J_{C-F}$=248.1 Hz), 154.5, 145.5, 134.0 (d, $J_{C-C-C-C-F}$=3.0 Hz), 133.4, 131.5 (d, $J_{C-C-C-F}$=8.0 Hz), 129.4, 129.1 (d, $J_{C-C-C-F}$=3.6 Hz), 128.1, 126.8, 125.6, 125.0, 123.5 (d, $J_{C-C-F}$=18.2 Hz), 116.0 (d, $J_{C-C-F}$=21.9 Hz), 79.4, 68.6, 45.4, 40.5, 37.6, 34.0, 28.3, 27.3; LC-MS (ESI) m/z: 529.04 [M+Na], 407.12 [M-BOC+H].

4-(4-Fluoro-3-(1,7-diazaspiro[3.5]nonane-1-carbonyl)benzyl)phthalazin-1(2H)-one (13c). (major rotamer reported)$^1$H NMR (500 MHz, CDCl$_3$) δ 8.44-8.42 (m, 1H), 7.75-7.66 (m, 3H), 7.26-7.18 (m, 2H), 7.05-6.93 (m, 1H), 4.24 (s, 2H), 4.05-4.02 (m, 1H), 3.84-3.81 (m, 1H), 3.14-3.11 (m, 1H), 3.02-2.97 (m, 1H), 2.88-2.86 (m, 1H), 2.63-2.51 (m, 2H), 2.13-2.05 (m, 2H), 1.87-1.79 (m, 1H), 1.74-1.72 (m, 1H), 1.61-1.56 (m, 1H); $^{13}$C NMR (125 MHz, CDCl$_3$) δ 165.8, 160.9, 156.4 (d, $J_{C-F}$=246.0 Hz), 145.6, 134.0 (d, $J_{C-C-C-C-F}$=3.0 Hz), 133.6, 131.5 (d, $J_{C-C-C-F}$=8.0 Hz), 129.8, 129.3 (d, $J_{C-C-C-F}$=4.1 Hz), 128.4, 127.1, 125.2, 124.2, 123.9 (d, $J_{C-C-F}$=18.1 Hz), 116.2 (d, $J_{C-C-F}$=20.8 Hz), 71.0, 45.4, 43.5, 42.8, 42.7, 36.4, 28.8; LC-MS (ESI) m/z: 407.12 [M+H].

4-(3-(7-(Cyclopropanecarbonyl)-1,7-diazaspiro[3.5]nonane-1-carbonyl)-4-fluorobenzyl)phthalazin-1(2H)-one (13d). Following the general procedure, 13d was purified by flash chromatography to afford the desired product as a white foam (0.074 g, 53%). (major rotamer reported)$^1$H NMR (500 MHz, CDCl$_3$) δ 11.54 (s, 1H), 8.46 (m, 1H), 7.74-7.68 (m, 3H), 7.36 (dd, J=2.2, 4.1 Hz, 1H), 7.27-7.25 (m, 1H), 6.98-6.95 (m, 1H), 4.25 (s, 2H), 4.13 (m, 2H), 3.88 (t, J=8.0 Hz, 2H), 3.10 (bs, 1H), 2.69-2.54 (m, 3H), 2.13 (t, J=7.7 Hz, 2H), 1.81 (m, 2H), 1.76-1.70 (m, 1H), 0.97-0.94 (m, 2H), 0.73-0.69 (m, 2H); $^{13}$C NMR (125 MHz, CDCl$_3$) δ 171.9, 165.5, 160.1, 156.4 (d, $J_{C-F}$=247.2 Hz), 145.7, 134.1 (d, $J_{C-C-C-C-F}$=3.5 Hz), 133.7, 131.6 (d, $J_{C-C-C-F}$=8.5 Hz), 129.6, 129.3 (d, $J_{C-C-C-F}$=3.6 Hz), 128.3, 127.1, 125.2, 124.3, 123.8 (d, $J_{C-C-F}$=18.3 Hz), 116.4 (d, $J_{C-C-F}$=22.1 Hz), 68.8, 45.5, 42.3, 37.8, 36.5, 34.2, 27.4, 11.1, 7.4; LC-MS (ESI) m/z: 475.08 [M+H], 496.98 [M+Na].

4-(4-Fluoro-3-(6-azaspiro[3.4]octane-6-carbonyl)benzyl) phthalazin-1(2H)-one (14a). Following the general procedure, 14a was purified by flash chromatography to afford the desired product as a white foam (0.263 g, 54%). (mixture of two rotamers reported)$^1$H NMR (500 MHz, CDCl$_3$) δ 12.30

(s, 1H), 8.40-8.37 (m, 1H), 7.64-7.62 (m, 3H), 7.32-7.29 (m, 1H), 7.25-7.19 (m, 1H), 6.95-6.88 (m, 1H), 4.23-4.22 (m, 2H), 3.55-3.51 (m, 2H), 3.19-3.17 (t, J=6.8 Hz, 1H), 3.09 (s, 1H), 1.99-1.95 (m, 1H), 1.86-1.74 (m, 7H); $^{13}$C NMR (125 MHz, CDCl$_3$) δ 164.9, 164.8, 161.1, 156.0 (d, $J_{C-F}$=247.8 Hz), 145.6, 134.1 (d, $J_{C-C-C-C-F}$=3.4 Hz), 134.0 (d, $J_{C-C-C-C-F}$=3.4 Hz), 133.4, 133.3, 131.3, 131.1 (d, $J_{C-C-C-F}$=8.1 Hz), 131.0 (d, $J_{C-C-C-F}$=8.1 Hz), 129.4, 128.7 (d, $J_{C-C-C-F}$=3.6 Hz), 128.6 (d, $J_{C-C-C-F}$=3.6 Hz), 128.1, 128.0, 126.9, 125.5 (d, $J_{C-C-F}$=17.8 Hz), 125.4 (d, $J_{C-C-F}$=17.8 Hz), 125.1, 116.1 (d, $J_{C-C-F}$=21.9 Hz), 116.0 (d, $J_{C-C-F}$=21.9 Hz), 58.7, 57.0, 46.3, 44.7, 44.5, 43.7, 37.7, 37.6, 36.2, 31.1, 30.5, 15.9, 15.7; LC-MS (ESI) m/z: 392.16 [M+H].

Tert-butyl 2-(2-fluoro-5-((4-oxo-3,4-dihydrophthalazin-1-yl)methyl)benzoyl)-2,6-diazaspiro[3.4]octane-6-carboxylate (14b). Following the general procedure, 14b was purified by flash chromatography to afford the desired product as a white foam (0.334 g, 72%). (mixture of two rotamers reported)$^1$H NMR (500 MHz, CDCl$_3$) δ 12.08-12.06 (m, 1H), 8.39-8.37 (m, 1H), 7.68-7.62 (m, 3H), 7.31-7.29 (m, 1H), 7.26-7.22 (m, 1H), 6.96-6.90 (m, 1H), 4.22-4.21 (m, 2H), 3.88-3.87 (m, 2H), 3.77-3.73 (m, 2H), 3.70-3.66 (m, 2H), 3.60 (t, J=6.94 Hz, 1H), 3.34-3.33 (m, 2H), 3.25 (t, J=6.90 Hz, 1H), 2.08 (t, J=7.2 Hz, 1H), 2.00 (t, J=6.7 Hz, 1H), 1.36-1.33 (m, 9H); $^{13}$C NMR (125 MHz, CDCl$_3$) δ 165.1, 165.0, 161.1 (2×CH), 156.2 (d, $J_{C-F}$=247.6 Hz), 156.1 (d, $J_{C-F}$=247.6 Hz), 145.5 (2×CH), 134.4 (d, $J_{C-C-C-C-F}$=3.4 Hz), 134.3 (d, $J_{C-C-C-C-F}$=3.4 Hz), 133.5, 131.6 (d, $J_{C-C-C-F}$=7.9 Hz), 131.4 (d, $J_{C-C-C-F}$=7.9 Hz), 129.5, 128.9, 127.0, 125.1 (d, $J_{C-F}$=17.3 Hz), 125.0 (d, $J_{C-F}$=17.2 Hz), 116.2 (d, $J_{C-C-F}$=21.9 Hz), 116.2 (d, $J_{C-C-F}$=21.9 Hz), 79.8, 79.7, 57.9, 56.8, 55.1, 50.4, 46.3, 44.6, 39.7, 38.7, 37.7, 36.3, 34.6, 28.3 (2×CH); LC-MS (ESI) m/z: 515.01 [M+Na], 393.10 [M-BOC+H].

4-(4-Fluoro-3-(2,6-diazaspiro[3.4]octane-6-carbonyl)benzyl)phthalazin-1(2H)-one (14c). (mixture of two rotamers reported)$^1$H NMR (500 MHz, CDCl$_3$) δ 8.44 (d, J=7.0 Hz, 1H), 7.76-7.68 (m, 3H), 7.36-7.32 (m, 1H), 7.26-7.24 (m, 1H), 7.01-6.96 (m, 1H), 4.26-4.25 (m, 2H), 3.72 (s, 1H), 3.62-3.59 (m, 3H), 3.51 (s, 2H), 3.41 (s, 1H), 3.27 (t, J=6.8 Hz, 1H), 2.13-2.08 (m, 2H); $^{13}$C NMR (125 MHz, CDCl$_3$) δ 165.3, 165.0, 160.1, 156.4 (d, $J_{C-F}$=247.6 Hz), 156.3 (d, $J_{C-F}$=246.7 Hz), 145.6, 145.2, 134.3 (d, $J_{C-C-C-C-F}$=3.4 Hz), 134.7 (d, $J_{C-C-C-C-F}$=3.7 Hz), 131.6, 131.5 (d, $J_{C-C-C-F}$=7.4 Hz), 131.4 (d, $J_{C-C-C-F}$=7.8 Hz), 129.8, 129.7 (2×CH), 129.6, 129.0, (2×CH), 128.4, 127.2, 125.1 (d, $J_{C-F}$=17.3 Hz), 125.2 (d, $J_{C-F}$=18.1 Hz), 124.9, 116.2 (d, $J_{C-C-F}$=21.9 Hz), 116.2 (d, $J_{C-C-F}$=21.9 Hz), 57.4, 56.5, 55.8, 55.5, 46.5, 45.1, 44.5, 43.9, 37.8, 37.5, 36.4, 34.6; LC-MS (ESI) m/z: 393.23 [M+H].

4-(3-(6-(Cyclopropanecarbonyl)-2,6-diazaspiro[3.4]octane-2-carbonyl)-4-fluorobenzyl)phthalazin-1(2H)-one (14d). Following the general procedure, 14d was purified by flash chromatography to afford the desired product as a white foam (0.119 g, 88%). (mixture of two rotamers reported)$^1$H NMR (500 MHz, CDCl$_3$) δ 11.99 (m, 1H), 8.40-8.38 (m, 1H), 7.70-7.65 (m, 3H), 7.32-7.30 (m, 1H), 7.27-7.25 (m, 1H), 6.99-6.94 (m, 1H), 4.24-4.22 (m, 2H), 4.12-4.07 (m, 1H), 4.01-3.96 (m, 1H), 3.90-3.71 (m, 3H), 3.67-3.62 (m, 1H), 3.40 (s, 1H), 3.36 (s, 1H), 3.31 (t, J=6.71 Hz, 1H), 2.15 (m, 1H), 2.09 (t, J=6.8 Hz, 1H), 1.37-1.27 (m, 1H), 0.92-0.90 (m, 1H), 0.89-0.87 (m, 1H), 0.70-0.67 (m, 2H); $^{13}$C NMR (125 MHz, CDCl$_3$) δ 174.2 (2×CH), 165.2, 165.0, 161.1 (2×CH), 156.2 (d, $J_{C-F}$=249.1 Hz), 156.1 (d, $J_{C-F}$=249.1 Hz), 145.6, 145.5, 134.5 (d, $J_{C-C-C-C-F}$=3.5 Hz), 134.4 (d, $J_{C-C-C-C-F}$=3.5 Hz), 133.63, 133.60, 131.7 (d, $J_{C-C-C-F}$=8.9 Hz), 131.5 (d, $J_{C-C-C-F}$=8.9 Hz), 129.57, 129.0 (2×C), 128.3 (2×CH), 127.1, 125.1, 125.0 (d, $J_{C-C-C-F}$=2.5 Hz), 124.9 (d, $J_{C-C-C-F}$=17.4 Hz), 124.8 (d, $J_{C-C-C-F}$=17.4 Hz), 116.3 (d, $J_{C-C-F}$=21.8 Hz), 116.2 (d, $J_{C-C-F}$=21.8 Hz), 59.4, 58.8, 57.1, 56.9, 56.4, 55.2, 46.4, 44.6, 39.9, 38.9, 37.7, 36.4, 34.8, 10.1 (2×CH), 7.5; LC-MS (ESI) m/z: 461.06 [M+H].

4-(4-Fluoro-3-(2-azaspiro[4.4]nonane-2-carbonyl)benzyl)phthalazin-1(2H)-one (15a). Following the general procedure, 15a was purified by flash chromatography to afford the desired product as a white foam (0.292 g, 72%). (mixture of rotamers reported)$^1$H NMR (500 MHz, CDCl$_3$) δ 11.85 (s, 1H), 8.46-8.44 (m, 1H), 7.72-7.68 (m, 3H), 7.36-7.32 (m, 1H), 7.27-7.23 (m, 1H), 6.97 (dt, J=1.94, 7.0 Hz, 1H), 4.27 (s, 2H), 3.63 (t, J=7.3 Hz, 1H), 3.29 (t, J=6.9 Hz, 1H), 3.02 (s, 1H), 1.79 (t, J=7.1 Hz, 1H), 1.73 (t, J=7.1 Hz, 1H), 1.65-1.63 (m, 2H), 1.61-1.59 (m, 2H), 1.51-1.41 (m, 5H); $^{13}$C NMR (125 MHz, CDCl$_3$) δ 165.2, 165.0, 161.1, 156.2 (d, $J_{C-F}$=247.3 Hz), 156.1 (d, $J_{C-F}$=247.3 Hz), 145.7, 134.2 (d, $J_{C-C-C-C-F}$=3.2 Hz), 133.6, 133.5, 131.6 (d, $J_{C-C-C-F}$=8.6 Hz), 131.5, 131.1 (d, $J_{C-C-C-F}$=7.9 Hz), 129.6, 128.8 (t, $J_{C-C-C-F}$=3.7 Hz), 128.3, 127.1, 125.7 (d, $J_{C-C-F}$=18.2 Hz), 125.6 (d, $J_{C-C-F}$=18.4 Hz), 116.2 (d, $J_{C-C-F}$=22.0 Hz), 116.1 (d, $J_{C-C-F}$=22.0 Hz), 59.0 (2×CH), 57.2, 49.7, 48.5, 47.3 (2×CH), 45.5, 37.9, 37.8, 37.5, 36.7, 36.5, 36.1, 24.8, 24.6; LC-MS (ESI) m/z: 406.18 [M+H].

Tert-butyl 7-(2-fluoro-5-((4-oxo-3,4-dihydrophthalazin-1-yl)methyl)benzoyl)-2,7-diazaspiro[4.4]nonane-2-carboxylate (15b). Following the general procedure, 15b was purified by flash chromatography to afford the desired product as a white foam (0.411 g, 79%). (mixture of two rotamers reported)$^1$H NMR (500 MHz, CDCl$_3$) δ 12.19 (s, 1H), 8.32-8.31 (m, 1H), 7.59-7.57 (m, 3H), 7.29-7.27 (m, 1H), 7.19 (t, J=8.42 Hz, 1H), 4.17 (s, 2H), 3.61-3.57 (s, 1H), 3.49-3.42 (m, 1H), 3.34-3.26 (m, 3H), 3.19-3.04 (m, 3H), 1.79-1.72 (m, 3H), 1.67-1.65 (m, 1H), 1.33-1.31 (m, 9H); $^{13}$C NMR (125 MHz, CDCl$_3$) δ 165.1, 164.9, 161.0 (2×C), 156.1 (d, $J_{C-F}$=247.2 Hz), 156.0 (d, $J_{C-F}$=248.2 Hz), 154.2 (2×C), 145.5, 145.4, 134.3 (d, $J_{C-C-C-C-F}$=3.3 Hz), 134.2 (d, $J_{C-C-C-C-F}$=3.3 Hz), 133.5 (2×C), 131.6 (d, $J_{C-C-C-F}$=8.3 Hz), 129.3, 128.9 (d, $J_{C-C-C-F}$=3.7 Hz), 128.0, 126.7, 125.3, 124.9 (d, $J_{C-C-F}$=17.7 Hz), 116.1 (d, $J_{C-C-F}$=22.2 Hz), 116.0 (d, $J_{C-C-F}$=22.3 Hz), 79.2, 79.1, 56.2, 54.7, 54.5, 54.2, 54.1, 50.0, 48.7, 47.8, 47.4, 44.8, 44.5, 44.4, 37.4, 34.8, 34.7, 34.3, 34.2, 33.5, 33.4, 28.4, 28.2; LC-MS (ESI) m/z: 407.12 [M-BOC+H].

4-(4-Fluoro-3-(2,7-diazaspiro[4.4]nonane-2-carbonyl)benzyl)phthalazin-1(2H)-one (15c). (mixture of two rotamers reported)$^1$H NMR (500 MHz, CDCl$_3$) δ 8.45 (d, J=7.8 Hz, 1H), 7.74-7.68 (m, 3H), 7.35-7.34 (m, 1H), 7.78-7.22 (m, 1H), 7.01-6.96 (m, 1H), 4.26-4.25 (m, 2H), 3.71-3.62 (m, 1H), 3.58-3.51 (m, 1H), 3.36-3.30 (m, 1H), 3.18 (q, J=10.4, 12.0 Hz, 1H), 3.06-2.96 (m, 2H), 2.94-2.84 (m, 1H), 2.80-2.78 (m, 1H), 1.93 (t, J=7.3 Hz, 1H), 1.87-1.82 (m, 1H), 1.76-1.64 (m, 2H); $^{13}$C NMR (125 MHz, CDCl$_3$) δ 165.2, 165.1, 161.9, 156.3 (d, $J_{C-F}$=246.4 Hz), 145.6, 145.4, 134.2 (d, $J_{C-C-C-C-F}$=3.5 Hz), 133.9 (d, $J_{C-C-C-C-F}$=3.5 Hz), 133.5 (2×C), 131.5 (d, $J_{C-C-C-F}$=3.6 Hz), 131.3 (d, $J_{C-C-C-F}$=8.3 Hz), 129.7 (2×C), 129.4 (d, $J_{C-C-C-F}$=3.8 Hz), 128.9 (d, $J_{C-C-C-F}$=3.8 Hz), 128.4, 127.1, 125.6 (d, $J_{C-C-F}$=18.2 Hz), 125.0 (d, $J_{C-C-F}$=23.2 Hz), 116.4 (d, $J_{C-C-F}$=21.9 Hz), 116.3 (d, $J_{C-C-F}$=21.8 Hz), 58.3, 56.8, 56.3, 56.1, 49.7, 48.6, 47.2, 46.4, 46.3, 44.4, 37.9, 37.6, 37.0, 36.4, 36.1, 35.2; LC-MS (ESI) m/z: 407.25 [M+H].

4-(3-(7-(Cyclopropanecarbonyl)-2,7-di zaspiro[4.4]nonane-2-carbonyl)-4-fluorobenzyl)phthalazin-1(2H)-one (15d). Following the general procedure, 15d was purified by flash chromatography to afford the desired product as a white foam (0.056 g, 41%). (mixture of rotamers reported) $^1$H NMR (500 MHz, CDCl$_3$) δ 11.89-11.83 (m, 1H), 8.42-8.41 (m, 1H), 7.70-7.67 (m, 3H), 7.35-7.34 (m, 1H), 7.30-7.26 (m, 1H), 6.99-6.95 (m, 1H), 4.25 (s, 2H), 3.73-3.67 (m, 2H), 3.59-3.48 (m, 3H), 3.42-3.35 (m, 2H), 3.18 (s, 1H), 2.20-1.77 (m, 4H), 1.57-1.48 (m, 1H), 0.96-0.89 (m, 2H), 0.74-0.69 (m, 2H); $^{13}$C NMR (125 MHz, CDCl$_3$) δ 172.6, 172.5, 172.4, 165.2, 165.3, 165.2, 165.1, 161.0 (3×C), 156.3 (d, $J_{C-F}$=247.8 Hz), 156.2 (d, $J_{C-F}$=247.3 Hz), 145.6, 145.5 (2×C), 134.3 (d, $J_{C-C-C-C-F}$=3.6 Hz), 134.3 (d, $J_{C-C-C-C-F}$=3.7 Hz), 133.6, 131.6 (d, $J_{C-C-C-F}$=8.6 Hz), 131.5 (d, $J_{C-C-C-F}$=8.6 Hz), 131.5, 129.5, 128.2 (d, $J_{C-C-C-F}$=3.8 Hz), 128.8 (d, $J_{C-C-C-F}$=3.8 Hz), 128.3, 127.0, 125.2 (d, $J_{C-C-F}$=17.2 Hz), 125.1 (d, $J_{C-C-F}$=17.2 Hz), 116.4 (d, $J_{C-C-F}$=22.1 Hz), 116.2 (d, $J_{C-C-F}$=22.1 Hz), 55.4, 55.3, 55.6, 55.0, 54.6, 54.1, 49.4, 48.0, 47.5, 46.7, 46.2, 45.6, 45.4, 45.1, 45.0, 44.9, 37.7, 37.6, 35.2, 34.8, 34.7, 33.8, 33.7, 33.5, 32.9, 12.5, 12.2, 12.1, 7.7, 7.6, 7.5; LC-MS (ESI) m/z: 475.08 [M+H].

4-(4-Fluoro-3-(2-azaspiro[4.5]decane-2-carbonyl)benzyl)phthalazin-1(2H)-one (16a). Following the general procedure, 16a was purified by flash chromatography to afford the desired product as a white foam (0.208 g, 50%). (mixture of two rotamers reported)$^1$H NMR (500 MHz, CDCl$_3$) δ 11.33 (s, 1H), 8.48-8.45 (m, 1H), 7.76-7.69 (m, 3H), 7.36-7.29 (m, 1H), 7.28-7.23 (m, 1H), 7.02-6.97 (m, 1H), 4.28-4.27 (m, 2H), 3.64 (t, J=7.3 Hz, 1H), 3.43 (s, 1H), 3.30 (t, J=7.1 Hz, 1H), 3.01 (s, 1H), 1.75 (t, J=7.4 Hz, 1H), 1.68 (t, J=7.1 Hz, 1H), 1.51-1.32 (m, 9H), 1.26-1.23 (m, 1H); $^{13}$C NMR (125 MHz, CDCl$_3$) δ 165.2, 165.1, 160.9, 156.3 (d, $J_{C-F}$=247.7 Hz), 156.2 (d, $J_{C-F}$=247.7 Hz), 145.8, 134.2 (d, $J_{C-C-C-C-F}$=3.4 Hz), 134.1 (d, $J_{C-C-C-C-F}$=3.4 Hz), 133.7 (2×CH), 131.6, 131.2 (d, $J_{C-C-C-F}$=8.0 Hz), 129.7, 128.9 (d, $J_{C-C-C-F}$=4.3 Hz), 128.8 (d, $J_{C-C-C-F}$=3.9 Hz), 129.7, 128.9 (d, $J_{C-C-C-F}$=8.2 Hz), 129.6, 128.8 (d, $J_{C-C-C-F}$=3.2 Hz), 128.7 (d, $J_{C-C-C-F}$=3.2 Hz), 128.4 (2×CH), 127.2, 125.9 (d, $J_{C-C-F}$=18.5 Hz), 125.8 (d, $J_{C-C-F}$=18.5 Hz), 125.3, 116.5 (d, $J_{C-C-F}$=22.0 Hz), 116.4 (d, $J_{C-C-F}$=22.1 Hz), 58.2, 56.3, 46.2 (2×CH), 44.4, 42.6, 41.2, 38.0, 37.9, 37.1, 35.6, 35.4, 35.2, 34.8, 26.2, 26.1, 23.4, 23.3; LC-MS (ESI) m/z: 420.20 [M+H].

Tert-butyl 2-(2-fluoro-5-((4-oxo-3,4-dihydrophthalazin-1-yl)methyl)benzoyl)-2,8-diazaspiro[4.5]decane-8-carboxylate (16b). Following the general procedure, 16b was purified by flash chromatography to afford the desired product as a white foam (0.427 g, 79%). (mixture of two rotamers reported)$^1$H NMR (500 MHz, CDCl$_3$) δ 12.09 (s, 1H), 8.39-8.38 (m, 1H), 7.64-7.63 (m, 3H), 7.31-7.21 (m, 2H), 6.95-6.90 (m, 1H), 4.22-4.21 (m, 2H), 3.61 (t, J=7.2 Hz, 1H), 3.49-3.44 (m, 2H), 3.32-3.26 (m, 2H), 3.24-3.19 (m, 1H), 3.17-3.14 (m, 1H), 3.02 (s, 1H), 1.75 (t, J=7.5 Hz, 1H), 1.68 (t, J=6.8 Hz, 1H), 1.52-1.40 (m, 4H), 1.38 (s, 4H), 1.36 (s, 5H); $^{13}$C NMR (125 MHz, CDCl$_3$) δ 165.2, 165.0, 161.1, 161.0, 156.0 (d, $J_{C-F}$=247.7 Hz), 155.9 (d, $J_{C-F}$=247.7 Hz), 154.6, 154.5, 145.5, 145.4, 134.3 (d, $J_{C-C-C-C-F}$=3.6 Hz), 134.2 (d, $J_{C-C-C-C-F}$=3.6 Hz), 133.4, 133.3, 131.3, 131.2 (d, $J_{C-C-C-F}$=8.5 Hz), 131.1 (d, $J_{C-C-C-F}$=8.5 Hz), 129.4, 128.7 (d, $J_{C-C-C-F}$=3.9 Hz), 128.6 (d, $J_{C-C-C-F}$=3.9 Hz), 128.2, 128.1, 126.9, 125.4 (d, $J_{C-C-F}$=18.5 Hz), 125.3 (d, $J_{C-C-F}$=18.5 Hz), 125.0, 116.2 (d, $J_{C-C-F}$=21.9 Hz), 116.0 (d, $J_{C-C-F}$=21.9 Hz), 79.5, 79.4, 57.1, 55.0, 45.7, 45.6, 44.0, 40.9, 39.6, 37.7, 37.6, 36.1, 34.4, 34.1, 33.7, 28.3 (2×C); LC-MS (ESI) m/z: 421.14 [M-BOC+H].

4-(4-Fluoro-3-(2,8-diazaspiro[4.5]decane-2-carbonyl)benzyl)phthalazin-1(2H)-one (16c). (mixture of two rotamers reported)$^1$H NMR (500 MHz, CDCl$_3$) δ 8.42-8.40 (m, 1H), 7.68-7.66 (m, 3H), 7.31-7.23 (m, 2H), 6.98-6.93 (m, 1H), 4.24-4.23 (m, 2H), 3.62 (t, J=7.0), 3.46 (s, 1H), 3.28 (t, J=7.0 Hz, 1H), 3.04 (s, 1H), 2.88-2.85 (m, 1H), 2.80-2.76 (m, 2H), 2.63-2.59 (m, 1H), 1.77 (t, J=7.4 Hz, 1H), 1.70 (t, J=7.0 Hz, 1H), 1.56-1.50 (m, 2H), 1.48-1.43 (m, 1H), 1.41-1.36 (m, 1H); $^{13}$C NMR (125 MHz, CDCl$_3$) δ 165.2, 165.1, 161.0, 156.2 (d, $J_{C-F}$=247.2 Hz), 155.1 (d, $J_{C-F}$=247.2 Hz), 145.5, 134.2, 133.5 (2×C), 131.4, 131.2 (d, $J_{C-C-C-C-F}$=3.5 Hz), 131.1 (d, $J_{C-C-C-C-F}$=3.4 Hz), 129.6, 128.8 (d, $J_{C-C-C-F}$=8.8 Hz), 128.7 (d, $J_{C-C-C-F}$=8.8 Hz), 128.3, 127.0, 125.7, 125.6 (d, $J_{C-C-F}$=18.3 Hz), 125.1, 116.2 (d, $J_{C-C-F}$=21.9 Hz), 116.1 (d, $J_{C-C-F}$=21.9 Hz), 57.8, 55.7, 45.7, 44.1, 43.7, 43.4, 41.2, 39.9, 37.8, 37.0, 35.7, 35.0; LC-MS (ESI) m/z: 421.13 [M+H].

4-(3-(8-(Cyclopropanecarbonyl)-2,8-diazaspiro[4.5]decane-2-carbonyl)-4-fluorobenzyl)phthalazin-1(2H)-one (16d). Following the general procedure, 16d was purified by flash chromatography to afford the desired product as a white foam (0.158 g, 93%). (mixture of two rotamers reported)$^1$H NMR (500 MHz, CDCl$_3$) δ 11.97-11.96 (m, 1H), 8.41-8.39 (m, 1H), 7.69-7.65 (m, 3H), 7.32-7.31 (m, 1H), 7.28-7.25 (m, 1H), 6.98-6.95 (m, 1H), 4.24 (s, 2H), 3.76 (bs, 1H), 3.65 (t, J=7.21 Hz, 1H), 3.50 (m, 2H), 3.40 (bs, 2H), 3.33 (t, J=6.8 Hz, 1H), 3.07 (s, 1H), 1.81 (m, 1H), 1.74 (t, J=7.03 Hz, 1H), 1.70-1.63 (m, 1H), 1.54-1.42 (4H), 0.92-0.89 (2H), 0.67-0.66 (2H); $^{13}$C NMR (125 MHz, CDCl$_3$) δ 171.9, 165.4, 165.1, 161.1, 161.0, 156.2 (d, $J_{C-F}$=247.7 Hz), 156.1 (d, $J_{C-F}$=247.7 Hz), 145.6 (2×CH), 134.4 (d, $J_{C-C-C-C-F}$=3.1 Hz), 134.3 (d, $J_{C-C-C-C-F}$=3.1 Hz), 133.6 (2×CH), 131.5 (d, $J_{C-C-C-F}$=8.3 Hz), 131.4 (d, $J_{C-C-C-F}$=8.2 Hz), 129.6, 128.8 (d, $J_{C-C-C-F}$=3.2 Hz), 128.7 (d, $J_{C-C-C-F}$=3.2 Hz), 128.3 (2×CH), 127.1, 125.5 (d, $J_{C-C-F}$=17.5 Hz), 125.4 (d, $J_{C-C-F}$=17.3 Hz), 125.1, 116.3 (d, $J_{C-C-F}$=22.1 Hz), 116.2 (d, $J_{C-C-F}$=22.1 Hz), 57.4, 55.1, 45.8 (2×C), 44.2, 43.1, 41.3, 40.1, 39.8, 37.8, 36.5, 35.4, 35.2, 34.3, 34.5, 11.1, 11.0, 7.4; LC-MS (ESI) m/z: 489.10 [M+H].

4-(4-Fluoro-3-(3-azaspiro[5.5]undecane-3-carbonyl)benzyl)phthalazin-1(2H)-one (17a). Following the general procedure, 17a was purified by flash chromatography to afford the desired product as a white foam (0.238 g, 55%). $^1$H NMR (500 MHz, CDCl$_3$) δ 12.29 (s, 1H), 8.38-8.36 (m, 1H), 7.63-7.61 (m, 3H), 7.25-7.24 (m, 1H), 7.21-7.18 (m, 1H), 6.90-6.87 (t, J=8.8 Hz, 1H), 4.20 (s, 2H), 3.62-3.60 (m, 2H), 3.10 (bs, 2H), 1.41-1.39 (m, 2H), 1.29-1.27 (m, 12H); $^{13}$C NMR (125 MHz, CDCl$_3$) δ 164.7, 161.2, 156.0 (d, $J_{C-F}$=247.2 Hz), 145.7, 134.2 (d, $J_{C-C-C-C-F}$=3.6 Hz), 133.5, 131.3, 130.9 (d, $J_{C-C-C-F}$=7.8 Hz), 129.5, 128.8 (d, $J_{C-C-C-F}$=3.7 Hz), 128.2, 125.1, 124.8 (d, $J_{C-C-F}$=18.6 Hz), 116.0 (d, $J_{C-C-F}$=21.8 Hz), 43.1, 37.8, 37.7, 36.4, 36.0, 35.7, 31.4, 26.6, 21.3; LC-MS (ESI) m/z: 434.09 [M+H].

Tert-butyl 9-(2-fluoro-5-((4-oxo-3,4-dihydrophthalazin-1-yl)methyl)benzoyl)-3,9-diazaspiro[5.5]undecane-3-carboxylate (17b). Following the general procedure, 17b was purified by flash chromatography to afford the desired product as a white foam (0.215 g, 40%). $^1$H NMR (500 MHz, CDCl$_3$) δ 12.01 (s, 1H), 8.43-8.41 (m, 1H), 7.59-7.57 (m, 3H), 7.28-7.26 (m, 1H), 7.19 (bs, 1H), 6.87 (t, J=8.3 Hz, 1H), 4.16 (s, 2H), 7.70-7.67 (m, 3H), 7.27-7.26 (m, 1H), 7.25-7.23 (m, 1H), 6.94 (t, J=8.6 Hz, 1H), 4.24 (s, 2H), 3.68 (s, 2H), 3.34-3.31 (m, 4H), 3.19 (s, 2H), 1.51 (t, J=5.2 Hz, 2H), 1.44 (m, 4H), 1.39 (s, 9H), 1.35 (m, 2H); $^{13}$C NMR (125 MHz, CDCl$_3$) δ 164.9, 161.1, 158.1 (d, $J_{C-F}$=247.6 Hz), 154.9, 145.7, 134.4 (d, $J_{C-C-C-C-F}$=3.4 Hz), 133.6, 131.5, 131.1 (d, $J_{C-C-C-F}$=8.0 Hz), 129.6, 128.9 (d, $J_{C-C-C-F}$=4.3 Hz), 128.3, 127.1, 124.7 (d, $J_{C-C-F}$=18.3 Hz), 116.2 (d, $J_{C-C-F}$=21.9 Hz), 79.5, 42.9, 39.3, 37.8, 37.3, 35.8, 34.8, 30.4, 28.5; LC-MS (ESI) m/z: 557.09 [M+Na], 435.15 [M-BOC+H].

4-(4-Fluoro-3-(3,9-diazaspiro[5.5]undecane-3-carbonyl) benzyl)phthalazin-1(2H)-one (17c). $^1$H NMR (500 MHz, CDCl$_3$) δ 8.44-8.42 (m, 1H), 7.71-7.66 (m, 3H), 7.27-7.22 (m, 2H), 6.96 (t, J=8.8 Hz, 1H), 4.25 (s, 2H), 3.69 (t, J=5.4 Hz, 2H), 3.18 (bs, 2H), 2.81-2.77 (m, 4H), 1.55-1.53 (m, 2H), 1.47-1.44 (m, 4H), 1.37 (bs, 2H); $^{13}$C NMR (125 MHz, CDCl$_3$) δ 164.9, 161.0, 158.1 (d, $J_{C-F}$=246.9 Hz), 145.6, 134.3 (d, $J_{C-C-C-C-F}$=3.1 Hz), 133.6, 131.5, 131.0 (d, $J_{C-C-C-F}$=7.8 Hz), 129.6, 128.9 (d, $J_{C-C-C-F}$=3.7 Hz), 128.4, 127.1, 125.1, 124.8 (d, $J_{C-C-F}$=18.4 Hz), 116.0 (d, $J_{C-C-F}$=22.0 Hz), 42.9, 41.8, 37.8, 37.6, 36.5, 35.6, 30.6; LC-MS (ESI) m/z: 435.15 [M+H].

4-(3-(9-(Cyclopropanecarbonyl)-3,9-diazaspiro[5.5]undecane-3-carbonyl)-4-fluorobenzyl)phthalazin-1(2H)-one (17d). Following the general procedure, 17d was purified by flash chromatography to afford the desired product as a white foam (0.055 g, 60%). $^1$H NMR (500 MHz, CDCl$_3$) δ 11.84 (s, 1H), 8.44-8.43 (m, 1H), 7.72-7.68 (m, 3H), 7.28-7.25 (m, 2H), 6.97 (t, J=8.5 Hz, 1H), 4.26 (s, 2H), 3.76 (s, 1H), 3.65 (s, 1H), 3.58-3.55 (m, 4H), 3.21 (s, 2H), 1.72-1.66 (m, 1H), 1.57-1.40 (m, 8H), 0.93 (s, 2H), 0.71-0.69 (m, 2H); $^{13}$C NMR (125 MHz, CDCl$_3$) δ 172.0, 164.9, 161.1, 156.2 (d, $J_{C-F}$=248.1 Hz), 145.7, 134.4 (d, $J_{C-C-C-C-F}$=3.7 Hz), 133.7, 131.6, 131.2 (d, $J_{C-F}$=8.1 Hz), 129.7, 128.9 (d, $J_{C-C-C-F}$=3.6 Hz), 128.3, 127.1, 125.2, 124.5 (d, $J_{C-F}$=18.3 Hz), 116.1 (d, $J_{C-F}$=22.0 Hz), 43.0, 41.4, 37.8, 37.7, 36.3, 36.0, 34.9, 34.5, 30.8, 11.1, 7.4; LC-MS (ESI) m/z: 503.13 [M+H], 525.30 [M+Na].

4-(4-fluoro-3-(6-(2-fluoroethoxy)-2-azaspiro[3.3]heptane-2-carbonyl)benzyl)phthalazin-1(2H)-one (37B). Compound 37B can be prepared following the general synthetic procedure to afford a white crystal-line solid (Yield 28%). $^1$H NMR (500 MHz, CDCl$_3$) (reported as mixture of rotamers) δ 11.23 (m, 1H), 8.47-8.45 (m, 1H), 7.77-7.73 (m, 2H), 7.72-7.69 (m, 1H), 7.49-7.46 (m, 1H), 7.31-7.28 (m, 1H), 7.00-6.96 (m, 1H), 4.54-4.53 (t, J=4.1 Hz, 1H), 4.45-4.43 (t, J=4.0 Hz, 1H), 4.27 (s, 2H), 4.13 (s, 1H), 3.98 (s, 1H), 3.96-3.83 (m, 1H), 3.59-3.56 (m, 1H), 3.53-3.50 (m, 1H), 2.56-2.52 (m, 1H), 2.50-2.46 (m, 1H), 2.21-2.17 (m, 1H), 2.14-2.10 (m, 1H); $^{13}$C NMR (125 MHz, CDCl$_3$) (reported as mixture of rotamers) δ 166.0 (2×C), 160.8, 157.0 (d, $J_{C-F}$=250.0 Hz), 156.9 (d, $J_{C-F}$=249.0 Hz), 145.7, 134.1, (d, $J_{C-C-C-C-F}$=3.2 Hz) 133.7, 132.3 (d, $J_{C-C-C-F}$=7.2 Hz) 130.8 (d, $J_{C-C-C-F}$=7.6 Hz), 131.6, 130.2 (d, $J_{C-C-C-F}$=3.4 Hz), 130.1 (d, $J_{C-C-C-F}$=3.5 Hz), 129.6, 128.4, 127.2, 125.2, 122.5 (d, $J_{C-C-F}$=17.6 Hz), 122.4 (d, $J_{C-C-F}$=17.0 Hz), 116.6 (d, $J_{C-C-F}$=22.5 Hz), 116.5 (d, $J_{C-C-F}$=22.7 Hz), 83.7 (d, $J_{C-F}$=169.4 Hz, CH$_2$F), 83.6 (d, $J_{C-F}$=169.4 Hz, CH$_2$F), 68.9, 68.8, 67.5 (d, $J_{C-F}$=19.7 Hz, 0-CH$_2$CH$_2$F), 67.4 (d, $J_{C-F}$=19.7 Hz, O—CH$_2$CH$_2$F), 63.5, 63.4, 62.3, 62.2, 60.8, 59.7, 41.0, 37.8 (2×C), 30.7, 30.6; LC-MS (ESI) m/z: 440.09 [M+H].

4-(4-fluoro-3-(3-(2-fluoroethoxy)azetidine-1-carbonyl) benzyl)phthalazin-1(2H)-one (26). Compound 26 can be prepared following the general synthetic procedure to afford a white crystalline solid (Yield 10%). $^1$H NMR (500 MHz, CDCl$_3$) δ 11.42 (s, 1H), 8.47-8.45 (m, 1H), 7.77-7.70 (m, 3H), 7.51-7.50 (dd, J$_1$=1.9 Hz, J$_2$=4.2 Hz, 1H), 7.32-7.29 (m, 1H), 6.95 (t, J=9.1 Hz, 1H), 4.58-4.56 (t, J=4.0 Hz, 1H), 4.49-4.47 (t, J=4.0 Hz, 1H), 4.38-4.33 (m, 2H), 4.27 (s, 2H), 4.19-4.16 (m, 1H), 4.07-4.06 (m, 1H), 4.00-3.98 (m, 2H), 3.71-3.56 (m, 2H); $^{13}$C NMR (125 MHz, CDCl$_3$) δ 166.2, 160.9, 156.9 (d, $J_{C-F}$=250.4 Hz), 145.7, 134.1 (d, $J_{C-C-C-C-F}$=3.4 Hz), 133.7, 132.4 (d, $J_{C-C-C-F}$=8.3 Hz), 131.6, 130.2 (d, $J_{C-C-C-F}$=3.4 Hz), 129.6, 128.3, 127.2, 125.0, 122.2 (d, $J_{C-C-F}$=16.9 Hz), 116.4 (d, $J_{C-C-F}$=22.7 Hz), 82.2 (d, $J_{C-F}$=169.9 Hz, CH$_2$F), 68.6, 68.5 (d, $J_{C-F}$=19.7 Hz, O—CH$_2$CH$_2$F), 58.5, 58.4, 55.9, 37.8; LC-MS (ESI) m/z: 400.17 [M+H].

(R)-4-(4-fluoro-3-(3-(2-fluoroethoxy)pyrrolidine-1-carbonyl)benzyl)phthalazin-1(2H)-one (28). Compound 28 can be prepared following the general synthetic procedure to afford a white crystalline solid (Yield 12%). $^1$H NMR (500 MHz, CDCl$_3$) (reported as mixture of rotamers) δ 11.81 (s, 1H), 8.45-8.43 (m, 1H), 7.74-7.70 (m, 3H), 7.38-7.35 (m, 1H), 7.27-7.25 (m, 1H), 6.99-6.96 (m, 1H), 4.57-4.39 (m, 2H), 4.26 (s, 2H), 4.19-4.06 (m, 1H), 3.76-3.70 (m, 2H), 3.69-3.65 (m, 1H), 3.63-3.41 (m, 2H), 3.32-3.27 (m, 1H); 2.08-2.02 (m, 1H), 2.01-1.92 (m, 1H); 13C NMR (125 MHz, CDCl$_3$) (reported as mixture of rotamers) δ 165.1 (2×C), 161.1, 156.3 (2×C) (d, $J_{(1)C-F}$=248.0 Hz; $J_{(2)C-F}$=247.6 Hz), 145.7, 134.2 (d, $J_{C-C-C-C-F}$=3.7 Hz), 134.1 (d, $J_{C-C-C-C-F}$=3.7 Hz), 133.6, 131.5, 131.4 (2×C) (d, $J_{(1)C-C-C-F}$=8.6 Hz; $J_{(2)C-C-C-F}$=8.1 Hz), 129.6, 129.1 (d, $J_{C-C-C-F}$=3.8 Hz), 128.9 (d, $J_{C-C-C-F}$=4.0 Hz), 128.3, 127.0, 125.4 (d, $J_{C-C-F}$=17.7 Hz), 125.4 (d, $J_{C-C-F}$=18.2 Hz), 125.2 (2×C), 116.3 (2×C) (d, $J_{(1)C-C-F}$=22.0 Hz; $J_{(1)C-C-F}$=22.0 Hz), 83.7 (d, $J_{C-F}$=169.5 Hz, CH$_2$F), 83.6 (d, $J_{C-F}$=169.7 Hz, CH$_2$F), 78.5, 77.6, 68.2 (d, $J_{C-F}$=19.6 Hz, O—CH$_2$CH$_2$F), 52.8 (2×C), 51.2, 45.7 (2×C), 44.0, 37.8, 31.6, 29.9; LC-MS (ESI) m/z: 414.19 [M+H].

(S)-4-(4-fluoro-3-(3-(2-fluoroethoxy)pyrrolidine-1-carbonyl)benzyl)phthalazin-1(2H)-one (29). Compound 29 can be prepared following the general synthetic procedure to afford a white crystalline solid (Yield 14%). $^1$H NMR (500 MHz, CDCl$_3$) (reported as mixture of rotamers) δ 11.65 (s, 1H), 8.45-8.44 (m, 1H), 7.72-7.71 (m, 3H), 7.39-7.36 (m, 1H), 7.28-7.26 (m, 1H), 7.00-6.96 (m, 1H), 4.57-4.40 (m, 2H), 4.27 (s, 2H), 4.19-4.08 (m, 1H), 3.77-3.71 (m, 2H), 3.69-3.64 (m, 1H), 3.59-3.42 (m, 2H), 3.32-3.28 (m, 1H), 2.09-1.93 (m, 2H); $^{13}$C NMR (125 MHz, CDCl$_3$) (reported as mixture of rotamers) δ 165.1 (2×C), 161.0, 156.3 (2×C) (d, $J_{(1)C-F}$=247.6 Hz; $J_{(2)C-F}$=247.6 Hz), 145.7, 134.2 (d, $J_{C-C-C-C-F}$=3.2 Hz), 134.1 (d, $J_{C-C-C-C-F}$=3.0 Hz), 133.7, 131.5, 131.4 (2×C) (d, $J_{(1)C-C-C-F}$=8.1 Hz; $J_{(2)C-C-C-F}$=7.4 Hz), 129.6, 129.1 (d, $J_{C-C-C-F}$=3.8 Hz), 128.9 (d, $J_{C-C-C-F}$=3.7 Hz), 128.3, 127.1, 125.5 (d, $J_{C-C-F}$=18.5 Hz), 125.4 (d, $J_{C-C-F}$=18.3 Hz), 125.2 (2×C), 116.4 (2×C) (d, $J_{(1)C-C-F}$=22.0 Hz; $J_{(1)C-C-F}$=22.0 Hz), 83.7 (d, $J_{C-F}$=169.3 Hz, CH$_2$F), 83.6 (d, $J_{C-F}$=169.8 Hz, CH$_2$F), 78.5, 77.6, 68.2 (d, $J_{C-F}$=19.9 Hz, O—CH$_2$CH$_2$F), 52.8 (2×C), 51.2, 45.8 (2×C), 44.0, 37.8, 31.6, 29.9; LC-MS (ESI) m/z: 414.19 [M+H].

4-(4-fluoro-3-(4-(2-fluoroethoxy)piperidine-1-carbonyl) benzyl)phthalazin-1(2H)-one (31). Compound 31 can be prepared following the general synthetic procedure to afford a white crystalline solid (Yield 37%). $^1$H NMR (500 MHz, CDCl$_3$) δ 11.84 (s, 1H), 8.45-8.43 (m, 1H), 7.73-7.67 (m, 3H), 7.30-7.28 (m, 1H), 7.27-7.24 (m, 1H), 6.98-6.95 (t, J=8.8 Hz, 1H), 4.56-4.54 (t, J=4.1 Hz, 1H), 4.46-4.44 (t, J=4.1 Hz, 1H), 4.26 (s, 2H), 3.96 (bs, 1H), 3.73-3.68 (m, 1H), 3.67-3.63 (m, 1H), 3.62-3.60 (m, 1H), 3.55 (bs, 1H), 3.43 (bs, 1H), 3.08 (bs, 1H), 1.91-1.87 (m, 1H), 1.72-1.66 (m, 2H), 1.55 (bs, 1H); $^{13}$C NMR (125 MHz, CDCl$_3$) δ 164.8, 161.0, 156.1 (d, $J_{C-F}$=247.2 Hz), 145.6, 134.2 (d, $J_{C-C-C-C-F}$=3.1 Hz), 133.6, 131.5, 131.1 (d, $J_{C-C-C-F}$=7.9 Hz), 129.5, 128.9 (d, $J_{C-C-C-F}$=3.7 Hz), 128.2, 127.0, 125.1, 124.5 (d, $J_{C-C-F}$=18.7 Hz), 116.1 (d, $J_{C-C-F}$=21.6 Hz), 83.8 (d, $J_{C-F}$=169.4 Hz, CH$_2$F), 74.2, 68.2 (d, $J_{C-F}$=19.3 Hz, O—CH$_2$CH$_2$F), 44.1, 38.8, 37.7, 31.3, 30.3; LC-MS (ESI) m/z: 428.08 [M+H].

4-(4-fluoro-3-(4-(2-fluoroethoxy)azepane-1-carbonyl) benzyl)phthalazin-1(2H)-one (33). Compound 33 can be prepared following the general synthetic procedure to afford a white crystalline solid (Yield 41%). $^1$H NMR (500 MHz, CDCl$_3$) (reported as mixture of isomers and rotamers) δ 11.76-11.74 (m, 1H), 8.45-8.43 (m, 1H), 7.73-7.69 (m, 3H), 7.28-7.23 (m, 2H), 7.28-7.24 (m, 2H), 6.99-6.95 (m, 1H), 4.56-4.53 (m, 1H), 4.46-4.42 (m, 1H), 4.26 (s, 2H), 3.74 (bs, 1H), 3.69-3.65 (m, 1H), 3.62-3.56 (m, 2H), 3.55-3.51 (m, 1H), 3.39-3.20 (m, 2H), 2.04-1.91 (m, 2H), 1.87-1.77 (m, 2H), 1.74-1.68 (m, 2H), 1.55 (bs, 1H); $^{13}$C NMR (125 MHz, CDCl$_3$) (reported as mixture of isomers and rotamers) δ 166.5, 166.3, 161.0 (2×C), 155.9 (d, $J_{C-F}$=247.4 Hz), 145.7, 134.2 (d, $J_{C-C-C-C-F}$=3.5 Hz), 134.1 (d, $J_{C-C-C-C-F}$=3.5 Hz), 133.6 (2×C), 131.5, 130.9 (d, $J_{C-C-C-F}$=7.5 Hz), 130.8 (d, $J_{C-C-C-F}$=7.6 Hz), 129.6, 128.5 (d, $J_{C-C-C-F}$=4.0 Hz), 128.2, 127.1, 125.5 (d, $J_{C-C-F}$=19.0 Hz), 125.4 (d, $J_{C-C-F}$=19.0 Hz), 116.3 (d, $J_{C-C-F}$=21.7 Hz), 116.2 (d, $J_{C-C-F}$=21.7 Hz), 84.0 (d, $J_{C-F}$=169.2 Hz, CH$_2$F), 83.9 (d, $J_{C-F}$=168.9 Hz, CH$_2$F), 77.5, 77.2, 67.7 (d, $J_{C-F}$=19.7 Hz, O—CH$_2$CH$_2$F), 67.6 (d, $J_{C-F}$=20.0 Hz, O—CH$_2$CH$_2$F), 48.7, 45.9, 43.8, 40.6, 37.8, 34.4, 32.9, 31.8, 30.1, 21.8, 21.3; LC-MS (ESI) m/z: 442.25 [M+H].

4-(4-fluoro-3-(4-(4-fluorophenyl)piperidine-1-carbonyl) benzyl)phthalazin-1(2H)-one (36). Compound 36 can be prepared following the general synthetic procedure to afford a hard white solid (Yield 28%). $^1$H NMR (500 MHz, ((CD$_3$)$_2$SO) δ 12.60 (s, 1H), 8.25 (d, J=7.6 Hz, 1H), 7.85-7.82 (m, 1H), 7.79-7.76 (m, 1H), 7.42-7.40 (m, 2H), 7.25-7.19 (m, 3H), 7.10 (t, J=8.9 Hz, 1H), 4.64-4.61 (m, 1H), 4.33 (s, 2H), 3.40-3.38 (m, 1H), 3.10 (t, J=12.4 Hz, 1H), 2.83-2.75 (m, 2H), 1.83-1.81 (m, 1H), 1.63-1.49 (m, 2H), 1.40 (bs, 1H). $^{13}$C NMR (125 MHz, ((CD$_3$)$_2$SO)) δ 163.6, 159.7 (d, $J_{C-F}$=243.0 Hz), 159.3, 155.3 ($J_{C-F}$=243.0 Hz), 144.8, 141.4 (d, $J_{C-C-C-C-F}$=2.6 Hz), 134.7 (d, $J_{C-C-C-C-F}$=2.9 Hz), 133.3, 131.4, 131.3 (d, $J_{C-C-C-F}$=7.8 Hz), 129.0, 128.5, 128.4 (d, $J_{C-C-C-F}$=7.8 Hz), 127.9, 126.0, 125.4, 124.3 (d, $J_{C-C-F}$=18.2 Hz), 115.9 (d, $J_{C-C-F}$=22.0 Hz), 114.9 (d, $J_{C-C-F}$=20.7 Hz), 59.7, 54.86, 46.9, 41.6, 40.7, 36.4, 32.6; LC-MS (ESI) m/z: 460.12 [M+H].

4-(4-fluoro-3-(6-(4-fluorophenyl)-2,6-diazaspiro[3.3] heptane-2-carbonyl)benzyl)phthalazin-1(2H)-one (40). Compound 40 can be prepared following the general synthetic procedure to afford a hard white solid (Yield 26%). $^1$H NMR (500 MHz, CDCl$_3$) δ 11.83 (s, 1H), 8.25 (d, J=7.7 Hz, 1H), 7.75-7.70 (m, 3H), 7.52-7.50 (dd, J$_1$=2.0 Hz, J$_2$=6.2 Hz, 1H), 7.34-7.31 (m, 1H), 7.00 (t, J=9.2 Hz, 1H), 6.87 (t, J=8.7 Hz, 1H), 6.34-6.32 (m, 2H), 4.31 (s, 2H), 4.28 (s, 2H), 4.20 (s, 2H), 3.94 (d, J=7.6 Hz, 2H), 3.89 (d, J=7.6 Hz, 2H). $^{13}$C NMR (125 MHz, CDCl$_3$) δ 166.6, 161.1, 156.9 (d, $J_{C-F}$=250.2 Hz), 155.4 ($J_{C-F}$=236.0 Hz), 147.6, 145.6, 134.2 (d, $J_{C-C-C-C-F}$=3.0 Hz), 133.7, 132.6 (d, $J_{C-C-C-F}$=8.3 Hz), 131.5, 130.2 (d, $J_{C-C-C-C-F}$=3.3 Hz), 129.6, 128.2, 127.1, 125.1, 122.0 (d, $J_{C-C-F}$=16.8 Hz), 116.3 (d, $J_{C-C-F}$=22.5 Hz), 115.6 (d, $J_{C-C-F}$=22.3 Hz), 112.8 (d, $J_{C-C-C-F}$=7.5 Hz), 62.5, 61.2, 61.1, 58.6, 37.7, 33.7; LC-MS (ESI) m/z: 473.21 [M+H].

4-(4-fluoro-3-(6-(4-fluorophenyl)-2-azaspiro[3.3]heptane-2-carbonyl)benzyl)phthalazin-1(2H)-one (39). A solution of compound a (6.0 mmol) in THF (20 mL) at 0° C. was treated with triphenylphosphine (10 mmol), followed by CBr$_4$ (10 mmol). After 1 h, the reaction mixture was warmed to room temp, and stirred for an additional 2 h. Next, the solvent was removed under reduced pressure to afford a crude oily residue. The subsequent residue was loaded onto a Biotage SNAP flash purification cartridge, eluting with a 1:20 EtOAc/hexanes gradient, to afford compound b as a white solid. (Yield 26%)$^1$H NMR (500 MHz, CDCl$_3$) δ 4.27-4.24 (m, 1H), 3.89 (quint, J=7.3 Hz, 1H), 3.89 (s, 2H), 3.86 (s, 2H), 2.83-2.79 (m, 2H), 2.57-2.52 (m, 2H), 1.37 (s, 9H). $^{13}$C NMR (125 MHz, CDCl$_3$) δ 156.0, 79.4, 61.0, 60.7, 45.6, 36.4, 35.6, 28.3; LC-MS (ESI) m/z: 176.18 [M-Boc]. A 40 mL vial was charged with NiI$_2$ (0.20 mmol), trans-2-aminocyclohexanol hydrochloride (0.20 mmol), NaHMDS (4.0 mmol), and 2-methyl-2-butanol (1.0 mL). The reaction was purged with N$_2$ for 5 min, followed by the addition of compound b (2.0 mmol) in 2.5 mL of 2-methyl-2-butanol. The reaction mixture was heated to 80° C. and stirred vigorously for 12 h. After which, the crude reaction mixture was filtered and the solvent was removed under reduced pressure. The subsequent residue was loaded onto a Biotage SNAP flash purification cartridge, eluting with a 1:5 EtOAc/hexanes gradient, to afford the Boc-protected precursor (compound d) as a white solid. (Yield 74%). The intermediate was then dissolved in CH$_2$C$_2$ (2 mL), followed by dropwise addition of CF$_3$COOH (2 mL), and stirred at room temperature for 3 h. Volatiles were then removed under reduced pressure and the crude product was neutralized with a saturated NaHCO$_3$(aq) solution (10 mL). The reaction mixture was extracted with CH$_2$C$_2$ (3×20 mL), and the organic layers were combined, dried, and concentrated to afford the free-amine intermediate, i.e., 6-(4-fluorophenyl)-2-azaspiro[3.3]heptane, as light-tan solid. Finally, intermediate 6-(4-fluorophenyl)-2-azaspiro[3.3]heptane (1.0 mmol), 16 (1.0 mmol), HOBt hydrate (1.0 mmol), EDC hydrochloride (1.0 mmol), and Et$_3$N (2.0 mmol) were stirred in 5 mL of THF at 60° C. for 12 h. A saturated NaHCO$_3$(aq) solution (15 mL) was then added to the crude reaction mixture and stirred at room temp for 1 h. The reaction mixture was extracted with CH$_2$Cl$_2$ (3×20 mL) to afford the crude product. The residue was loaded onto a Biotage SNAP flash purification cartridge, eluting with 10% 7N NH$_3$ in MeOH solution/CH$_2$Cl$_2$ to give the target compound 39 as a soft white solid. (Yield 18%) H NMR (500 MHz, CDCl$_3$) (reported as mixture of rotamers) δ 11.38 (m, 1H), 8.48-8.46 (m, 1H), 7.77-7.71 (m, 3H), 7.52-7.49 (m, 1H), 7.34-7.29 (m, 1H), 7.10-7.06 (m, 2H), 7.01-6.93 (m, 3H), 4.29-4.28 (m, 3H), 4.16 (s, 1H), 4.08 (s, 1H), 3.94 (s, 1H), 3.42-3.25 (m, 1H), 2.64-2.60 (m, 1H), 2.58-2.54 (m, 1H), 2.31-2.27 (m, 1H), 2.24-2.19 (m, 1H). $^{13}$C NMR (125 MHz, CDCl$_3$) (reported as mixture of rotamers) δ 166.1, 166.0, 160.9, 160.4 (2×C) (d, $J_{1C-F}$=244.7 Hz, $J_{2C-F}$=244.7 Hz), 157.0 ($J_{C-F}$=250.4 Hz), 145.7, 140.0 (d, $J_{C-C-C-C-F}$=2.8 Hz), 139.9 (d, $J_{C-C-C-C-F}$=2.7 Hz), 134.1, 134.0 (d, $J_{C-C-C-F}$=8.1 Hz), 133.7, 132.2 (d, $J_{C-C-C-F}$=8.2 Hz), 131.6, 130.2, 129.6, 128.4, 127.7 (d, $J_{C-C-C-C-F}$=3.2 Hz), 127.6 (d, $J_{C-C-C-C-F}$=2.8 Hz), 127.2, 125.2, 122.4 (d, $J_{C-C-F}$=17.2 Hz), 122.3 (d, $J_{C-C-F}$=17.2 Hz), 116.3 (d, $J_{C-C-F}$=22.7 Hz), 115.1 (d, $J_{C-C-F}$=21.2 Hz), 64.0, 63.9, 61.9, 61.8, 61.4, 59.3, 40.4, 37.8, 34.4, 34.2, 33.6, 33.3; LC-MS (ESI) m/z: 472.14 [M+H].

4-(4-fluoro-3-(4-(2-hydroxyethoxy)piperidine-1-carbonyl)benzyl)phthalazin-1(2H)-one (b). Compound 9 (1.0 mmol), 2-(piperidin-4-yloxy)ethan-1-ol (1.0 mmol), HOBt hydrate (1.0 mmol), EDC hydrochloride (1.0 mmol), and Et$_3$N (2.0 mmol) were stirred in 5 mL of THF at 60° C. for 12 h. A saturated NaHCO$_3$(aq) solution (15 mL) was then added to the crude reaction mixture and stirred at room temp for 1 h. The reaction mixture was extracted with CH$_2$Cl$_2$ (3×20 mL) to afford the crude product. The residue was loaded onto a Biotage SNAP flash purification cartridge, eluting with 10% 7N NH$_3$ in MeOH solution/CH$_2$Cl$_2$ to give the target compound b as a white crystalline solid. (Yield 38%) H NMR (500 MHz, CDCl$_3$) δ 11.78 (s, 1H), 8.42-8.40 (m, 1H), 7.69-7.67 (m, 3H), 7.28-7.26 (m, 1H), 7.25-7.26

(m, 1H), 6.97-6.93 (m, 1H), 4.24 (m, 2H), 4.01 (bs, 1H), 3.69-3.68 (m, 2H), 3.57-3.50 (m, 3H), 3.43 (bs, 2H), 3.05 (bs, 1H), 2.81 (bs, 1H), 1.91-1.88 (m, 1H), 1.73 (bs, 1H), 1.68-1.62 (m, 1H), 1.52 (bs, 1H); $^{13}$C NMR (125 MHz, CDCl$_3$) δ 164.8, 160.9, 156.0 (d, $J_{C-F}$=246.9 Hz), 145.7, 134.2 (d, $J_{C-C-C-C-F}$=3.1 Hz), 133.6, 131.5, 131.1 (d, $J_{C-C-C-F}$=7.8 Hz), 129.5, 128.9 (d, $J_{C-C-C-F}$=3.5 Hz), 128.2, 127.0, 125.1, 124.5 (d, $J_{C-C-F}$=18.6 Hz), 116.1 (d, $J_{C-C-F}$=22.0 Hz), 74.2, 69.4, 61.8, 44.3, 39.0, 37.7, 31.3, 30.5; LC-MS (ESI) m/z: 426.06 [M+H].

2-((1-(2-fluoro-5-((4-oxo-3,4-dihydrophthalazin-1-yl)methyl)benzoyl)piperidin-4-yl)oxy)ethyl 4-methylbenzenesulfonate (BB). Reagent p-toluenesulfonyl chloride (1.3 mmol) was slowly added to a stirring solution of compound AA (1.0 mmol) and TEA (2.1 mmol) in 20 mL of DCM at 0° C. The reaction mixture was allowed to warm to room temp, and stirred for 12 h. Then, the reaction mixture was filtered and solvent was removed under reduced pressure to afford a crude oily re-side. The subsequent residue was loaded onto a Biotage SNAP flash purification cartridge, eluting with a 1:20 MeOH/EtOAc gradient, to afford compound BB as a white crystalline solid. (Yield 75%) $^1$H NMR (500 MHz, CDCl$_3$) δ 11.61 (s, 1H), 8.45-8.43 (m, 1H), 7.76-7.74 (m, 3H), 7.73-7.69 (m, 2H), 7.31-7.29 (m, 3H), 7.28-7.25 (m, 1H), 6.99-6.96 (t, J=8.7 Hz, 1H), 4.26 (s, 2H), 4.13-4.11 (t, J=4.7 Hz, 2H), 3.79 (bs, 1H), 3.66-3.58 (m, 3H), 3.52 (bs, 1H), 3.35 (bs, 1H), 3.05 (bs, 1H), 2.40 (s, 3H), 1.80-1.76 (m, 1H), 1.65 (bs, 1H), 1.58-1.56 (m, 1H), 1.47 (bs, 1H); $^{13}$C NMR (125 MHz, CDCl$_3$) δ 164.8, 160.9, 156.0 (d, $J_{C-F}$=247.6 Hz), 145.7, 144.9, 134.2 (d, $J_{C-C-C-C-F}$=3.3 Hz), 133.6, 133.0, 131.5, 131.2 (d, $J_{C-C-C-F}$=7.9 Hz), 129.8, 129.6, 128.9 (d, $J_{C-C-C-F}$=3.4 Hz), 128.3, 127.9, 127.1, 124.5, 125.1, 124.5 (d, $J_{C-C-F}$=18.4 Hz), 116.1 (d, $J_{C-C-F}$=22.0 Hz), 74.1, 69.5, 65.7, 43.9, 38.6, 37.7, 31.3, 30.5, 21.6; LC-MS (ESI) m/z: 426.06 [M+H]; LC-MS (ESI) m/z: 580.20 [M+H]

2-((1-(2-fluoro-5-((4-oxo-3,4-dihydrophthalazin-1-yl)methyl)benzoyl)piperidin-4-yl)oxy)ethyl methanesulfonate (CC). Reagent methane sulfonyl chloride (1.3 mmol) was slowly added to a stirring solution of compound AA (1.0 mmol) and TEA (2.1 mmol) in 20 mL of DCM at 0° C. The reaction mixture was allowed to warm to room temp, and stirred for 12 h. Then, the reaction mixture was filtered and solvent was removed under reduced pressure to afford a crude oily reside. The subsequent residue was loaded onto a Biotage SNAP flash purification cartridge, eluting with a 1:20 MeOH/EtOAc gradient, to afford compound BB as a white crystalline solid. (Yield 80%) $^1$H NMR (500 MHz, CDCl$_3$) δ 11.33 (s, 1H), 8.46-8.44 (m, 1H), 7.75-7.71 (m, 3H), 7.30-7.26 (m, 2H), 7.01-6.97 (t, J=8.8 Hz, 1H), 4.34-4.33 (t, J=4.5 Hz, 2H), 4.27 (s, 2H), 3.98 (bs, 1H), 3.76-3.68 (m, 2H), 3.61 (bs, 1H), 3.53 (bs, 1H), 3.45-3.43 (m, 1H), 3.11 (bs, 1H), 3.03 (s, 3H), 1.92-1.88 (m, 1H), 1.75 (bs, 1H), 1.71-1.66 (m, 1H), 1.54 (bs, 1H); $^{13}$C NMR (125 MHz, CDCl$_3$) δ 164.9, 160.8, 156.1 (d, $J_{C-F}$=246.7 Hz), 145.7, 134.2 (d, $J_{C-C-C-C-F}$=3.2 Hz), 133.7, 133.0, 131.6, 131.2 (d, $J_{C-C-C-F}$=7.7 Hz), 129.6, 129.0 (d, $J_{C-C-C-F}$=3.7 Hz), 128.3, 127.1, 125.1, 124.6 (d, $J_{C-C-F}$=18.5 Hz), 116.2 (d, $J_{C-C-F}$=21.8 Hz), 74.5, 69.3, 66.0, 44.1, 38.9, 37.8, 37.7, 31.3, 30.4; LC-MS (ESI) m/z: 504.86 [M+H].

Example 5: PARP Inhibition

Compounds 10-17 were evaluated for PARP-1 inhibition using a radioligand binding assay protocol with BRCA1 methylated ovarian cancer cells (OVCAR8) as described above. See, Table 3. Generally, good to moderate PARP-1 inhibitor potency were observed with methylene spiro-motifs 1a-8a in the phthalazone architecture with IC$_{50}$ values ranging from 32.4-57.1 nM. Compared to 1a, oxaazaspiro analogue 1b performed slightly better with scaffold 10b displaying a PARP-1 binding value of 24.9 nM.

TABLE 3

| Compound | R | EC$_{50}$ (nM) |
| --- | --- | --- |
| 10a | CH$_2$ | 33.9 ± 1.5 |
| 10b | O | 24.9 ± 1.2 |
| 10c | NBoc | 551.6 ± 1.0 |
| 10d | NH | 2395 ± NA |
| 10e | N-C(O)-cyclopropyl | 12.6 ± 1.1 |
| 12a | CH$_2$ | 65.4 ± 1.5 |
| 12b | NBoc | 3118 ± 1.0 |
| 12c | NH | 1419 ± 2.3 |
| 12d | N-C(O)-cyclopropyl | 100.1 ± 1.2 |

TABLE 3-continued

| Compound | R | EC₅₀ (nM) |
|---|---|---|
| 13a | CH₂ | 284 ±1.2 |
| 13b | NBoc | 2969 ± 1.1 |
| 13c | NH | 109.5 ± 1.0 |
| 13d | N-C(O)-cyclopropyl | 430.9 ± 1.1 |
| 14a | CH₂ | 32.4 ± 1.1 |
| 14b | NBoc | 1193 ± 1.0 |
| 14c | NH | 1237 ± 2.6 |
| 14d | N-C(O)-cyclopropyl | 2535 ± 1.0 |
| 15a | CH₂ | 51.4 ± 1.1 |
| 15b | NBoc | 4397 ± 1.1 |
| 15c | NH | 1118 ± 1.7 |
| 15d | N-C(O)-cyclopropyl | 2586 ± 1.0 |
| 16a | CH₂ | 141.4 ± 1.3 |
| 16b | NBoc | 1105 ± 1.0 |
| 16c | NH | 3881 ± 9.9 |
| 16d | N-C(O)-cyclopropyl | 224.9 ± 1.0 |
| 17a | CH₂ | 57.1 ± 1.2 |
| 17b | NBoc | 452.8 ± 1.0 |
| 17c | NH | 233.7 ± 1.0 |
| 17d | N-C(O)-cyclopropyl | 44.3 ± 1.2 |

TABLE 3-continued
| Compound | R | EC$_{50}$ (nM) |
|---|---|---|
| 18 | 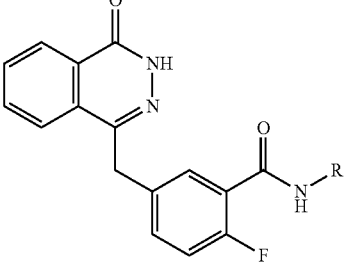 | 74.13± |
| 19 (cis) 20 (trans) | 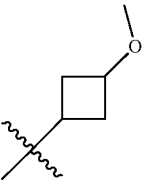 [SMILES: *C1CC(OC)C1] | 20.83 ± 1.1 107.2 ± 1.1 |
| 21 | 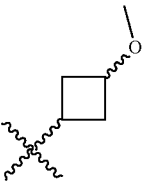 | 49.57 ± 1.1 |
| 22 | 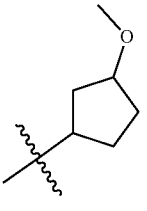 [SMILES: *C1CCC(OC)C1] | 226.3 ± 1.1 |
| 23 | 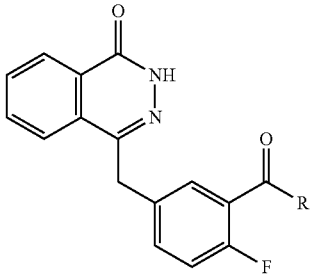 | 8.273 ± 1.1 |
| 24 | 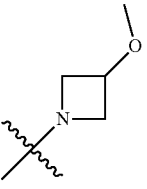 | 4.211 ± 1.1 |
| 25 | 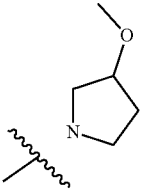 | 4.738 ± 1.1 |
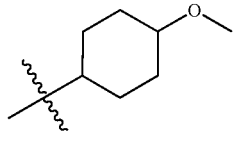 [SMILES: *C1CCC(OC)CC1]

TABLE 3-continued

| Compound | R | EC$_{50}$ (nM) |
|---|---|---|
| 26 | | 7.537 ± 1.1 |
| 27 | | |
| 28 (R) | | 10.1 ± 1.1 |
| 29 (S) | | 6.884 ± 1.1 |
| 30 | | |
| 31 | | 3.951 ± 1.2 |
| 32 | | |
| 33 | | 5.621 ± 1.1 |
| 34 | | |

TABLE 3-continued
| Compound | R | EC$_{50}$ (nM) |
|---|---|---|
| 35 | 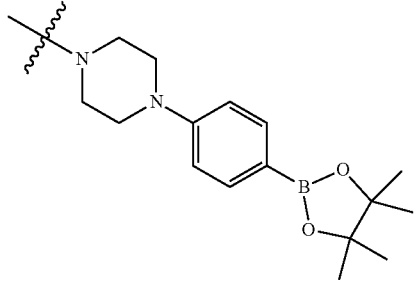 [SMILES: *N1CCN(c2ccc(B3OC(C)(C)C(C)(C)O3)cc2)CC1] | |
| 36 | 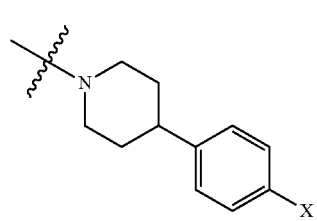<br>X = $^{18}$F, $^{123}$I, $^{124}$I, $^{125}$I, $^{131}$I, $^{76}$Br, $^{77}$Br, $^{211}$At | 1.3 (X = F) |
| 37A | CHOCH$_2$CH$_2$CH$_2$F | 10.74 ± 1.1 |
| 37B | CHOCH$_2$CH$_2$F | |
| 38 | CHOCH$_2$CH$_2$CH$_2^{18}$F | |
| 39 | 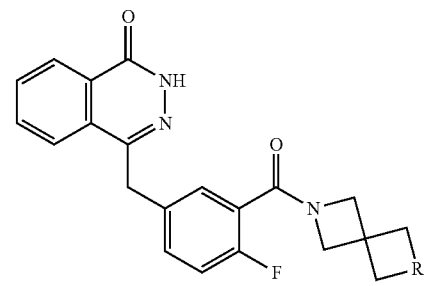 | 2.8 |
| 40 | 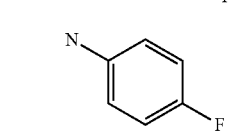 | 0.3755 ± 1.2 |
| 41 | 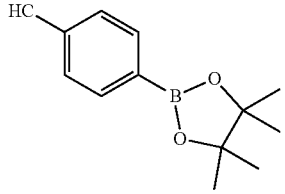 | |
| 42 | 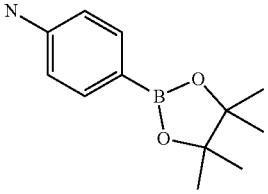 | |
| 43 | 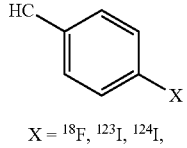<br>X = $^{18}$F, $^{123}$I, $^{124}$I, $^{125}$I, $^{131}$I, $^{76}$Br, $^{77}$Br, $^{211}$At | |

TABLE 3-continued
| Compound | R | EC$_{50}$ (nM) |
|---|---|---|
| 44 | 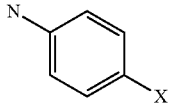 X = $^{18}$F, $^{123}$I, $^{124}$I, $^{125}$I, $^{131}$I, $^{76}$Br, $^{77}$Br, $^{211}$At | |
| 45 | 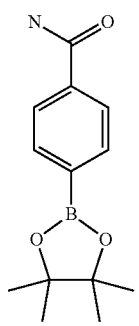 | |
| 46 | 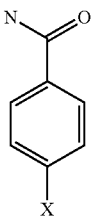 | (X = F) 21.8 (X = I) 11.6 |
| 47 | CHOCH$_2$CH$_2$CH$_2$F | |
| 48 | CHOCH$_2$CH$_2$CH$_2$$^{18}$F | |
| 49 | 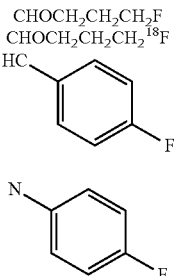 | |
| 50 | 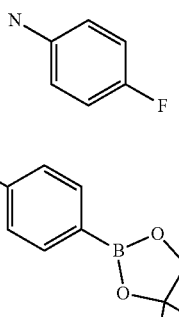 | |
| 51 | 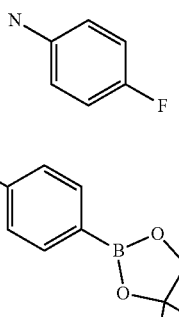 | |
| 52 | 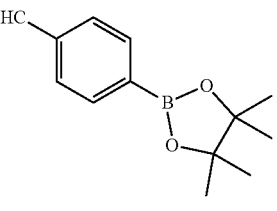 | |
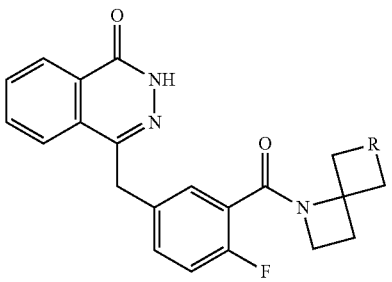

TABLE 3-continued

| Compound | R | EC$_{50}$ (nM) |
|---|---|---|
| 53 | 4-X-benzyl; X = $^{18}$F, $^{123}$I, $^{124}$I, $^{125}$I, $^{131}$I, $^{76}$Br, $^{77}$Br, $^{211}$At | |
| 54 | 4-X-anilino (N-linked); X = $^{18}$F, $^{123}$I, $^{124}$I, $^{125}$I, $^{131}$I, $^{76}$Br, $^{77}$Br, $^{211}$At | |
| 55 | CHOCH$_2$CH$_2$CH$_2$F | |
| 56 | CHOCH$_2$CH$_2$CH$_2$$^{18}$F | |
| 57 | 4-F-benzyl | |
| 58 | 4-F-anilino (N-linked) | |
| 59 | 4-(4,4,5,5-tetramethyl-1,3,2-dioxaborolan-2-yl)benzyl | |
| 60 | 4-(4,4,5,5-tetramethyl-1,3,2-dioxaborolan-2-yl)anilino (N-linked) | |
| 61 | 4-X-benzyl; X = $^{18}$F, $^{123}$I, $^{124}$I, $^{125}$I, $^{131}$I, $^{76}$Br, $^{77}$Br, $^{211}$At | |
| 62 | 4-X-anilino (N-linked); X = $^{18}$F, $^{123}$I, $^{124}$I, $^{125}$I, $^{131}$I, $^{76}$Br, $^{77}$Br, $^{211}$At | |

Core structure: 4-((4-fluoro-3-(2-azaspiro[3.5]nonane-2-carbonyl)phenyl)methyl)phthalazin-1(2H)-one with R substituent on the spiro ring.

TABLE 3-continued
| | Compound | R | EC$_{50}$ (nM) |
|---|---|---|---|
| 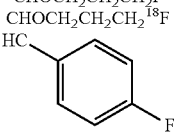 | 63<br>64<br>65 | CHOCH$_2$CH$_2$CH$_2$F<br>CHOCH$_2$CH$_2$CH$_2$$^{18}$F<br>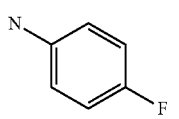 | |
| | 66 | 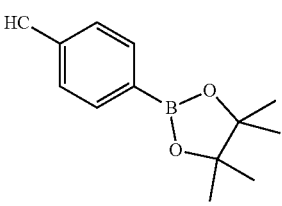 | |
| | 67 | 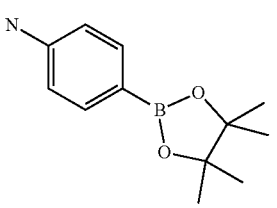 | |
| | 68 | 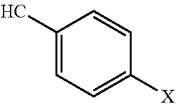 | |
| | 69 | 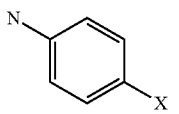<br>X = $^{18}$F, $^{123}$I, $^{124}$I,<br>$^{125}$I, $^{131}$I, $^{76}$Br,<br>$^{77}$Br, $^{211}$At | |
| | 70 | 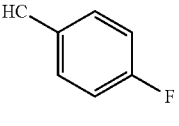<br>X = $^{18}$F, $^{123}$I, $^{124}$I,<br>$^{125}$I, $^{131}$I, $^{76}$Br,<br>$^{77}$Br, $^{211}$At | |
| 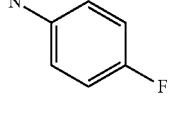 | 71<br>72<br>73 | CHOCH$_2$CH$_2$CH$_2$F<br>CHOCH$_2$CH$_2$CH$_2$$^{18}$F<br>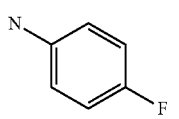 | |
| | 74 | 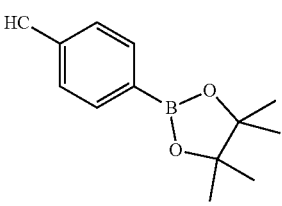 | |

TABLE 3-continued
| Compound | R | EC$_{50}$ (nM) |
|---|---|---|
| 75 | 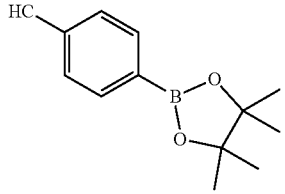 | |
| 76 | 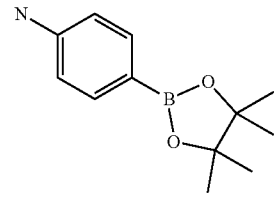 | |
| 77 | 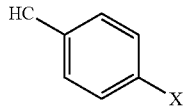<br>X = $^{18}$F, $^{123}$I, $^{124}$I,<br>$^{125}$I, $^{131}$I, $^{76}$Br,<br>$^{77}$Br, $^{211}$At | |
| 78 | 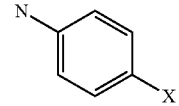<br>X = $^{18}$F, $^{123}$I, $^{124}$I,<br>$^{125}$I, $^{131}$I, $^{76}$Br,<br>$^{77}$Br, $^{211}$At | |
| 79 | CHOCH$_2$CH$_2$CH$_2$F | |
| 80 | CHOCH$_2$CH$_2$CH$_2$$^{18}$F | |
| 81 | 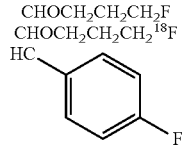 | |
| 82 | 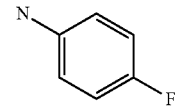 | |
| 83 | 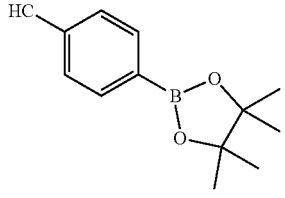 | |
| 84 | 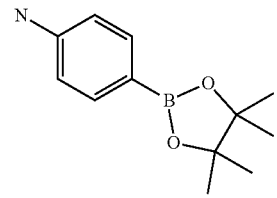 | |

TABLE 3-continued
| Compound | R | EC$_{50}$ (nM) |
|---|---|---|
| 85 | 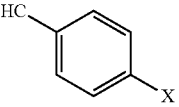 X = $^{18}$F, $^{123}$I, $^{124}$I, $^{125}$I, $^{131}$I, $^{76}$Br, $^{77}$Br, $^{211}$At | |
| 86 | 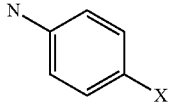 X = $^{18}$F, $^{123}$I, $^{124}$I, $^{125}$I, $^{131}$I, $^{76}$Br, $^{77}$Br, $^{211}$At | |
| 87 | CHOCH$_2$CH$_2$CH$_2$F | |
| 88 | CHOCH$_2$CH$_2$CH$_2$$^{18}$F | |
| 89 | 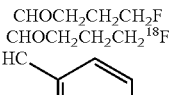 | |
| 90 | 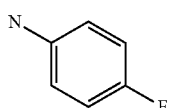 | |
| 91 | 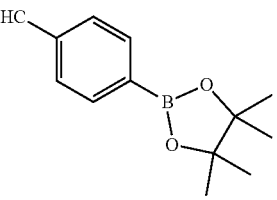 | |
| 92 | 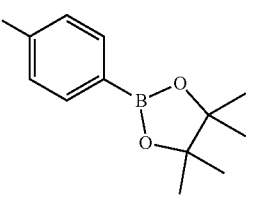 | |
| 93 | 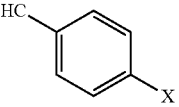 X = $^{18}$F, $^{123}$I, $^{124}$I, $^{125}$I, $^{131}$I, $^{76}$Br, $^{77}$Br, $^{211}$At | |
| 94 | 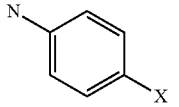 | |

TABLE 3-continued

| Compound | R | EC$_{50}$ (nM) |
|---|---|---|
| 95 | CHOCH$_2$CH$_2$CH$_2$F | |
| 96 | CHOCH$_2$CH$_2$CH$_2{}^{18}$F | |
| 97 | 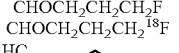 | |
| 98 | 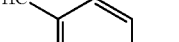 | |
| 99 | 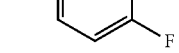 | |
| 100 | 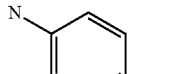 | |
| 102 | 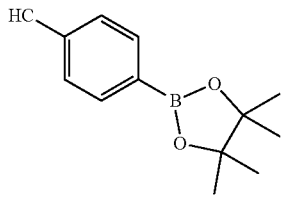<br>X = $^{18}$F, $^{123}$I, $^{124}$I,<br>$^{125}$I, $^{131}$I, $^{76}$Br,<br>$^{77}$Br, $^{211}$At | |
| 103 | 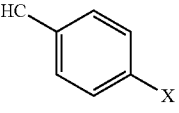<br>X = $^{18}$F, $^{123}$I, $^{124}$I,<br>$^{125}$I, $^{131}$I, $^{76}$Br,<br>$^{77}$Br, $^{211}$At | |

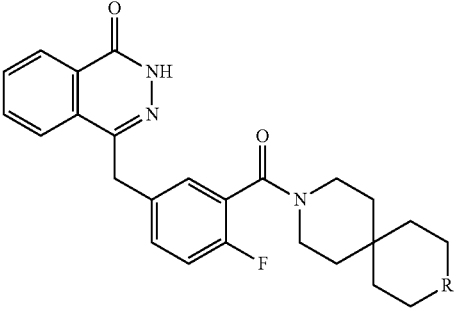

Cellular potency was drastically reduced when examining ligand scaffolds containing diazaspiro cores with the boc-functional group. Compared to the methylene congener 10a, compound 10c demonstrated a ~16-fold lower PAR-P-1 affinity (IC$_{50}$=551.6 nM). Amino core 6a resulted in the largest reduction in enzyme affinity, in contrast to 15a, resulting in a ~85-fold decrease in PARP-1 inhibition for 15b, (IC$_{50}$=4,397 nM). Among the boc-containing analogues examined during this investigation, compound 17b (IC$_{50}$=452.8 nM) was identified as the most potent inhibitor.

PARP-1 inhibition was further reduced when examining free-amine analogues 10d, 11c-17c. PARP-1 affinity values improved over ~29 fold upon removing the boc-group from compound 13b, to afford free amine compound 13c (IC$_{50}$=109.5 nM). A slight increase in enzyme affinity was also observed with free-amine derivatives 11c, 12c, 15c, and 17c, in contrast to their respective boc-protected analogues.

Apart from compounds 13d-15d, coupling the cyclopropanecarbonyl resulted in lower IC$_{50}$ values than those obtained with the free-amine analogues. The most potent PARPi identified in this study was 10e (IC$_{50}$=12.6 nM), suggesting spirocore 1 can act as a viable structural surrogate for the piperazine ring. However, compounds 13d-15d displayed lower PARP-1 inhibition compared to the corresponding free-amine analogues. Compound 17d also displayed improved PARP-1 potency (IC$_{50}$=44.3 nM) when compared to the boc-protected (17b) and free-amine (17c) derivatives.

Example 6: Cytotoxicity Studies

Figure 1B:
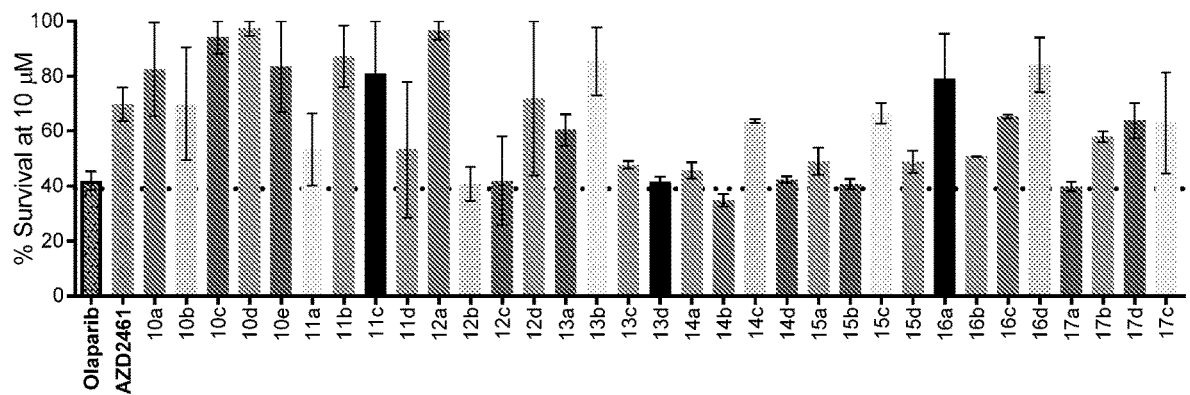
Figure 1C:
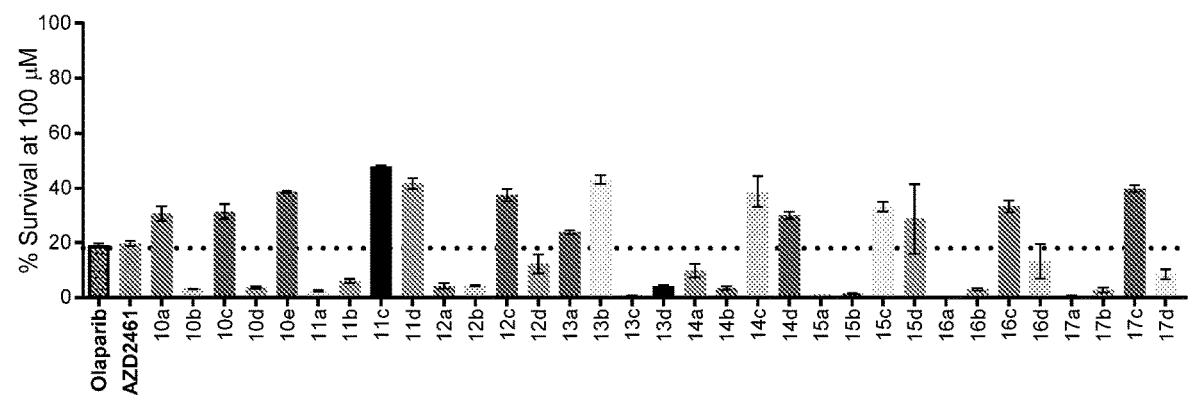

Cytotoxicity was then examined in OVCAR8 cells at 1, 10 and 100 μm concentrations as described above. See, FIGS. 1A-1C. In contrast, several compounds with μM PARP-1 $IC_{50}$ values displayed the most promising antiproliferative activity, comparable or even exceeding cytotoxicity values obtained with olaparib and AZD2461. Interestingly, this unusual correlation was observed mostly with analogues containing boc-protected diazaspiro cores, with poor PARP-1 binding profiles, such as compounds 12b ($IC_{50}$=3,118 nM), 14b ($IC_{50}$=1,193 nM), and 15b ($IC_{50}$=4,397 nM).

$EC_{50}$ values of compounds 18-103 were obtained using OVCAR8 cells. See, Table 4.

TABLE 4

| Compound | R | $EC_{50}$ (nM) |
|---|---|---|
| 18 | cyclobutyl-OMe | |
| 19 (cis) | cyclobutyl-OMe | 17.09 ± 1.2 |
| 20 (trans) | | 72.25 ± 1.2 |
| 21 | cyclopentyl-OMe | 16.96 ± 1.2 |
| 22 | cyclohexyl-OMe | 16.17 ± 1.2 |
| 23 | azetidinyl-OMe | 71.49 ± 1.2 |
| 24 | pyrrolidinyl-OMe | 37.31 ± 1.2 |

TABLE 4-continued

| Compound | R | EC$_{50}$ (nM) |
|---|---|---|
| 25 | (4-methoxy-azepan-1-yl) | 20.16 ± 1.3 |
| 26 | (3-(2-fluoroethoxy)azetidin-1-yl) | 74.07 ± 1.3 |
| 27 | (3-(2-[$^{18}$F]fluoroethoxy)azetidin-1-yl) | |
| 28 (R) | (3-(2-fluoroethoxy)pyrrolidin-1-yl) | 30.85 ± 1.2 |
| 29 (S) | | 56.64 ± 1.2 |
| 30 | (3-(2-[$^{18}$F]fluoroethoxy)pyrrolidin-1-yl) | |
| 31 | (4-(2-fluoroethoxy)piperidin-1-yl) | 17.09 ± 1.2 |
| 32 | (4-(2-[$^{18}$F]fluoroethoxy)piperidin-1-yl) | |
| 33 | (4-(2-fluoroethoxy)azepan-1-yl) | 11.28 ± 1.3 |
| 34 | (4-(2-[$^{18}$F]fluoroethoxy)azepan-1-yl) | |

TABLE 4-continued
| Compound | R | EC$_{50}$ (nM) |
|---|---|---|
| 35 | 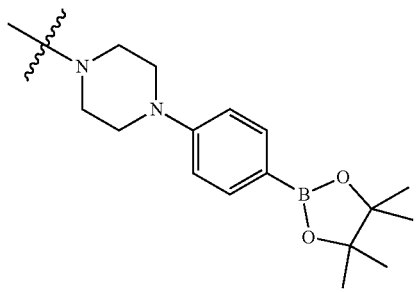 [SMILES: *N1CCN(c2ccc(B3OC(C)(C)C(C)(C)O3)cc2)CC1] | |
| 36 | 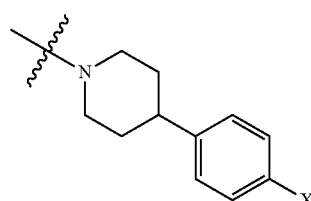  X = $^{18}$F, $^{123}$I, $^{124}$I, $^{125}$I, $^{131}$I, $^{76}$Br, $^{77}$Br, $^{211}$At | |
| 37 | CHOCH$_2$CH$_2$CH$_2$F | 61.5 ± 1.2 |
| 38 | CHOCH$_2$CH$_2$CH$_2$$^{18}$F | |
| 39 | 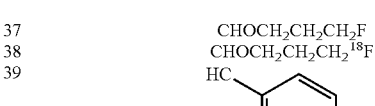 | |
| 40 | 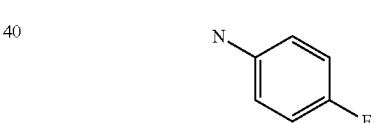 | 11.98 ± 1.2 |
| 41 | 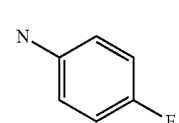 | |
| 42 | 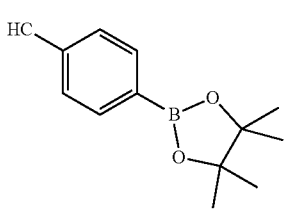 | |
| 43 | 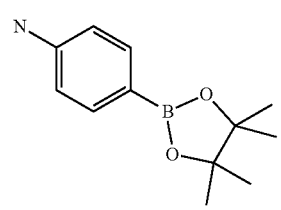  X = $^{18}$F, $^{123}$I, $^{124}$I, $^{125}$I, $^{131}$I, $^{76}$Br, $^{77}$Br, $^{211}$At | |
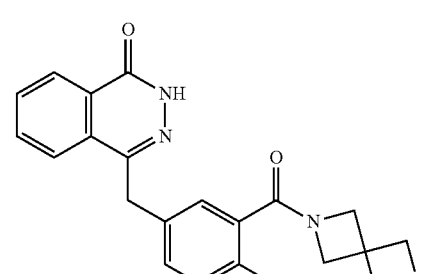

TABLE 4-continued
| Compound | R | EC$_{50}$ (nM) |
|---|---|---|
| 44 | 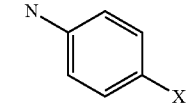  X = $^{18}$F, $^{123}$I, $^{124}$I, $^{125}$I, $^{131}$I, $^{76}$Br, $^{77}$Br, $^{211}$At | |
| 45 | 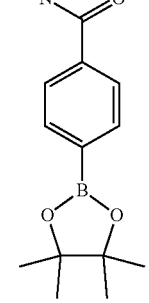 | |
| 46 | 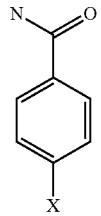 | (X = F) 36.02 ± 1.2 |
| 47 | CHOCH$_2$CH$_2$CH$_2$F | |
| 48 | CHOCH$_2$CH$_2$CH$_2$$^{18}$F | |
| 49 | 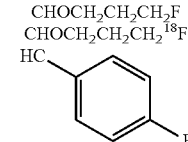 | |
| 50 | 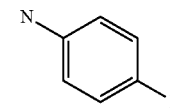 | |
| 51 | 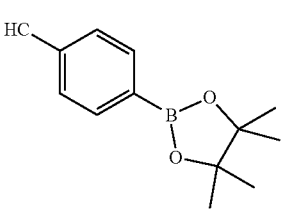 | |
| 52 | 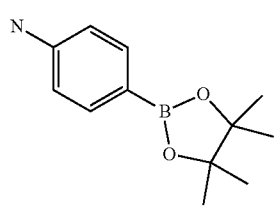 | |

TABLE 4-continued

| Compound | R | EC$_{50}$ (nM) |
|---|---|---|
| 53 | HC—C$_6$H$_4$—X; X = $^{18}$F, $^{123}$I, $^{124}$I, $^{125}$I, $^{131}$I, $^{76}$Br, $^{77}$Br, $^{211}$At | |
| 54 | N≡C—C$_6$H$_4$—X; X = $^{18}$F, $^{123}$I, $^{124}$I, $^{125}$I, $^{131}$I, $^{76}$Br, $^{77}$Br, $^{211}$At | |
| 55 | CHOCH$_2$CH$_2$CH$_2$F | |
| 56 | CHOCH$_2$CH$_2$CH$_2$$^{18}$F | |
| 57 | HC—C$_6$H$_4$—F | |
| 58 | N≡C—C$_6$H$_4$—F | |
| 59 | HC—C$_6$H$_4$—Bpin | |
| 60 | N≡C—C$_6$H$_4$—Bpin | |
| 61 | HC—C$_6$H$_4$—X; X = $^{18}$F, $^{123}$I, $^{124}$I, $^{125}$I, $^{131}$I, $^{76}$Br, $^{77}$Br, $^{211}$At | |
| 62 | N≡C—C$_6$H$_4$—X; X = $^{18}$F, $^{123}$I, $^{124}$I, $^{125}$I, $^{131}$I, $^{76}$Br, $^{77}$Br, $^{211}$At | |

TABLE 4-continued
| Compound | R | EC$_{50}$ (nM) |
|---|---|---|
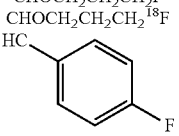
| 63 | CHOCH$_2$CH$_2$CH$_2$F | |
| 64 | CHOCH$_2$CH$_2$CH$_2$$^{18}$F | |
| 65 | 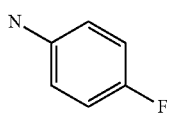 | |
| 66 | 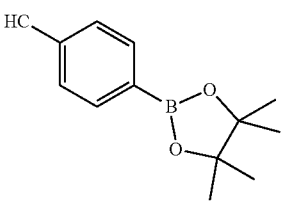 | |
| 67 | 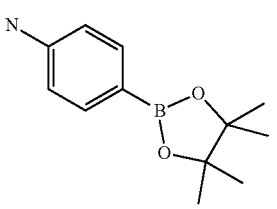 | |
| 68 | 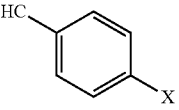 | |
| 69 | 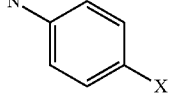<br>X = $^{18}$F, $^{123}$I, $^{124}$I,<br>$^{125}$I, $^{131}$I, $^{76}$Br,<br>$^{77}$Br, $^{211}$At | |
| 70 | 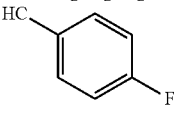<br>X = $^{18}$F, $^{123}$I, $^{124}$I,<br>$^{125}$I, $^{131}$I, $^{76}$Br,<br>$^{77}$Br, $^{211}$At | |
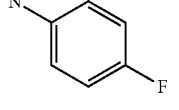
| 71 | CHOCH$_2$CH$_2$CH$_2$F | |
| 72 | CHOCH$_2$CH$_2$CH$_2$$^{18}$F | |
| 73 | (4-fluorobenzyl) | |
| 74 | (4-fluoroanilino) | |

TABLE 4-continued
| Compound | R | EC$_{50}$ (nM) |
|---|---|---|
| 75 | 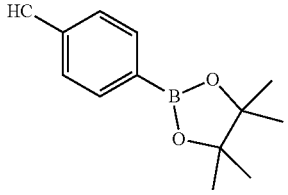 | |
| 76 | 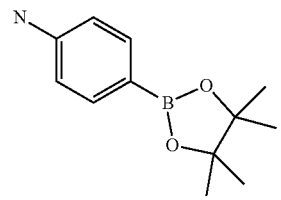 | |
| 77 | 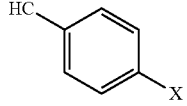<br>X = $^{18}$F, $^{123}$I, $^{124}$I,<br>$^{125}$I, $^{131}$I, $^{76}$Br,<br>$^{77}$Br, $^{211}$At | |
| 78 | 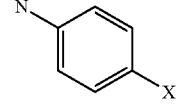<br>X = $^{18}$F, $^{123}$I, $^{124}$I,<br>$^{125}$I, $^{131}$I, $^{76}$Br,<br>$^{77}$Br, $^{211}$At | |
| 79 | CHOCH$_2$CH$_2$CH$_2$F | |
| 80 | CHOCH$_2$CH$_2$CH$_2$$^{18}$F | |
| 81 | 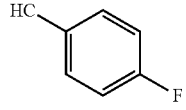 | |
| 82 | 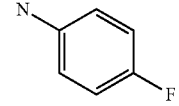 | |
| 83 | 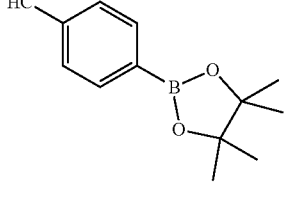 | |
| 84 | 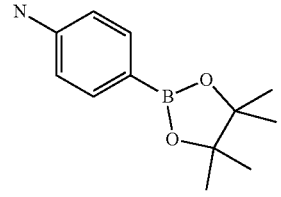 | |

TABLE 4-continued
| Compound | R | EC$_{50}$ (nM) |
|---|---|---|
| 85 | 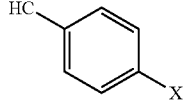 X = $^{18}$F, $^{123}$I, $^{124}$I, $^{125}$I, $^{131}$I, $^{76}$Br, $^{77}$Br, $^{211}$At | |
| 86 | 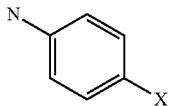 X = $^{18}$F, $^{123}$I, $^{124}$I, $^{125}$I, $^{131}$I, $^{76}$Br, $^{77}$Br, $^{211}$At | |
| 87 | CHOCH$_2$CH$_2$CH$_2$F | |
| 88 | CHOCH$_2$CH$_2$CH$_2$$^{18}$F | |
| 89 | 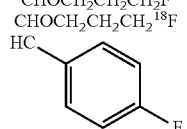 | |
| 90 | 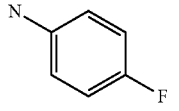 | |
| 91 | 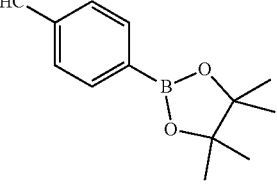 | |
| 92 | 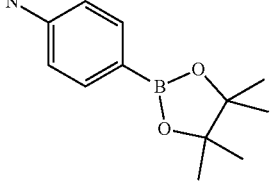 | |
| 93 | 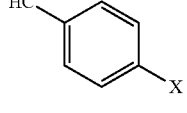 X = $^{18}$F, $^{123}$I, $^{124}$I, $^{125}$I, $^{131}$I, $^{76}$Br, $^{77}$Br, $^{211}$At | |
| 94 | 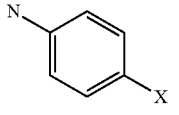 | |

TABLE 4-continued

| Compound | R | EC$_{50}$ (nM) |
|---|---|---|
| 95 | CHOCH$_2$CH$_2$CH$_2$F | |
| 96 | CHOCH$_2$CH$_2$CH$_2$$^{18}$F | |
| 97 | HC—C$_6$H$_4$—F (4-fluorophenyl, HC linker) | |
| 98 | N—C$_6$H$_4$—F (4-fluoroanilino) | |
| 99 | HC—C$_6$H$_4$—Bpin (pinacol boronate) | |
| 100 | N—C$_6$H$_4$—Bpin (pinacol boronate) | |
| 102 | HC—C$_6$H$_4$—X; X = $^{18}$F, $^{123}$I, $^{124}$I, $^{125}$I, $^{131}$I, $^{76}$Br, $^{77}$Br, $^{211}$At | |
| 103 | N—C$_6$H$_4$—X; X = $^{18}$F, $^{123}$I, $^{124}$I, $^{125}$I, $^{131}$I, $^{76}$Br, $^{77}$Br, $^{211}$At | |

Core structure: phthalazin-1(2H)-one-CH$_2$-(2-fluoro-phenyl)-C(O)-N(2,8-diazaspiro[5.5]undecane)-R

Example 7: PARP Specificity

Figure 2A:
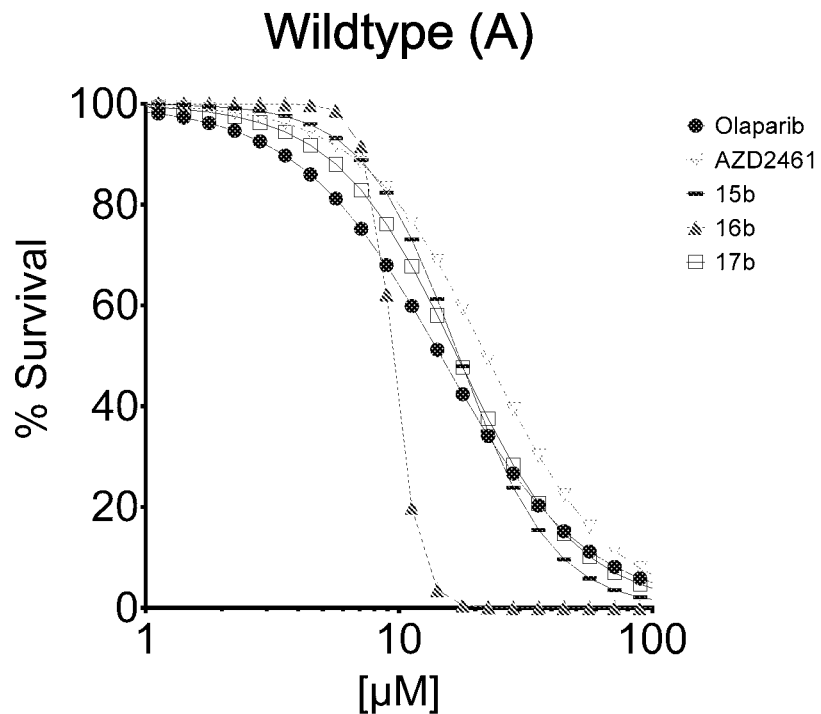
FIGS. 2A-2C depict dose response curves showing the relative potency of compounds 15b-17b vs. olaparib and AZD2461 in mouse embryonic fibroblasts PARP-1 and PARP-2 KO cells.
Figure 2B:
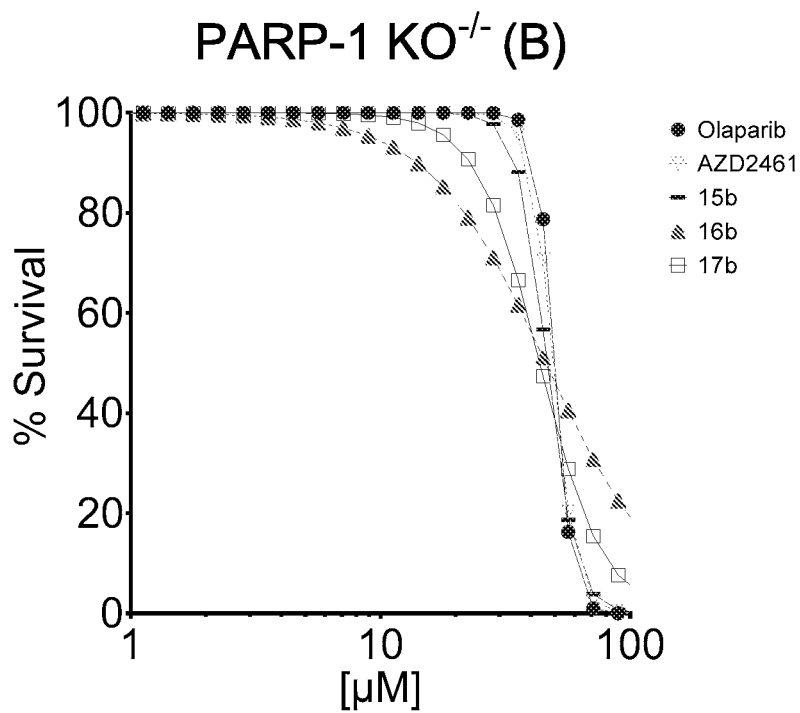
Figure 2C:
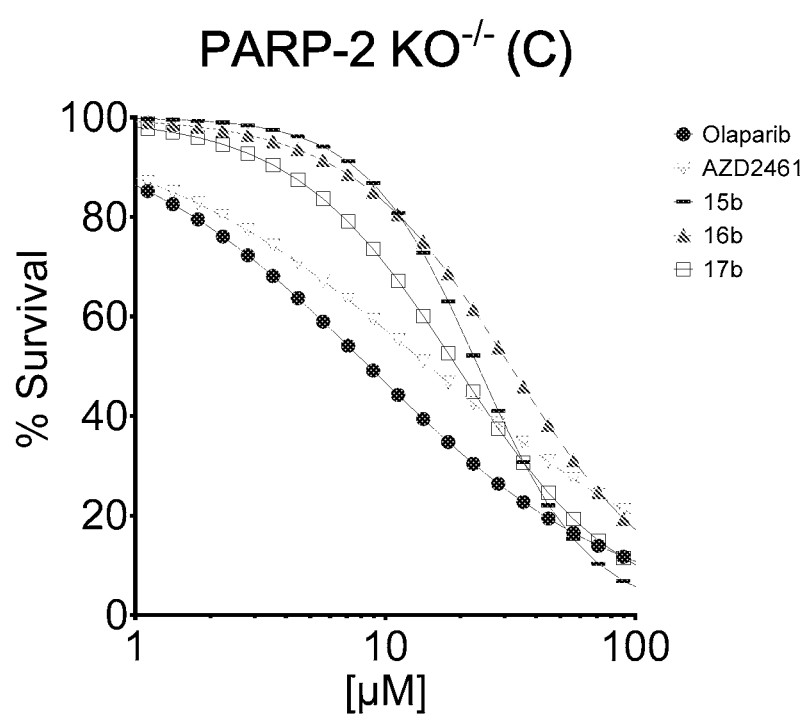
Figure 3:
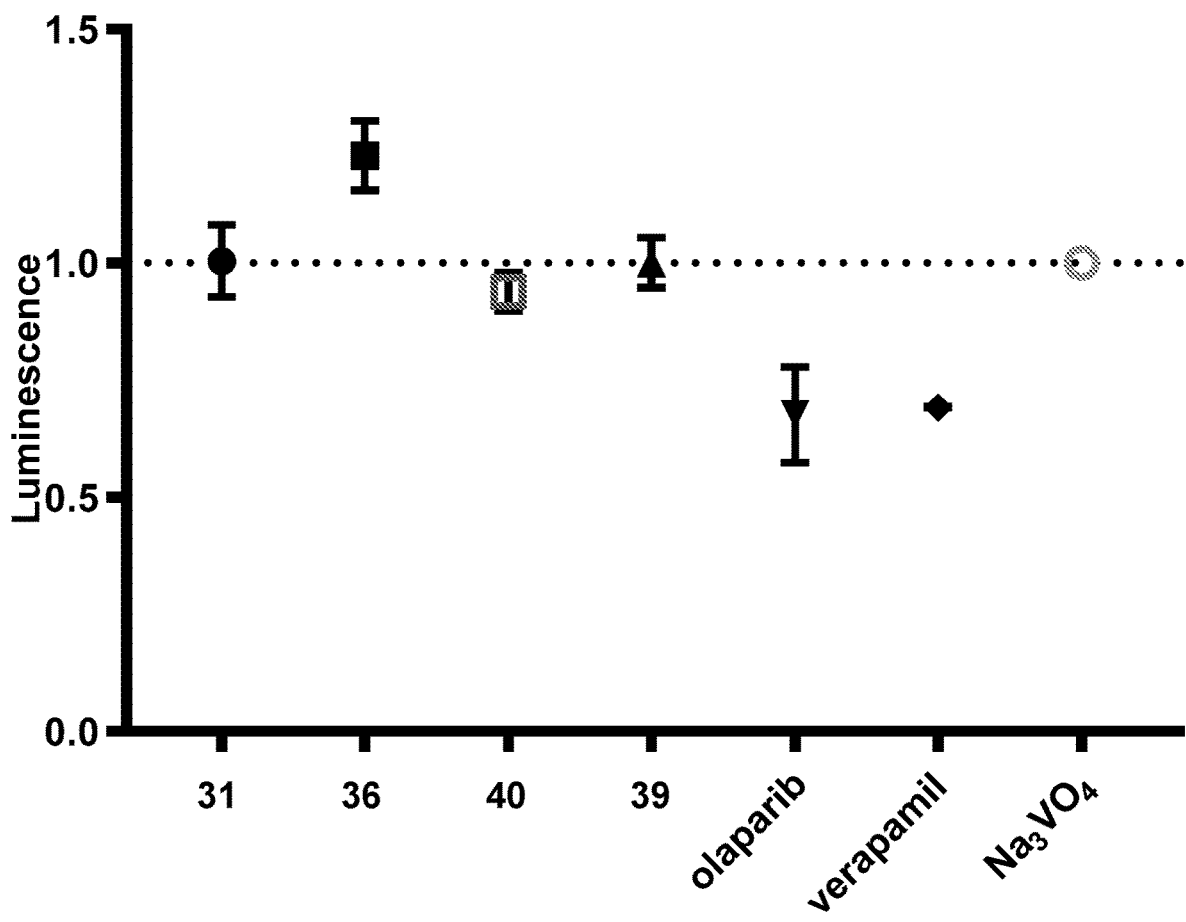
FIG. 3 is a dot plot comparing the luminescence generated with compounds 31, 36, 40, and 39, olaparib, Verapamil, and $Na_3VO_4$.

PARP specificity of compounds 10-17, along with olaparib and AZD2461, was then performed using cell viability assays with MEF WT, MEF PARP-1 KO$^{-/-}$, and MEF PARP-2 KG-cell lines as described above. This isogenic model was selected due to the highly conserved nature of the PARP catalytic domain, all-owing investigation in enzyme specificity. Genetic cross breading of PARP-1/2 heterozygous null mice resulted in double-knockout mice, from which MEF cell lines were harvested. The results are outlined in Table 5 and FIGS. 2A-2C, illustrating a dose-response curve featuring the most active compounds, 15b-17b, in addition to olaparib and AZD2461. EC$_{50}$ values obtained from the other compounds included in this study can be found in Table 5.

Impressive anti-proliferative activity was observed with compounds 15b-17bin cell viability assay using MEF WT cell line (FIG. 2A), when compared to FDA approved olaparib and AZD2461. Compared to the EC$_{50}$ values obtained with olaparib and AZD2461, (14.6 μM and 22.1 μM, respectively), compound 16b exhibited an EC$_{50}$ value of 9.4 μM in the MEF WT assay. In addition, compounds 15b (17.2 μM) and 17b (16.9 μM) were comparable to olaparib and also performed better than AZD2461. PARP-1 affinity compounds 12b and 13b demonstrated EC$_{50}$ values~23 μM, continuing this unexpected trend in cell activity.

Example 8

Enzyme dependency of selected compounds in MEF PARP-1 KO−/− cells (FIG. 2B) was performed as described above in order to identify if these analogues act through other cellular targets. In comparison to olaparib and AZD2461, a noticeable decrease in in cell inhibition was observed for compounds 15b-17b in the PARP-1 knockout cell line (46.4 µM, 45.9 µM, and 43.4 µM, respectively). These results suggest the mechanism of cell inhibition of these compounds is indeed PARP-1 dependent. See, Table 5.

The cell cytotoxicity profile of these selected compounds in MEF PARP-2 KO−/− cell lines was then analyzed as described above. The results showed that cell cytotoxicity improved for olaparib and AZD2461 in the knockdown assay. Compounds 15b-17b also performed better in terms of toxicity, in the PARP-1 knockout cell line, however, in comparison to the MEF WT cell assay, the $EC_{50}$ values of these analogues were slightly higher (23.4 µM, 31.6 µM, and 19.2 µM, respectively). This is in contrast to the slight increase in cytotoxicity observed by olaparib and AZD2461 in the PARP-2 KO−/− vs. the MEF WT assay. See, Table 5

TABLE 5

| Compound | WT | PARP-1−/− $EC_{50}$ (µM) | PARP-2−/− |
|---|---|---|---|
| olaparib | 14.6 | 49.6 | 8.5 |
| 10a | 48.3 | NA | 49.0 |
| 10b | 52.2 | NA | 53.3 |
| 10c | 31.1 | NA | 24.7 |
| 10d | NA | NA | NA |
| 10e | NA | NA | 59.8 |
| 11a | 48.0 | NA | 58.3 |
| 11b | 42.9 | NA | 35.8 |
| 11c | NA | NA | NA |
| 11d | 53.2 | NA | 46.7 |
| 12a | 25.6 | 48.3 | 39.9 |
| 12b | 23.4 | 49.2 | 41.5 |
| 12c | NA | NA | 68.5 |
| 12d | 49.3 | NA | 57.2 |
| 13a | 32.6 | NA | 78.8 |
| 13b | 23.3 | NA | 33.2 |
| 13c | NA | NA | 105.9 |
| 13d | 47.5 | NA | 44.4 |
| AZD2461 | 22.1 | 49.0 | 14.9 |
| 14a | 45.2 | NA | 54.7 |
| 14b | 29.2 | NA | 31.8 |
| 14c | NA | NA | NA |
| 14d | NA | NA | 61.8 |
| 15a | 31.7 | NA | 55.5 |
| 15b | 17.2 | 46.4 | 23.4 |
| 15c | NA | NA | 511.6 |
| 15d | NA | NA | 70.9 |
| 16a | 42.7 | 51.6 | 46.8 |
| 16b | 9.4 | 45.9 | 31.6 |
| 16c | NA | NA | NA |
| 16d | 41.6 | NA | 61.0 |
| 17a | 41.3 | NA | 41.3 |
| 17b | 16.9 | 43.4 | 19.2 |
| 17c | NA | NA | 59.7 |
| 17d | 24.8 | 49.7 | 21.6 |

[a]$EC_{50}$ data for compounds in mouse embryonic fibroblasts PARP-1 and PARP-2 KO−/− cells.
NA = Not applicable, no cell death observed.

Example 8: Radiochemistry

Radiolabeling precursors for [$^{18}$F]31 were initially prepared by coupling commercially available compound 9 with 2-(piperidin-4-yloxy)ethan-1-ol, in the presence of HOBt, EDC, TEA in THF, to obtain intermediate AA in moderate yield. See, Scheme 7. Next, AA was reacted with 4-toluenesulfonyl chloride or methanesulfonyl chloride to afford precursors BB and CC, respectively. Access to [$^{18}$F]31 was then achieved in a facile one-step radiolabeling strategy using precursor BB. Although not optimized, this method afforded a radiochemical yield of 8-12% for [$^{18}$F]31, with a specific activity of 8,491 Ci/mmol (n=2). The mesylate precursor CC was also evaluated, however, low radiochemical yields were obtained (~1-3%).

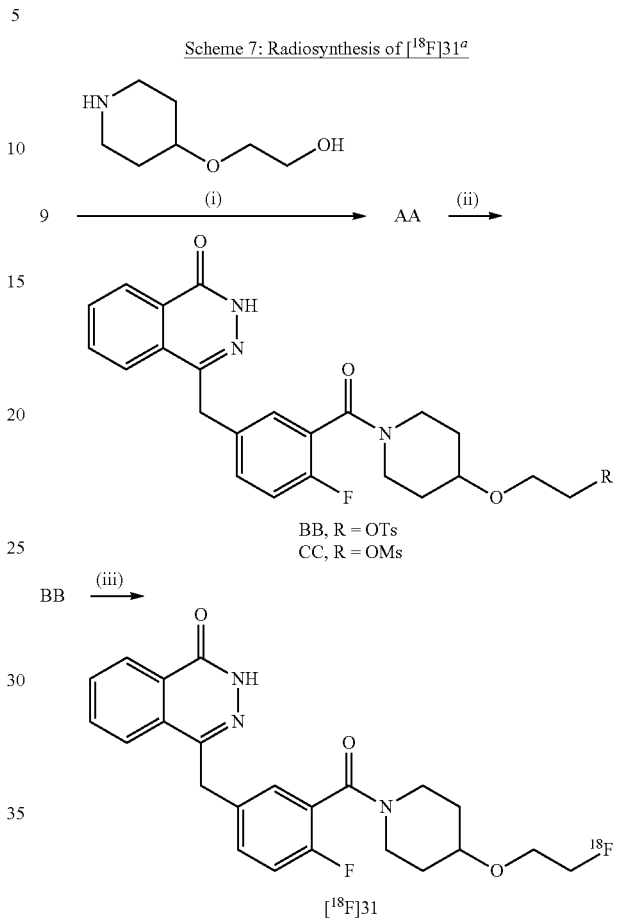

Scheme 7: Radiosynthesis of [$^{18}$F]31[a]

[a]Reagents and conditions: (i) 8, 2-(piperidin-4-yloxy)ethan-1-ol, HOBt hydrate, EDC HCl, TEA, THF, 60° C., 12 h; (ii) TsCl or MsCl, TEA, DCM, 12 h; (iii) [$^{18}$F]KF, K$_{222}$, K$_2$CO$_3$, DMSO, 120° C., 20 min.

Example 9: In Vitro Autoradiography

Figure 4:
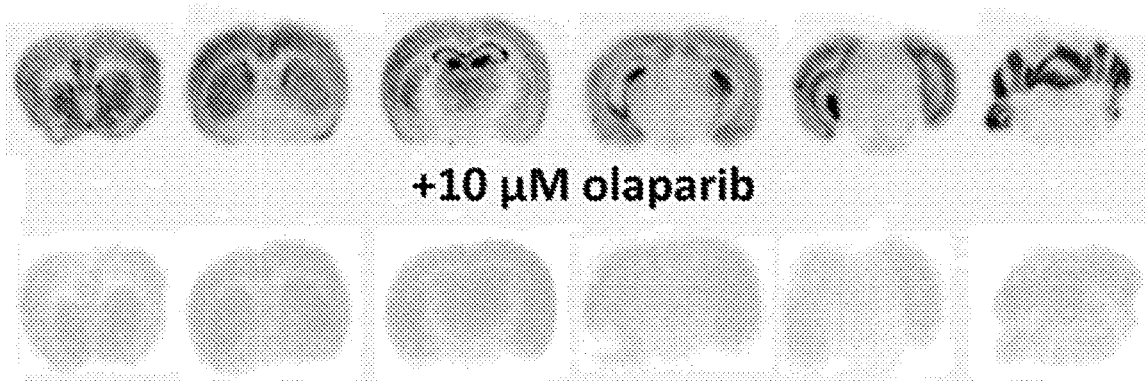
FIG. 4A are brain sections of Balb/c mice showing bind specificity of compound [$^{18}$F]31 and FIG. 4B is a bar graph comparing compound [$^{18}$F]31 and olaparib.
Figure 4:
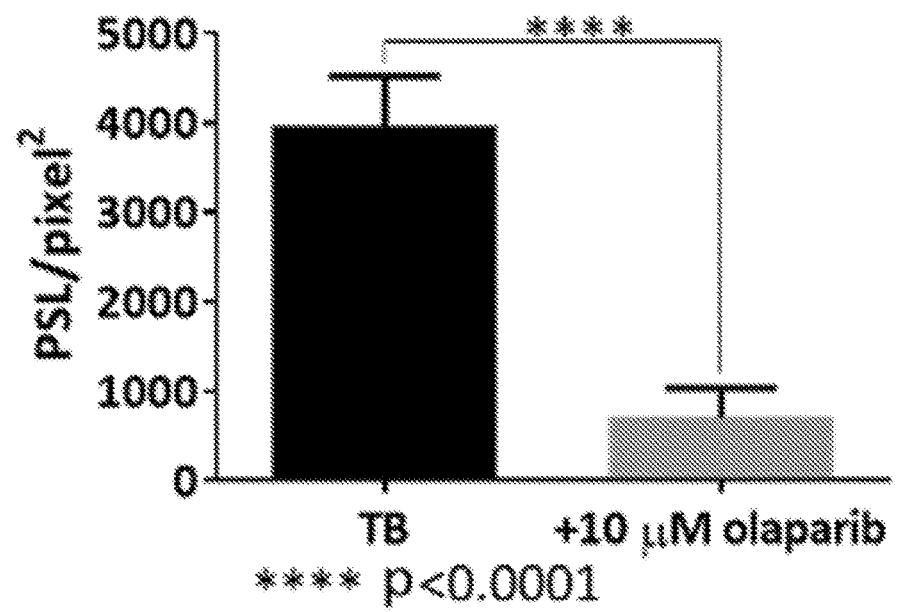

In vitro autoradiography was performed with brain sections from Balb/c mice to verify binding specificity of radio-labeled compound [$^{18}$F]31 (FIGS. 4A and 4B). The distribution of [$^{18}$F]31 was found to be mostly conserved in the cortex, hippocampus, and cerebellum. Olaparib was utilized as the blocking agent to screen any non-specific binding of the radioligand.

Example 10: MicroPET Imaging

Small animal PET imaging studies using rhesus macaques were conducted with compound [$^{18}$F]31 and [$^{18}$F]FTT, a PARP-1 PET tracer under clinical investigation known to be a Pg-p substrate as described in Michel et al., "PET of Poly (ADP-Ribose) Polymerase Activity in Cancer: Preclinical Assessment and First In-Human Studies," Radiology, 2017, 282, 453,463.

P-gp activity of compounds was measured using Promega Pgp-Glo™ Assay Systems. 25 µg of diluted recombinant human P-gp membranes were added to untreated white opaque multiwell plates along with Pgp-Glo™ Assay Buffer, a non-limiting concentration of ATP (5 mM) and 20 µL of each test compound (20 µM) for 1 hr at 37° C. Untreated and Na₃VO₄-treated control samples were also tested in addition to Verapamil-treated samples (positive control). After incubation, 50 µl of ATP Detection Reagent was added to all wells to stop the P-gp reaction. Samples were mixed briefly on a plate shaker then incubated plate at room temperature for 20 minutes to allow luminescent signal to develop. Luminescence was read on a plate-reading luminometer. This luciferase-based detection reaction provides a linear response to ATP concentration in each sample. Thus any changes in signal directly reflect changes in ATP concentration.

Verapamil, a substrate for P-gp that stimulates P-gp ATPase activity resulting in decreased luminescence, was utilized as a positive control. Increase in luminescence results from the light-generating reaction from luciferase and unmetabolized ATP. Unconsumed ATP indicates a decrease in P-gp ATPase stimulation, rendering the compound as a P-gp inhibitor. Data is normalized to known P-gp inhibitor Na₃VO₄.

Figure 5:
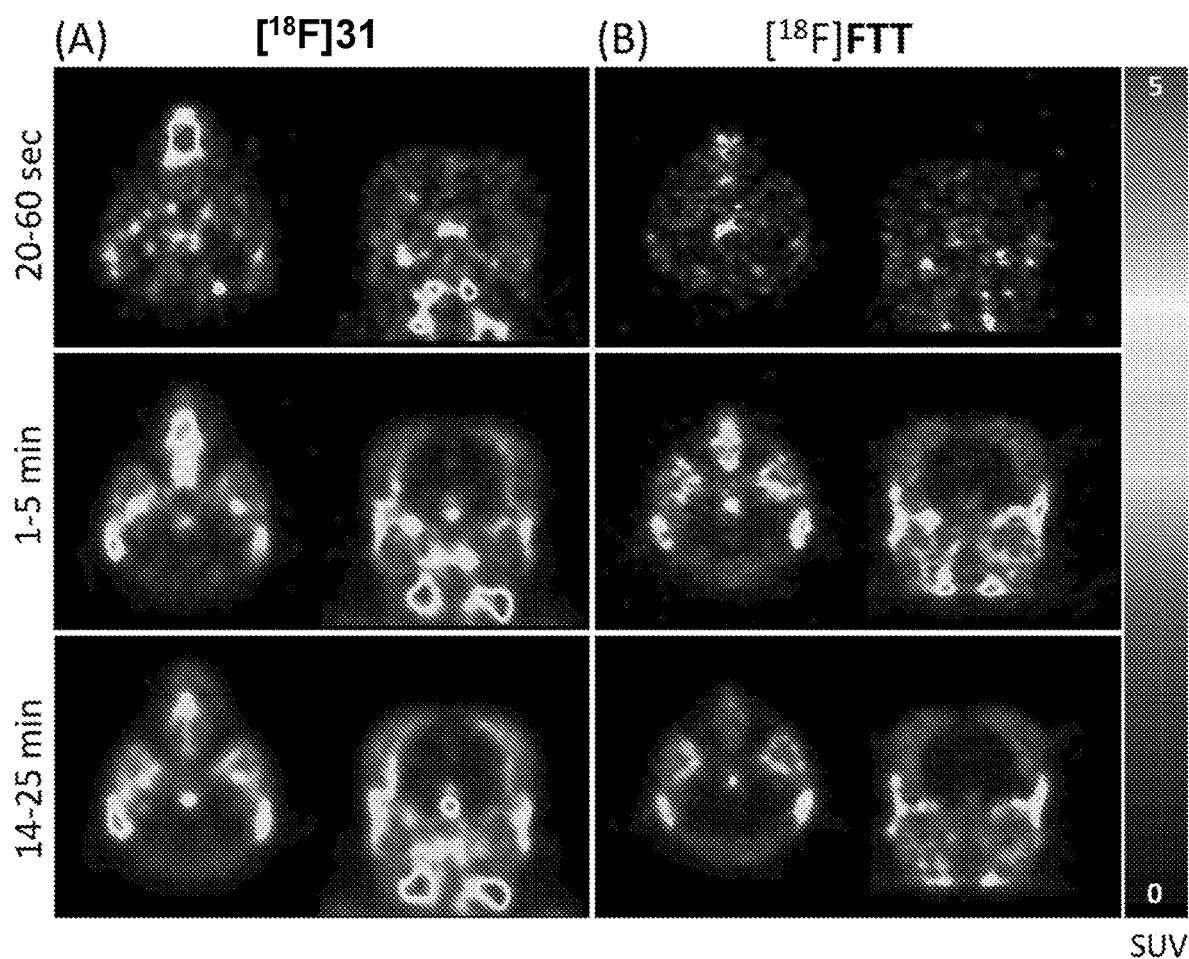
FIG. 5A are monkey brain PET images indicating the low brain uptake of compound [$^{18}$F]31 and FIG. 5B are images [$^{18}$F]FTT indicated by SUV

Despite possessing similar chemical structure and PARP-1 affinity as AZD2461, no appreciable brain uptake of [18F]31 was observed in any of the brain regions (FIG. 5A). These images are similar to the those obtained and expected with [¹⁸F]FTT (FIG. 5B), showing the PARPi to be non-BBB penetrable. Metabolic stability of [¹⁸F]31 was assessed using the monkey blood from each imaging study and found 42% and 45% of the parent compound intact at 40 min and 37 min, respectively.

Rodent studies were then performed with [¹⁸F]31, including control and P-gp knockout (k/o) mice models to validate the tracer as a non-P-gp substrate. However, analysis from select rodent studies showed [¹⁸F]31 to be non-metabolically stable, with over 80% decomposition of the parent compound in both mice blood and brain in just 5 min.

It is to be understood that while the invention has been described in conjunction with the preferred specific embodiments thereof, that the foregoing description and the examples that follow are intended to illustrate and not limit the scope of the invention. It will be understood by those skilled in the art that various changes may be made and equivalents may be substituted without departing from the scope of the invention, and further that other aspects, advantages and modifications will be apparent to those skilled in the art to which the invention pertains. In addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

The disclosures of each patent, patent application, and publication cited or described in this document are hereby incorporated herein by reference, each in its entirety, for all purposes. Also incorporated by reference are Reilly et al., "Synthesis and Evaluation of AZD2461 [¹⁸F]PET Probe in Non-Human Primates Reveals the PARP-1 Inhibitor to be Non-Blood-Brain Barrier Penetrant," Bioor., Chem. March 2019, 83:242-249 (e-publication: Oct. 17, 2018); Reilly et al., "Altering Nitrogen Heterocycles of AZD2461 Affords High Affinity Poly(ADP-ribose) Polymerase-1 Inhibitors with Decreased P-Glycoprotein Interactions," ACS Omega, 2018, 3:9997-10001; and Reilly et al., "Examination of Diazaspiro Cores as Piperazine Bioisosteres in the Olaparib Framework Shows Reduced DNA Damage and Cytotoxicity," J. Med. Chem., June 2018, 61(12):5367-5379.

What is claimed is:

1. A compound of Formula I, or a pharmaceutically acceptable salt thereof:

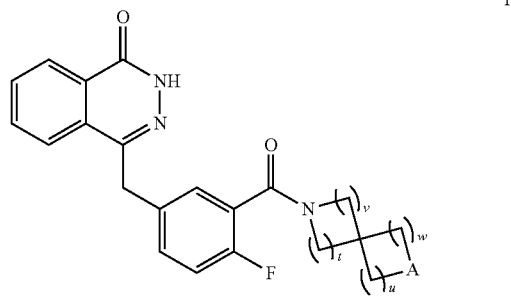

wherein:
A is NR¹, CHR¹, or O;
R¹ is H, alkoxy, aryl, —C(O)(aryl), —C(O)(cycloalkyl), or —C(O)(alkoxy);
t is 1, 2, or 3;
u is 1 or 2;
v is 0, 1, 2 or 3; and
w is 1 or 2;
or an isotopic variant thereof;
or a stereoisomer thereof, or a mixture thereof.

2. The compound of claim 1, wherein A is NR¹.
3. The compound of claim 1, wherein A is CHR¹.
4. The compound of claim 1, wherein A is O.
5. The compound of claim 1, wherein R¹ is H.
6. The compound of claim 1, wherein R¹ is —C(O)(alkoxy).
7. The compound of claim 1, wherein R¹ is —C(O)(cycloalkyl).
8. The compound of claim 1, wherein R¹ is aryl.
9. The compound of claim 1, wherein R¹ is —C(O)(aryl).
10. The compound of claim 1, wherein R¹ is alkoxy.
11. The compound of claim 1, wherein the heterocyclyl is substituted by, one or two substituents that are, independently, (i) C₁₋₆alkoxy, or (iii) substituted phenyl optionally substituted with halo or heterocyclyl.
12. The compound of claim 1, wherein:
t, u, v, and w are 1; or
t is 2, v is 0, and u and w are 1; or
t, u, and w is 1 and v is 2; or
t and v are 1, u and w are 2; or
t, u, and w are 2 and v is 0; or
t is 2, v is 1, u is 1 and w is 1; or
t is 2, v is 1, u is 2, and w is 1; or
t is 2, v is 1, u is 2, and w is 2; or
t and u are 1, and v and w are 2; or
t is 1 and v, U, and w are 2; or
t, v, u, and w are 2.
13. The compound of claim 1, or a pharmaceutically acceptable salt thereof, of the formula:

(IA)
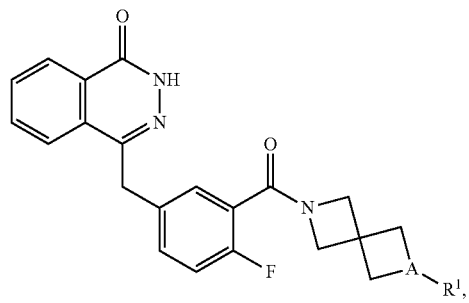
(IB)
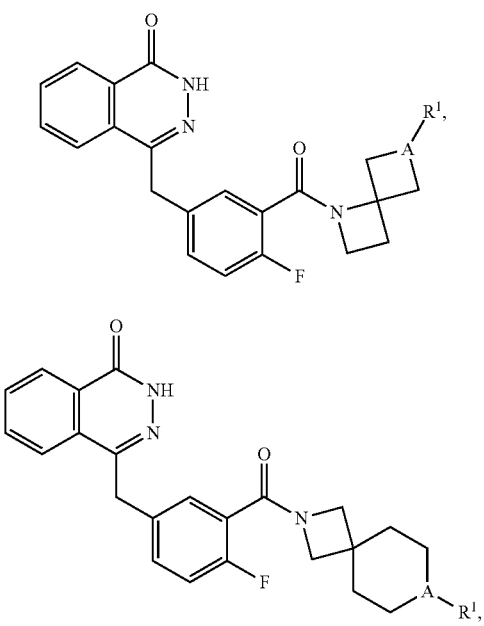
(IC)
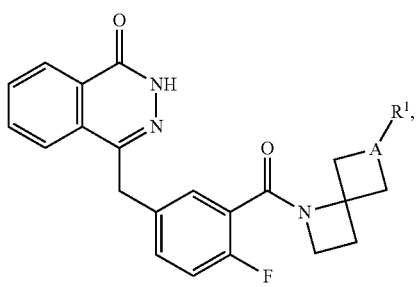
(ID)
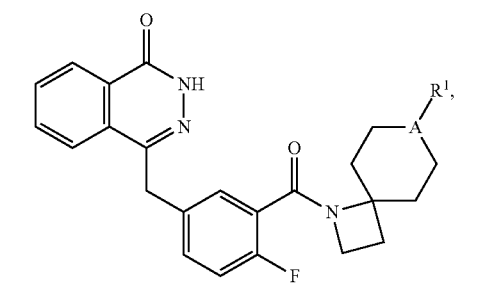
(IE)
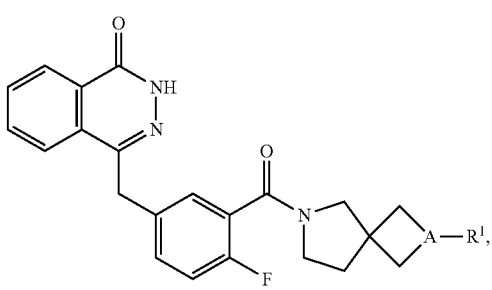
(IF)
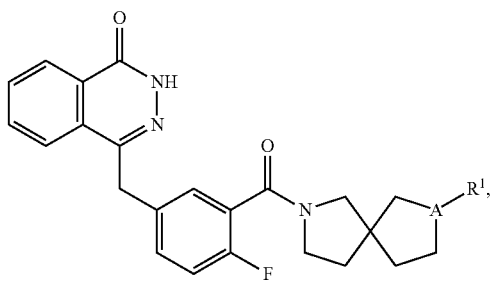
(IG)
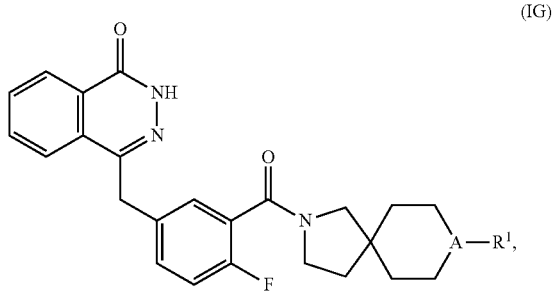
(IH)
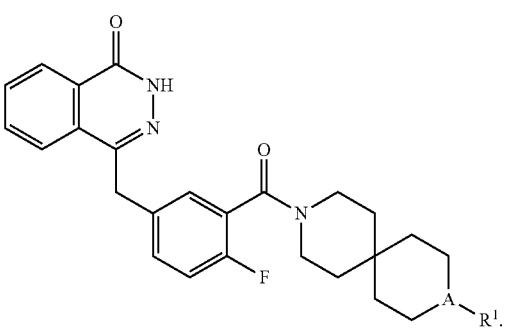
14. The compound of claim 1, or a pharmaceutically acceptable salt thereof, that is:
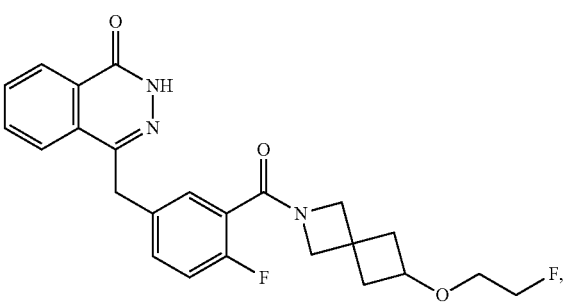

137
-continued
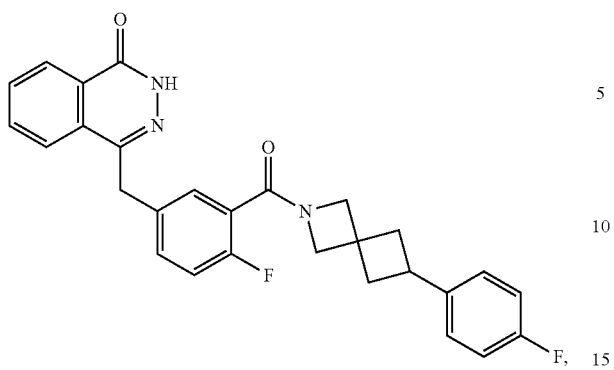
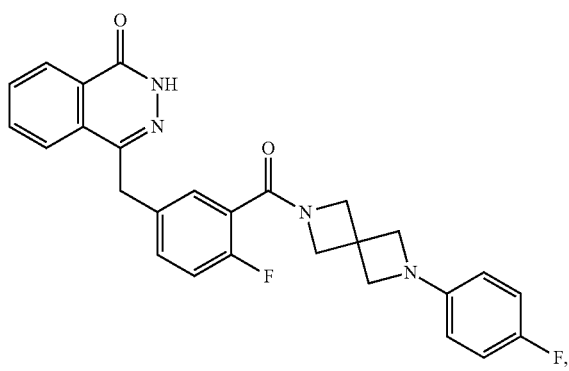
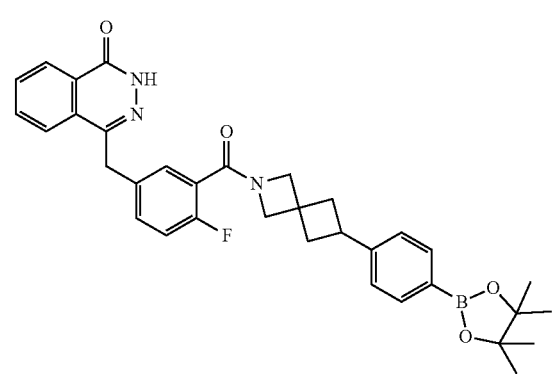
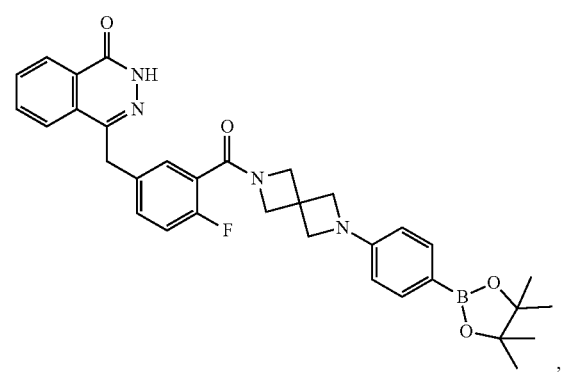
138
-continued
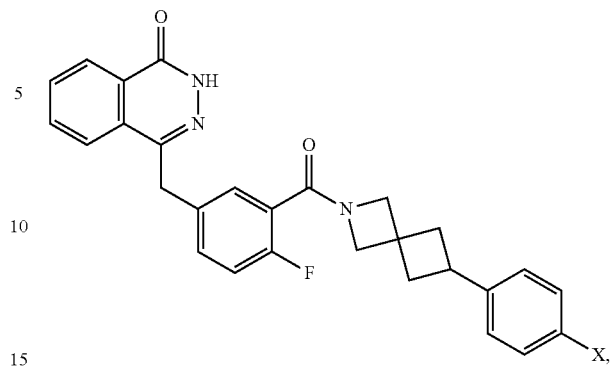
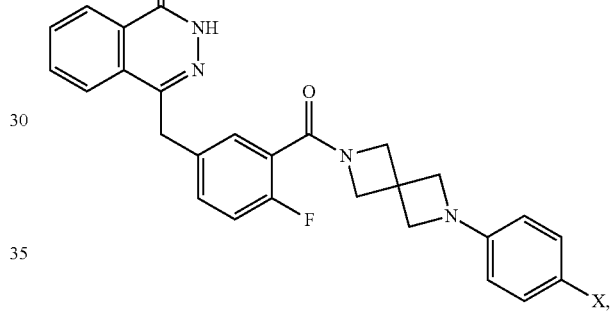
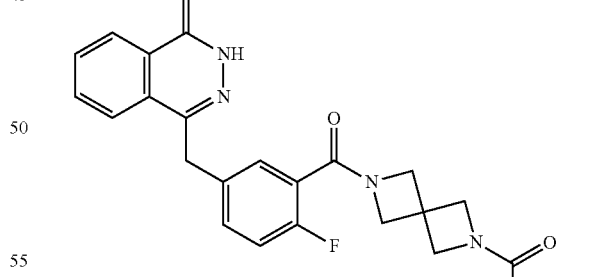

139
-continued
140
-continued
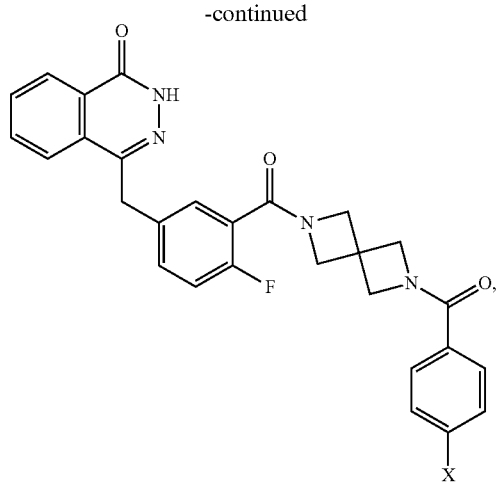
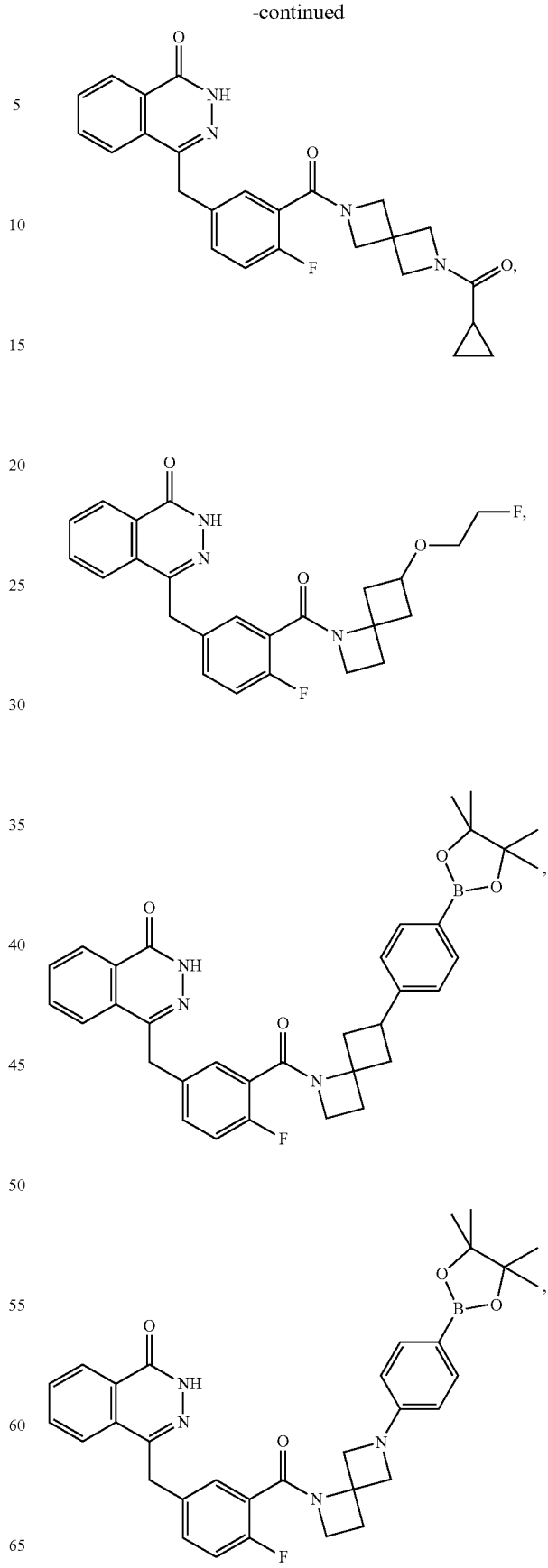

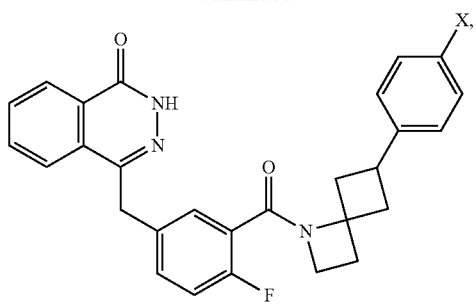
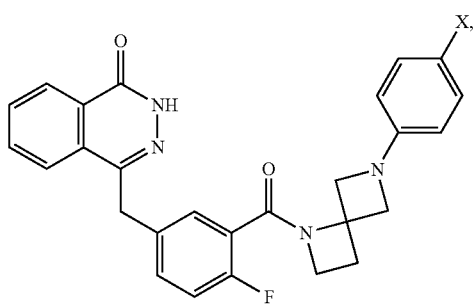
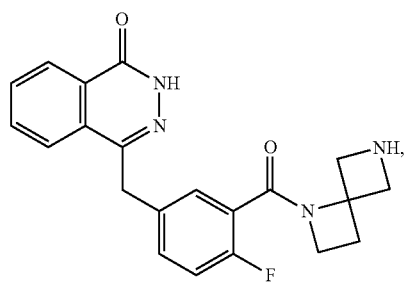
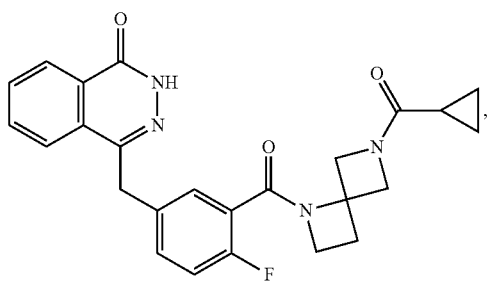
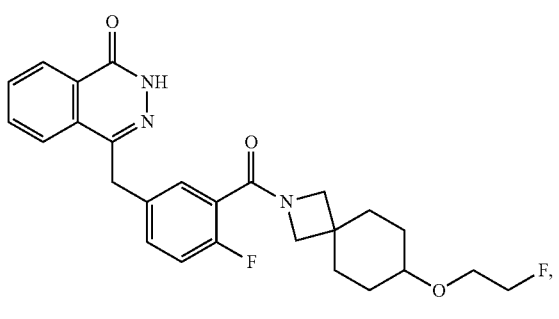
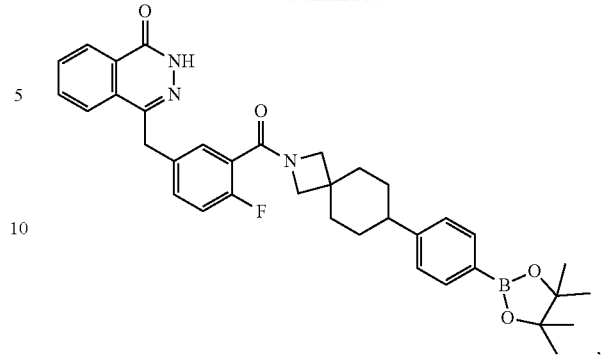
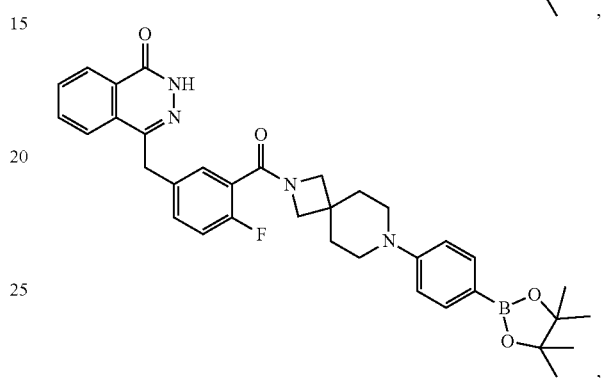
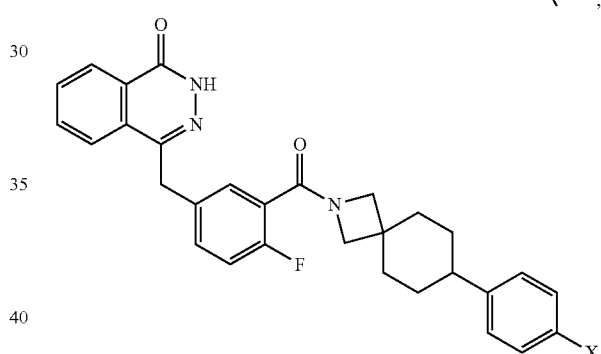
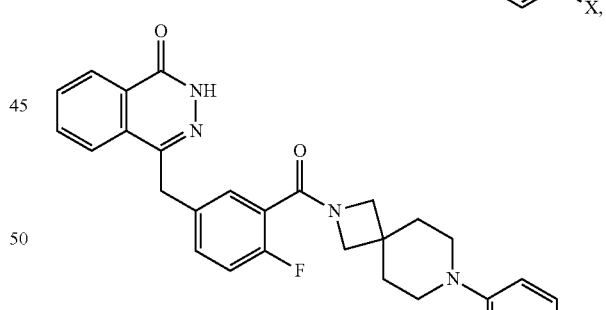
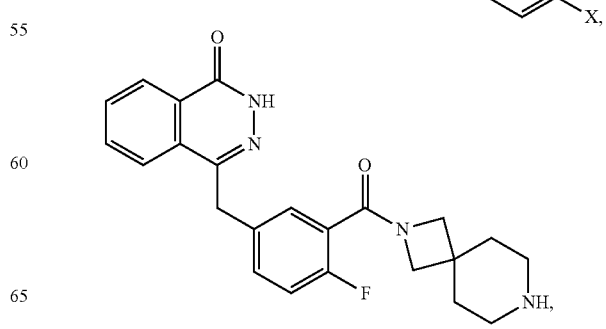

143
-continued
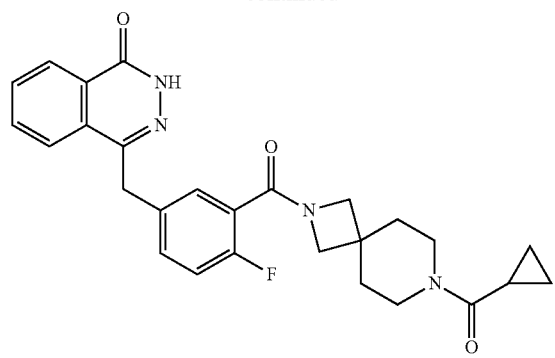
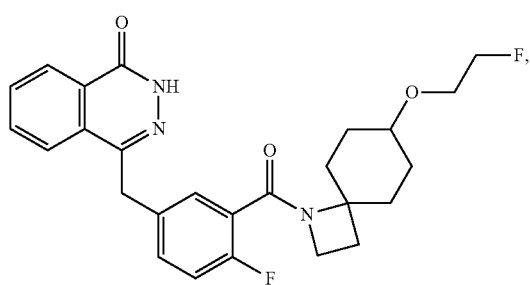
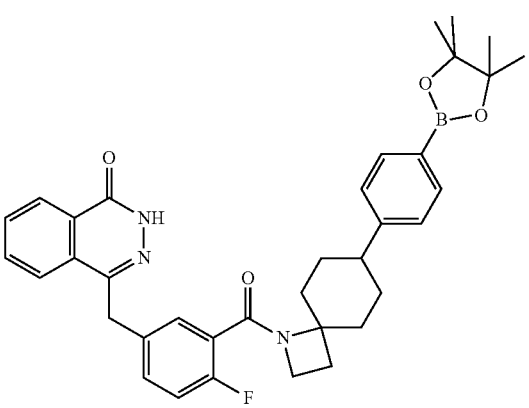
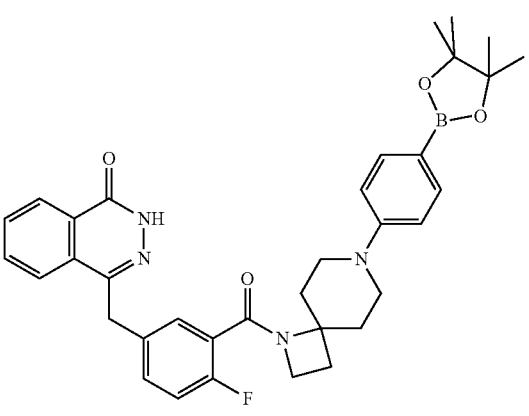
144
-continued
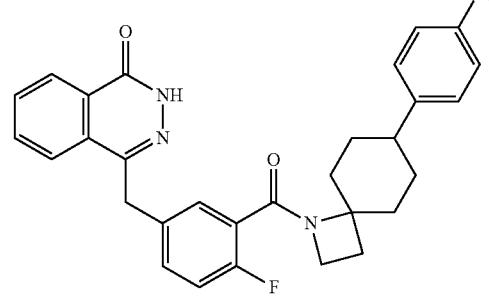
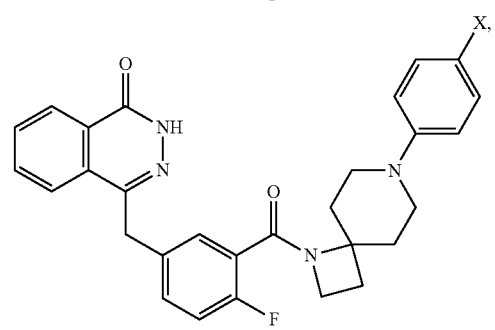
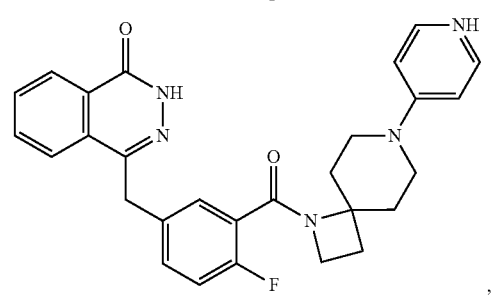
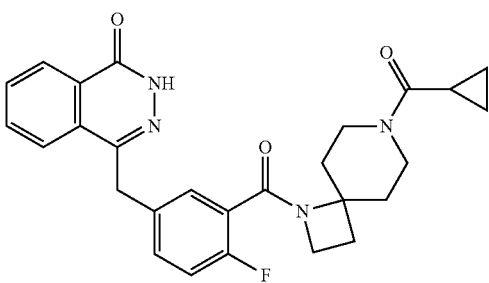
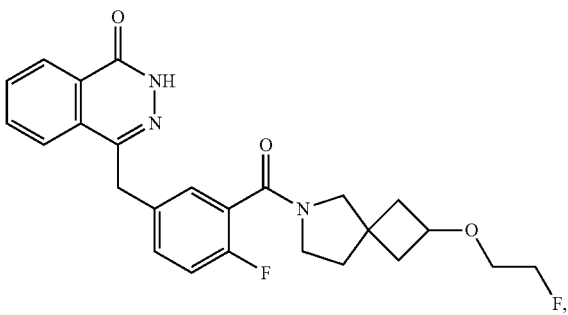

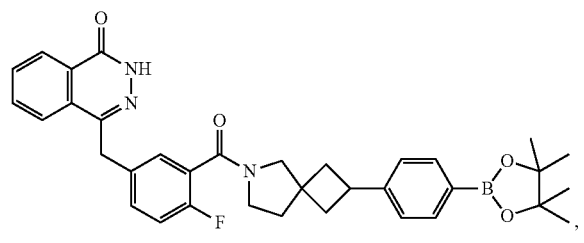
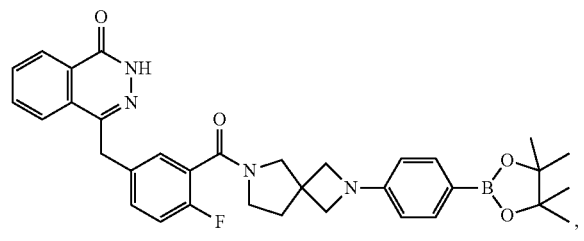
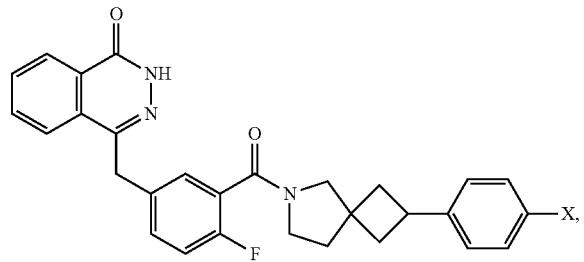
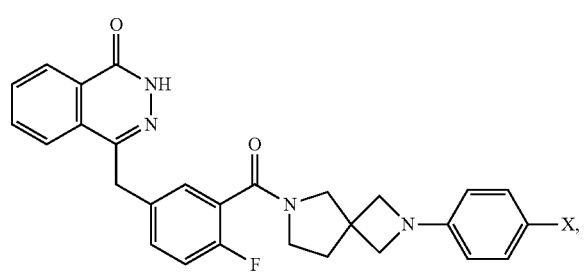
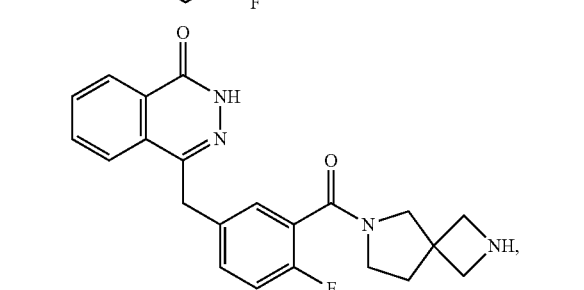
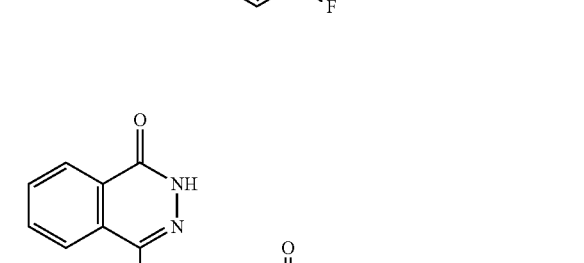
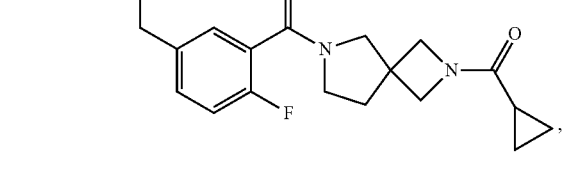
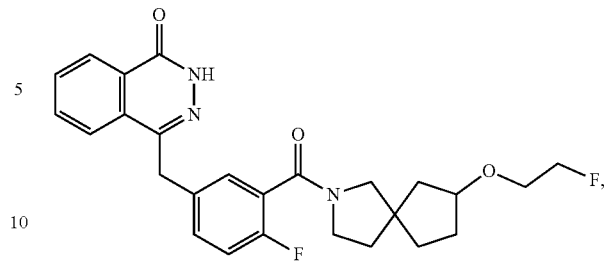
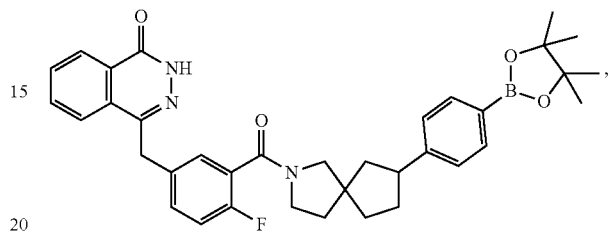
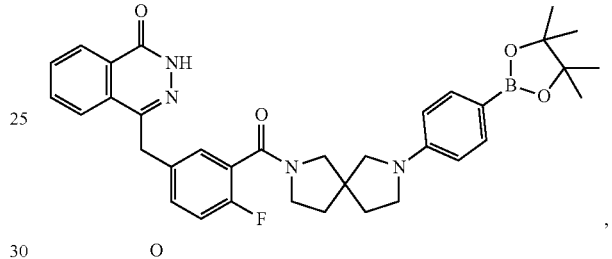
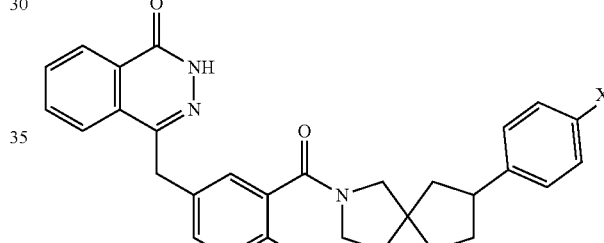
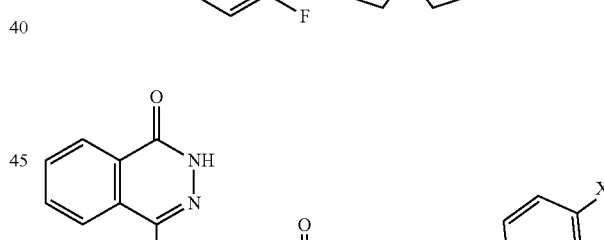
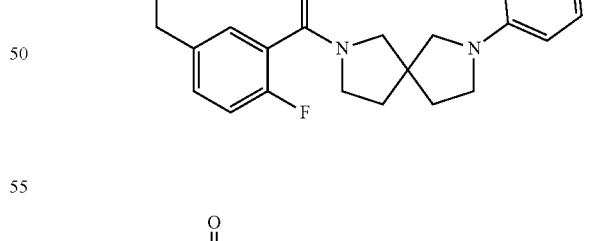
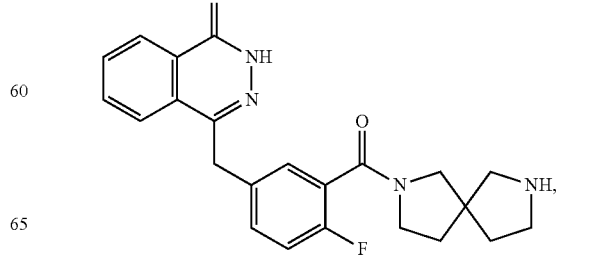

147
-continued
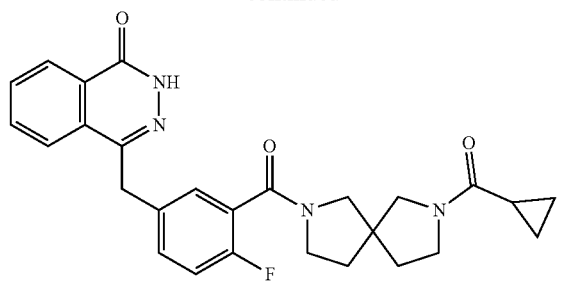
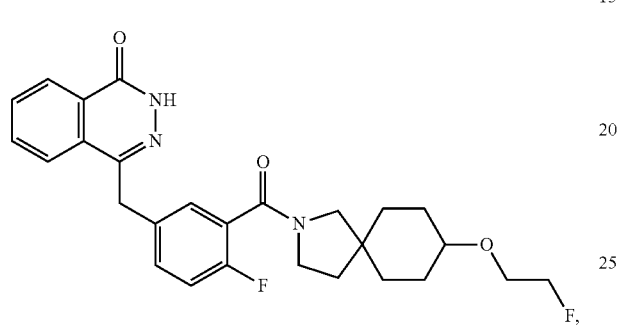
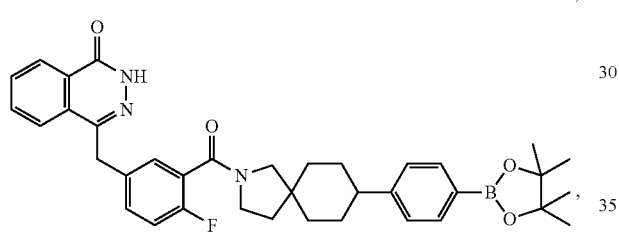
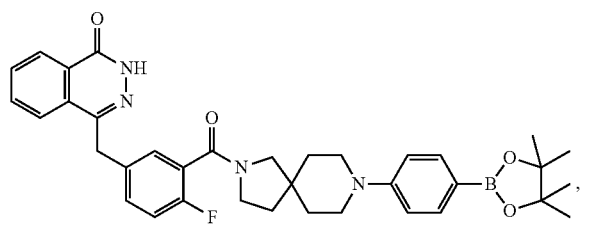
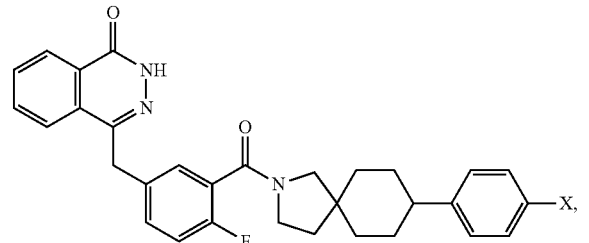
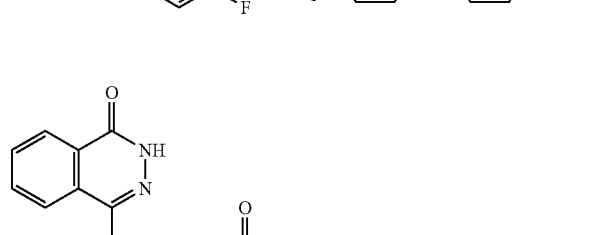
148
-continued
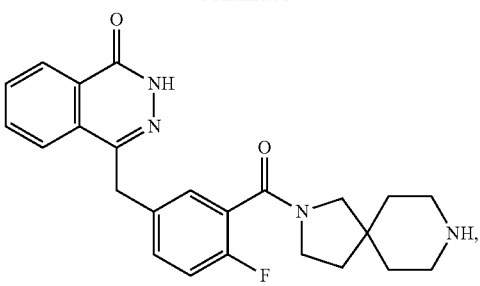
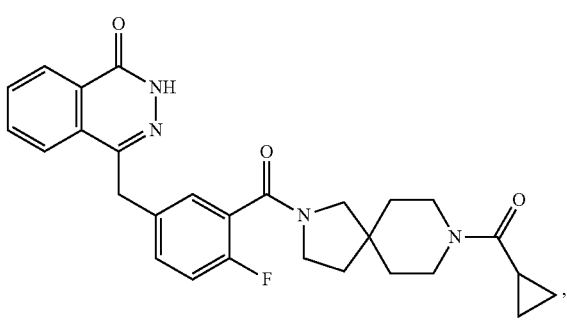
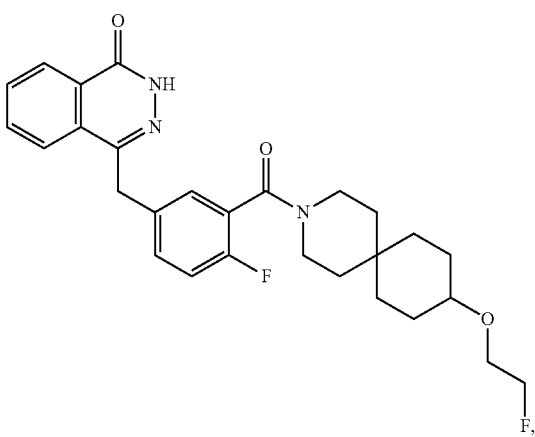
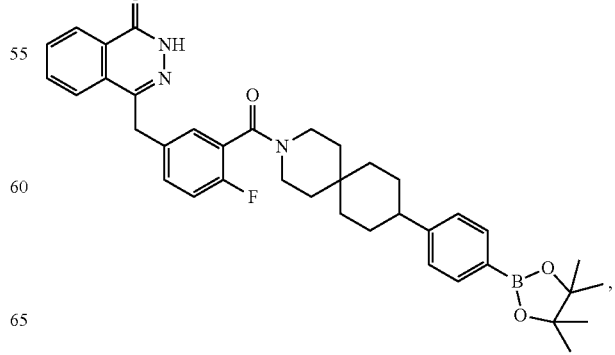

-continued

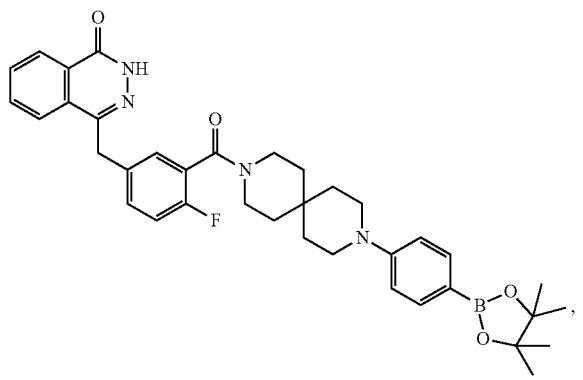

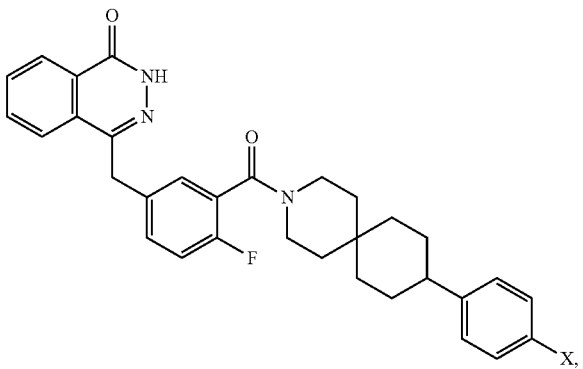

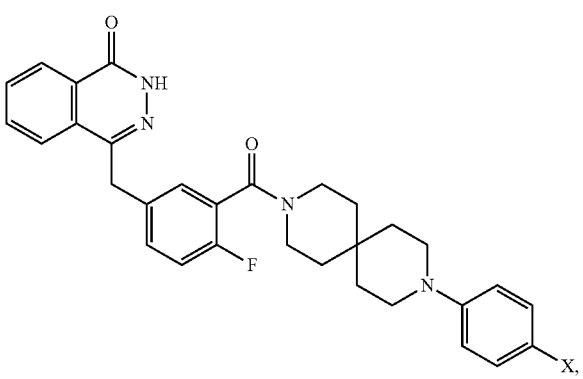

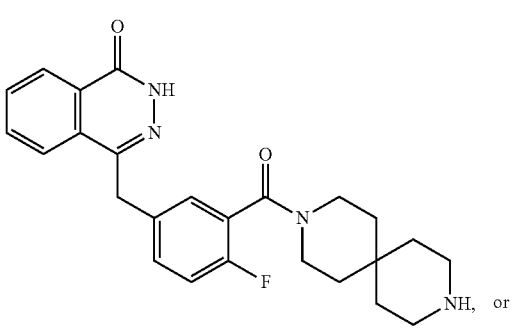

-continued

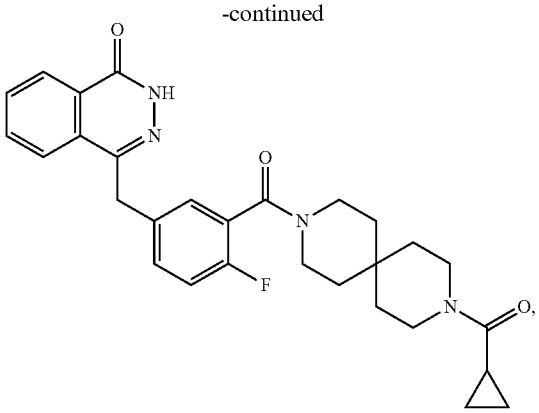

wherein X is $^{18}F$, $^{19}F$, $^{123}I$, $^{124}I$, $^{125}I$, $^{131}I$, $^{76}Br$, $^{77}Br$, or $^{211}At$.

15. A compound that is an isotopic variant of claim 1.

16. A pharmaceutical composition comprising a compound of claim 1, or a pharmaceutically acceptable salt thereof, and a pharmaceutically acceptable excipient.

17. A method of preparing a pharmaceutical composition, comprising combining a compound of claim 1, or a pharmaceutically acceptable salt thereof, with a pharmaceutically acceptable excipient.

18. A method modulating poly(ADP-ribose)polymerase-1 (PARP-1) in a subject, comprising administering to the subject a compound of claim 1, or a pharmaceutically acceptable salt thereof.

19. The method of claim 18, wherein the subject has been diagnosed with a neurodegenerative disease.

20. The method of claim 19, wherein the neurodegenerative disease is Alzheimer's disease, Parkinson's disease, or Huntington's disease.

21. A method of
    detecting a poly(ADP-ribose)polymerase-1-mediated cancer or neurodegenerative disease or disorder, comprising:
    (a) administering an effective amount of an isotopically-labeled compound of claim 1 to a subject; and
    (b) performing positron emission tomography or single photon emission computed tomography on said subject; and
    (c) detecting the isotopically-labeled compound of claim 1 in the subject.

22. The method of claim 18, wherein the subject has been diagnosed with a neurodegenerative disease or cancer.

23. The method of claim 22, wherein the cancer is breast cancer, uterine cancer, lung cancer, ovarian cancer, and skin cancer, or non-Hodgkin's lymphoma.

24. A method of monitoring poly(ADP-ribose)polymerase-1-mediated cancer treatment in a subject, comprising:
    (a) administering a chemotherapeutic or radiation to said subject;
    (b) administering an effective amount of an isotopically-labeled compound of formula I of claim 1 to said subject;
    (c) performing positron emission tomography or single photon emission computed tomography on said subject;
    (d) and detecting the isotopically-labeled compound of claim 1 in the subject.

* * * * *